United States Patent
Bray, Jr.

(10) Patent No.: US 11,026,802 B2
(45) Date of Patent: Jun. 8, 2021

(54) BONE PLATE STABILIZATION SYSTEM AND METHOD FOR ITS USE

(71) Applicant: RSB Spine LLC, Cleveland, OH (US)

(72) Inventor: Robert S. Bray, Jr., Studio City, CA (US)

(73) Assignee: RSB Spine LLC, Cleveland, OH (US)

( * ) Notice: Subject to any disclaimer, the term of this patent is extended or adjusted under 35 U.S.C. 154(b) by 0 days.

(21) Appl. No.: 16/990,863

(22) Filed: Aug. 11, 2020

(65) Prior Publication Data

US 2020/0368038 A1 Nov. 26, 2020

Related U.S. Application Data

(60) Division of application No. 15/723,522, filed on Oct. 3, 2017, which is a continuation of application No. (Continued)

(51) Int. Cl.
*A61F 2/44* (2006.01)
*A61B 17/86* (2006.01)
(Continued)

(52) U.S. Cl.
CPC .......... *A61F 2/4455* (2013.01); *A61B 17/86* (2013.01); *A61F 2/30771* (2013.01); *A61F 2/4465* (2013.01); *A61F 2002/2835* (2013.01); *A61F 2002/302* (2013.01); *A61F 2002/30056* (2013.01); *A61F 2002/30332* (2013.01); *A61F 2002/30433* (2013.01); *A61F 2002/30507* (2013.01); *A61F 2002/30517* (2013.01); *A61F 2002/30576* (2013.01); *A61F 2002/30578* (2013.01); *A61F 2002/30593* (2013.01); (Continued)

(58) Field of Classification Search
CPC ...... A61F 2/4465; A61F 2/4455; A61F 2/447; A61F 2002/30604; A61F 2/446; A61F 2002/448; A61F 2002/4485; A61F 2002/449
See application file for complete search history.

(56) References Cited

U.S. PATENT DOCUMENTS 4,503,848 A 3/1985 Caspar et al.
4,599,086 A 7/1986 Doty
(Continued)

FOREIGN PATENT DOCUMENTS

CA 2325319 5/2001
EP 0179695 A1 4/1986
(Continued)

OTHER PUBLICATIONS

Webster's II New Riverside University Dictionary, 1994, Houghton Mifflin Company, pp. 413, 1094.
(Continued)

*Primary Examiner* — Jan Christopher L Merene

(57) ABSTRACT

A bone stabilization plate system. The bone stabilization plate system includes a base plate configured to fit primarily between an anterior portion of a first bone's lip osteophyte and an anterior portion of a second, adjacent bone's lip osteophyte. The bone stabilization plate system includes a plurality of bone screws configured to fit in respective bone screw holes in the base plate to secure the base plate.

11 Claims, 42 Drawing Sheets

Related U.S. Application Data

15/625,463, filed on Jun. 16, 2017, now abandoned, which is a continuation of application No. 15/413,945, filed on Jan. 24, 2017, now Pat. No. 9,713,537, which is a continuation of application No. 15/061,007, filed on Mar. 4, 2016, now abandoned, which is a continuation-in-part of application No. 11/735,723, filed on Apr. 16, 2007, now Pat. No. 9,278,009, and a continuation-in-part of application No. 11/620,255, filed on Jan. 5, 2007, now Pat. No. 8,100,976, and a continuation-in-part of application No. 11/248,651, filed on Oct. 12, 2005, now Pat. No. 7,985,255, which is a continuation-in-part of application No. 10/419,652, filed on Apr. 21, 2003, now Pat. No. 6,984,234.

(60) Provisional application No. 60/745,294, filed on Apr. 21, 2006.

(51) Int. Cl.
*A61F 2/30* (2006.01)
*A61F 2/28* (2006.01)

(52) U.S. Cl.
CPC ............... *A61F 2002/30604* (2013.01); *A61F 2002/30616* (2013.01); *A61F 2002/30777* (2013.01); *A61F 2002/30784* (2013.01); *A61F 2002/30841* (2013.01); *A61F 2002/449* (2013.01); *A61F 2220/0016* (2013.01); *A61F 2310/00023* (2013.01)

(56) References Cited

U.S. PATENT DOCUMENTS

| | | |
|---|---|---|
| 4,759,769 A | 7/1988 | Hedman et al. |
| 4,904,261 A | 2/1990 | Dove et al. |
| 4,955,908 A | 9/1990 | Frey et al. |
| 5,306,309 A | 4/1994 | Wagner et al. |
| 5,364,399 A | 11/1994 | Lowery et al. |
| 5,405,391 A | 4/1995 | Hednerson et al. |
| 5,425,773 A | 6/1995 | Boyd et al. |
| 5,609,635 A | 3/1997 | Michelson |
| 5,645,599 A | 7/1997 | Samani |
| 5,713,898 A | 2/1998 | Stücker et al. |
| 5,713,899 A | 2/1998 | Marnay et al. |
| 5,800,433 A | 9/1998 | Benzel et al. |
| 5,861,041 A | 1/1999 | Tienboon |
| 5,865,846 A | 2/1999 | Bryan et al. |
| 5,888,223 A | 3/1999 | Bray, Jr. |
| 6,036,693 A | 3/2000 | Yuan et al. |
| 6,066,175 A | 5/2000 | Henderson et al. |
| 6,080,193 A | 6/2000 | Hochshuler et al. |
| 6,152,927 A | 11/2000 | Farris et al. |
| 6,156,037 A | 12/2000 | LeHuec et al. |
| 6,159,211 A | 12/2000 | Boriani et al. |
| 6,190,413 B1 | 2/2001 | Sutcliffe |
| 6,193,721 B1 | 2/2001 | Michelson |
| 6,200,347 B1 | 3/2001 | Anderson et al. |
| 6,228,085 B1 | 5/2001 | Theken et al. |
| 6,231,610 B1 | 5/2001 | Geisler |
| 6,235,034 B1 | 5/2001 | Bray |
| 6,235,059 B1 | 5/2001 | Benezech et al. |
| 6,245,108 B1 | 6/2001 | Biscup |
| 6,290,724 B1 | 9/2001 | Marino |
| 6,306,139 B1 | 10/2001 | Fuentes |
| 6,342,074 B1 | 1/2002 | Simpson |
| 6,371,988 B1 | 4/2002 | Pafford et al. |
| 6,413,259 B1 | 7/2002 | Lyons et al. |
| 6,432,106 B1 | 8/2002 | Fraser |
| 6,461,359 B1 | 10/2002 | Tribus et al. |
| 6,520,993 B2 | 2/2003 | James et al. |
| 6,524,311 B2 | 2/2003 | Gaines, Jr. |
| 6,533,786 B1 | 3/2003 | Needham et al. |
| 6,558,387 B2 | 5/2003 | Errico et al. |
| 6,558,423 B1 | 5/2003 | Michelson |
| 6,572,622 B1 | 6/2003 | Schäfer et al. |
| 6,579,290 B1 | 6/2003 | Hardcastle et al. |
| 6,629,998 B1 | 10/2003 | Lin |
| 6,645,208 B2 | 11/2003 | Apfelbaum et al. |
| 6,656,179 B1 | 12/2003 | Schaefer et al. |
| 6,682,530 B2 | 1/2004 | Dixon et al. |
| 6,682,563 B2 | 1/2004 | Scharf |
| 6,706,070 B1 | 3/2004 | Wagner et al. |
| 6,713,234 B2 | 3/2004 | Sandhu et al. |
| 6,730,127 B2 | 5/2004 | Michelson |
| 6,749,636 B2 | 6/2004 | Michelson |
| 6,755,833 B1 | 6/2004 | Paul et al. |
| 6,800,093 B2 | 10/2004 | Nicholson et al. |
| 6,808,537 B2 | 10/2004 | Michelson |
| 6,837,905 B1 | 1/2005 | Lieberman |
| 6,884,242 B2 | 4/2005 | LeHuec et al. |
| 6,890,355 B2 | 5/2005 | Michelson |
| 6,962,606 B2 | 11/2005 | Michelson |
| 6,972,019 B2 | 12/2005 | Michelson |
| 6,979,353 B2 | 12/2005 | Bresina |
| 6,984,234 B2 | 1/2006 | Bray |
| 7,004,944 B2 | 2/2006 | Gause |
| 7,018,416 B2 | 3/2006 | Hanson et al. |
| 7,041,135 B2 | 5/2006 | Michelson |
| 7,077,864 B2 | 7/2006 | Byrd, III et al. |
| 7,104,991 B2 | 9/2006 | Dixon et al. |
| 7,112,222 B2 | 9/2006 | Fraser |
| 7,163,561 B2 | 1/2007 | Michelson |
| 7,172,627 B2 | 2/2007 | Fiere |
| 7,232,464 B2 | 6/2007 | Mathieu et al. |
| 7,238,203 B2 | 7/2007 | Bagga et al. |
| 7,320,708 B1 | 1/2008 | Bernstein |
| 7,594,931 B2 | 9/2009 | Louis et al. |
| 7,846,207 B2 | 12/2010 | Lechmann |
| 7,875,076 B2 | 1/2011 | Mathieu et al. |
| 7,985,255 B2 | 7/2011 | Bray |
| 8,100,976 B2 | 1/2012 | Bray et al. |
| 8,343,188 B2 | 1/2013 | Michelson |
| 8,403,986 B2 | 3/2013 | Michelson |
| 8,668,741 B2 | 3/2014 | Michelson |
| 8,926,703 B2 | 1/2015 | Michelson |
| 9,039,775 B2 | 5/2015 | Fraser |
| 9,278,009 B2 | 3/2016 | Bray et al. |
| 9,713,537 B2 | 7/2017 | Bray, Jr. |
| 2001/0005796 A1 | 6/2001 | Zdeblick et al. |
| 2002/0004683 A1 | 1/2002 | Michelson |
| 2002/0016595 A1 | 2/2002 | Michelson |
| 2002/0026243 A1 | 2/2002 | Lin |
| 2002/0082597 A1 | 6/2002 | Fraser |
| 2002/0087212 A1 | 7/2002 | James et al. |
| 2002/0099376 A1 | 7/2002 | Michelson |
| 2002/0120273 A1 | 8/2002 | Needham et al. |
| 2002/0138142 A1 | 9/2002 | Castro et al. |
| 2002/0143399 A1 | 10/2002 | Sutcliffe |
| 2002/0147450 A1 | 10/2002 | LeHuec et al. |
| 2003/0028197 A1 | 2/2003 | Hanson et al. |
| 2003/0028250 A1 | 2/2003 | Reiley et al. |
| 2003/0078668 A1 | 4/2003 | Michelson |
| 2003/0120274 A1 | 6/2003 | Morris et al. |
| 2003/0130661 A1 | 7/2003 | Osman |
| 2003/0135278 A1 | 7/2003 | Eckman |
| 2003/0167091 A1 | 9/2003 | Scharf |
| 2003/0225409 A1 | 12/2003 | Freid et al. |
| 2004/0024464 A1 | 2/2004 | Errico et al. |
| 2004/0078078 A1* | 4/2004 | Shepard .................. A61F 2/447 623/17.11 |
| 2004/0078081 A1 | 4/2004 | Ferree |
| 2004/0127902 A1 | 7/2004 | Suzuki et al. |
| 2004/0193269 A1 | 9/2004 | Fraser et al. |
| 2004/0204712 A1 | 10/2004 | Kolb et al. |
| 2004/0204713 A1 | 10/2004 | Abdou |
| 2004/0236333 A1 | 11/2004 | Lin |
| 2005/0015152 A1 | 1/2005 | Sweeney |
| 2005/0065607 A1* | 3/2005 | Gross .................. A61F 2/447 623/17.11 |
| 2005/0101960 A1 | 5/2005 | Fiere et al. |
| 2005/0113918 A1* | 5/2005 | Messerli .................. A61F 2/28 623/17.11 |

(56) References Cited

U.S. PATENT DOCUMENTS

| | | | |
|---|---|---|---|
| 2005/0177236 A1 | 8/2005 | Mathieu et al. | |
| 2005/0240267 A1* | 10/2005 | Randall | A61F 2/44 623/17.11 |
| 2005/0261767 A1* | 11/2005 | Anderson | A61L 27/365 623/16.11 |
| 2006/0030851 A1 | 2/2006 | Bray et al. | |
| 2006/0085071 A1 | 4/2006 | Lechmann et al. | |
| 2008/0058810 A1 | 3/2008 | Abdou | |
| 2008/0177307 A1 | 7/2008 | Moskowitz et al. | |
| 2010/0057206 A1 | 3/2010 | Duffield et al. | |
| 2010/0087925 A1 | 4/2010 | Kostuik et al. | |
| 2010/0145459 A1 | 6/2010 | McDonough et al. | |
| 2010/0145460 A1 | 6/2010 | McDonough et al. | |
| 2018/0042733 A1 | 2/2018 | Bray, Jr. | |

FOREIGN PATENT DOCUMENTS

| | | |
|---|---|---|
| EP | 0302719 B1 | 9/1991 |
| EP | 0560140 B1 | 5/1998 |
| EP | 1103236 A2 | 5/2001 |
| EP | 1247503 A2 | 10/2002 |
| GB | 2207607 A | 2/1989 |
| JP | 2001187075 A | 7/2001 |
| JP | 2004073548 A | 3/2004 |
| WO | WO1997020526 A1 | 6/1997 |
| WO | WO1998056319 A1 | 12/1998 |
| WO | WO1998058604 A1 | 12/1998 |
| WO | WO 99/05995 A1 | 2/1999 |
| WO | WO1999027864 A2 | 6/1999 |
| WO | WO2000007527 A1 | 2/2000 |
| WO | WO2000066011 A1 | 11/2000 |
| WO | WO2000066045 A1 | 11/2000 |
| WO | WO2001026566 A1 | 4/2001 |
| WO | WO2001080785 A1 | 11/2001 |
| WO | WO2001095837 A1 | 12/2001 |
| WO | WO2002003885 A2 | 1/2002 |
| WO | WO 02/058593 A2 | 8/2002 |
| WO | WO2003005938 A1 | 1/2003 |
| WO | WO 2004/054478 A1 | 7/2004 |
| WO | WO2004069106 A1 | 8/2004 |
| WO | WO2004093654 A2 | 11/2004 |
| WO | WO2005117767 A2 | 12/2005 |

OTHER PUBLICATIONS http://reference.dictionary.com, accessed Jul. 29, 2009 for definition of opposite.
http://www.thefreedictionary.com, definition for elongate, accessed on Feb. 23, 2010.
http://www.thefreedictionary.com, definition for slender, accessed on Feb. 23, 2010.
International Search Report (PCT/US2007/087108) dated Dec. 15, 2008, 1 page.
Barry Chadwick and Chris Toto, "Radiolucent Structural Materials for Medical Applications", originally published MDDI Jun. 2001, 8 pages.
Web site page of Centinel Spine concerning product history, www.centinelspine.com/corp----producthistory.html, date indication of last update Dec. 2016, which various earlier dates discussed therein.
Life Spine Medical Holdings Inc.'s Initial Invalidity Contentions with Respect to U.S. Pat. Nos. 6,235,034, 6,984,234 and 9,713,537, Case No. C.A. No. 1:18-cv-01972-RGA, dated Sep. 9, 2019, 39 pages.
Medacta USA, Inc Initial Invalidity Contentions with Respect to U.S. Pat. Nos. 6,984,234 and 9,713,537, C.A. No. 18-1973-RGA, dated Sep. 9, 2019, 41 pages.
Haid et al., "The Cervical Spine Study Group anterior cervical plate nomenclature," Neurosurg Focus, vol. 12, pp. 1-6 (2002).
Zephir© Anterior Cervical Plate System Surgical Technique, "Medtronic Sofamor Danek-Ephir©" 16 pages (2002).
Peckett et al., "The Hartshill Horseshoe: The Treatment of Chronic Pain Patients With Discogenic Pain in the Absence of Neural Compression a Prospective 2½- to 3-Year Review," Journal of Musculoskeletal Research 4(3):209-220 (2000).
"STALIF TT™ Surgical Technique," Centinel Spine, 3 pages, cited in Medacta Initial Invalidity Contentions, Case No. CA 18-A2731973, dated Sep. 9, 2019, date unknown.
"SynFix-LR Technique Guide," Synthes, 26 pages (2006).
Madan and Boeree, "Containment and Stabilization of Bone Graft in anterior lumbar interbody fusion: the role of the Hartshill Horseshoe cage," 1 page Abstract (2001).
Madan and Boeree, "Comparison of instrumented anterior interbody fusion with instrumented circumferential lumbar fusion," Eur Spine J 12:567-575 (2003).
"The Gold Standard in Integrated Interbody Technologies," Centinel Spine, 4 pages, date unknown.
Exhibit B1 Medacta Invalidity Contentions, Case No. CA 18-A2731973, dated Sep. 9, 2019, 11 pages.
Exhibit B2 Medacta Invalidity Contentions, Case No. CA 18-A2731973, dated Sep. 9, 2019, 10 pages.
Exhibit B3 Medacta Invalidity Contentions, Case No. CA 18-A2731973, dated Sep. 9, 2019, 9 pages.
Exhibit B4 Medacta Invalidity Contentions, Case No. CA 18-A2731973, dated Sep. 9, 2019, 8 pages.
Exhibit B5 Medacta Invalidity Contentions, Case No. CA 18-A2731973, dated Sep. 9, 2019, 9 pages.
Exhibit C1 Medacta Invalidity Contentions, Case No. CA 18-A2731973, dated Sep. 9, 2019, 34 pages.
Exhibit C2 Medacta Invalidity Contentions, Case No. CA 18-A2731973, dated Sep. 9, 2019, 27 pages.
Exhibit C3 Medacta Invalidity Contentions, Case No. CA 18-A2731973, dated Sep. 9, 2019, 18 pages.
Exhibit C4 Medacta Invalidity Contentions, Case No. CA 18-A2731973, dated Sep. 9, 2019, 17 pages.
Exhibit C5 Medacta Invalidity Contentions, Case No. CA 18-A2731973, dated Sep. 9, 2019, 23 pages.
Exhibit C6 Medacta Invalidity Contentions, Case No. CA 18-A2731973, dated Sep. 9, 2019, 28 pages.
Precision Spine Inc.'s Initial Invalidity Contentions with Respect to U.S. Pat. Nos. 6,984,234 and 9,713,537, Case No. C.A. 1:18-cv-01974-RGA, dated Sep. 9, 2019, 43 pages.
Exhibit 1 to Precision Spine Inc.'s Initial Invalidity Contentions, Case No. CA 18-1974-RGA, dated Sep. 9, 2019, 55 pages.
Exhibit 2 to Precision Spine Inc.'s Initial Invalidity Contentions, Case No. CA 18-1974-RGA, dated Sep. 9, 2019, 33 pages.
Exhibit 3 to Precision Spine Inc.'s Initial Invalidity Contentions, Case No. CA 18-1974-RGA, dated Sep. 9, 2019, 38 pages.
Exhibit 4 to Precision Spine Inc.'s Initial Invalidity Contentions, Case No. CA 18-1974-RGA, dated Sep. 9, 2019, 30 pages.
Exhibit 5 to Precision Spine Inc.'s Initial Invalidity Contentions, Case No. CA 18-1974-RGA, dated Sep. 9, 2019, 36 pages.
Exhibit 6 to Precision Spine Inc.'s Initial Invalidity Contentions, Case No. CA 18-1974-RGA, dated Sep. 9, 2019, 46 pages.
Exhibit 7 to Precision Spine Inc.'s Initial Invalidity Contentions, Case No. CA 18-1974-RGA, dated Sep. 9, 2019, 41 pages.
Exhibit 8 to Precision Spine Inc.'s Initial Invalidity Contentions, Case No. CA 18-1974-RGA, dated Sep. 9, 2019, 34 pages.
Exhibit 9 to Precision Spine Inc.'s Initial Invalidity Contentions, Case No. CA 18-1974-RGA, dated Sep. 9, 2019, 21 pages.
Exhibit 10 to Precision Spine Inc.'s Initial Invalidity Contentions, Case No. CA 18-1974-RGA, dated Sep. 9, 2019, 20 pages.
Exhibit 11 to Precision Spine Inc.'s Initial Invalidity Contentions, Case No. CA 18-1974-RGA, dated Sep. 9, 2019, 29 pages.
Exhibit 12 to Precision Spine Inc.'s Initial Invalidity Contentions, Case No. CA 18-1974-RGA, dated Sep. 9, 2019, 35 pages.
Xtant Medical Holdings Inc.'s Initial Invalidity Contentions with Respect to U.S. Pat. No. 6,984,234 and 9,713,537, Case No. CA 1:188-01976-RGA, dated Sep. 9, 2019, 42 pages.
Exhibit 1 to Xtant Medical Holdings Inc.'s Initial Invalidity Contentions with Respect to U.S. Pat. Nos. 6,984,234 and 9,713,537, Case No. CA 1:188-01976-RGA, dated Sep. 9, 2019, 169 pages.
Corrected Exhibit 2A to Xtant Medical Holdings Inc.'s Initial Invalidity Contentions with Respect to U.S. Pat. Nos. 6,984,234 and 9,713,537, Case No. CA 1:188-01976-RGA, dated Sep. 9, 2019, 171 pages.

(56) References Cited

OTHER PUBLICATIONS

Exhibit 2a to Xtant Medical Holdings Inc.'s Initial Invalidity Contentions with Respect to U.S. Pat. Nos. 6,984,234 and 9,713,537, Case No. CA 1:188-01976-RGA, dated Sep. 9, 2019, 171 pages.
Exhibit 2b to Xtant Medical Holdings Inc.'s Initial Invalidity Contentions with Respect to U.S. Pat. Nos. 6,984,234 and 9,713,537, Case No. CA 1:188-01976-RGA, dated Sep. 9, 2019, pages.
Defendants' Answer, Affirmative Defenses, and Counterclaims to Plaintiff's Amended Complaint, C.A. No. 19-1515-RGA—dated Oct. 15, 2019, 35 pages.
Medacta USA, Inc., Precision Spine, Inc., and Life Spine, LLC Petition for Inter Partes Review of U.S. Pat. No. 9,713,537 Challenging Claims 1, 3-6, 10, 13-15, 18, 19, 21, 22, 24, 29 and 30, Case No. IPR2020-00264, dated Dec. 13, 2019, 103 pages.
Petitioners' Ranking and Explanation for Two Petitions Challenging U.S. Pat. No. 6,984,234, Case No. IPR2020-00264 relating to U.S. Pat. No. 9,713,537, dated Dec. 13, 2019, 6 pages.
Declaration of Michael Sherman in Support of Petitioner regarding U.S. Pat. No. 9,713,537 (Claims 1, 3-6, 10, 13-15, 18, 21, 22, 24, 29 and 30), Case No. IPR2020-00264, dated Dec. 13, 2019, 191 pages.
Declaration of Michael Sherman in Support of Petitioner regarding U.S. Pat. No. 9,713,537 (Claims 1, 3-6, 10, 13-15, 18, 21, 22, 24, 29 and 30), Case No. IPR2020-00264, dated Dec. 13, 2019, 198 pages.
Disputed Terms for Construction, Exhibit 1017 to Medacta USA, Inc., Precision Spine, Inc., and Life Spine, LLC Petition for Inter Partes Review of U.S. Pat. No. 9,713,537 Challenging Claims 1, 3-6, 10, 13-15, 18, 19, 21, 22, 24, 29 and 30, Case No. IPR2020-00264, dated Dec. 12, 2019, 6 pages.
Medacta USA, Inc., Precision Spine, Inc., and Life Spine, LLC Petition for Inter Partes Review of U.S. Pat. No. 6,984,234 Challenging Claims 35, 37 and 39 Case No. IPR2020-00265, dated Dec. 13, 2019, 102 pages.
Declaration of Michael Sherman in Support of Petitioner regarding U.S. Pat. No. 6,984,234 (Claims 35, 37, and 39), Case No. IPR2020-00265, dated Dec. 13, 2019, 113 pages.
Declaration of Michael Sherman in Support of Petitioner regarding U.S. Pat. No. 6,984,234 (Claims 35, 37, and 39), Case No. IPR2020-00265, dated Dec. 13, 2019, 120 pages.
Petitioners' Ranking and Explanation for Two Petitions Challenging U.S. Pat. No. 6,984,234, Case No. IPR2020-00265 relating to U.S. Pat. No. 6,984,234, dated Dec. 13, 2019, 6 pages.
Medacta Usa, Inc., Precision Spine, Inc., and Life Spine, LLC Petition for Inter Partes Review of U.S. Pat. No. 6,984,234 Challenging Claims 1-10, 13-14, 16, 18-20, 22, 24-25, 28-29 and 31-32, Case No. IPR2020-00274, dated Dec. 13, 2019, 91 pages.
Declaration of Michael Sherman in Support of Petitioner regarding U.S. Pat. No. 6,984,234, Case No. IPR2020-00274, dated Dec. 13, 2019, 121 pages.
Declaration of Michael Sherman in Support of Petitioner regarding U.S. Pat. No. 6,984,234, Case No. IPR2020-00274, dated Dec. 13, 2019, 128 pages.
Medacta USA, Inc., Precision Spine, Inc., and Life Spine, LLC Petition for Inter Partes Review of U.S. Pat. No. 9,713,537 Challenging Claims 1, 3-6, 10, 13-15, 18-19- 21-22, 24, 29-30, Case No. IPR2020-00275, dated Dec. 13, 2019, 98 pages.
Declaration of Michael Sherman in Support of Petitioner regarding U.S. Pat. No. 9,713,537, Case No. IPR2020-00275, dated Dec. 13, 2019, 122 pages.
Declaration of Michael Sherman in Support of Petitioner regarding U.S. Pat. No. 9,713,537, Case No. IPR2020-00275, dated Dec. 13, 2019, 129 pages.
Proposed claim Terms/Phrases and Constructions, filed in C.A. No. 18-1972-RGA, C.A. No. 18-1973-RGA, C.A. No. 18-1974-RGA, C.A. No. 18-1976-RGA and C.A. No. 19-1515-RGA, dated Dec. 2, 2019.
"Dorland's Illustrated Medical Dictionary, 30th Edition," W.A. Newman Dorland W B Saunders, 10 pages (2003).

Petitioners' Ranking and Explanation for Two Petitions Challenging U.S. Pat. No. 6,984,234, Case No. IPR2020-00274 , dated Dec. 13, 2019, 6 pages.
Arcadius XP™ L Spinal System by Aesculap Implant Systems, Product Brochure, 8 pages, date unknown.
"Arcadius XP™ L: Evolution Spinal System, Surgical Technique," Aesculap Implant Systems, 36 pages (2019).
AxHA™ Stand Alone ALIF System by Innovasis Brochure, 3 pages, date unknown.
Ax™ Stand Alone ALIF System by Innovasis, Surgical Technique Guide, 25 pages, date unknown.
MectaLIF Anterior Lumbar Interbody Fusion Device by Medacta Corporate, 24 pages (2018).
Endoskeleton® TAS by Medtronic (Titan Spine), 2 pages (2014).
Endoskeleton® TCS by Medtronic (Titan Spine), 2 pages 2014).
Vault® C ACDF System by Precision Spine® Brochure, 2 pages, date unknown.
Vault® C ACDF System by Precision Spine®, Surgical Technique Guide, 22 pages, date unknown.
Magnum+® Stand-Alone, No Profile ALIF by Spinal Elements Brochure , 4 pages, no date provided.
AVS® Anchor-C Cervical Cage System by Stryker Spine Brochure, 2 pages, date unknown.
AVS® Anchor-C Cervical Cage System by Stryker Spine, Surgical Technique Guide, 24 pages (2015).
AVS Anchor®-L Lumbar Cage System by Stryker Spine Brochure, 2 pages, date unknown.
AVS Anchor®-L Lumbar Cage System by Stryker Spine, Surgical Technique Guide, 32 pages (2015).
Alta™ Stand-Alone ACDF System by Zimmer Biomet Spine, 28 pages (2018).
Alta Stand-Alone Interbody Fusion System by Biomet Spine, Brochure, 1 page , date unknown.
Durango™ Stand-Alone ALIF System by Zimmer Biomet Spine, 32 pages (2014).
Durango™ Stand-Alone ALIF System by Zimmer Biomet Spine Surgical Technique Guide, 32 pages (2017).
Avenue® L Lateral Lumbar Cage by Zimmer Biomet Spine Brochure, 2 pages, date unknown.
Avenue® L Lateral Lumbar Cage by Zimmer Biomet Spine, Surgical Technique Guide, 56 pages (2017).
Defendants DePuy Synthes Products, Inc., and DePuy Synthes Sales, Inc.'s Preliminary Invalidity Contentions, C.A. No. 19-1515-RGA, dated Mar. 6, 2020, 11 pages.
Exhibits A1-A7 to Defendants DePuy Synthes Products, Inc., and DePuy Synthes Sales, Inc.'s Preliminary Invalidity Contentions, C.A. No. 19-1515-RGA, dated Mar. 6, 2020, 125 pages.
Exhibits B1-B7 to Defendants DePuy Synthes Products, Inc., and DePuy Synthes Sales, Inc.'s Preliminary Invalidity Contentions, C.A. No. 19-1515-RGA, dated Mar. 6, 2020, 156 pages.
Decision Granting Institution of Inter Partes Review issued in Medacta USA, Inc., Precision Spine, Inc., and Life Spine, LLC Petition for Inter Partes Review of U.S. Pat. No. 9,713,537 Challenging Claims 1, 3-6, 10, 13-15, 18, 19, 21, 22, 24, 29 and 30, Case No. IPR2020-00264, dated May 22, 2020, 62 pages.
Decision Granting Institution of Inter Partes Review issued in Medacta USA, Inc., Precision Spine, Inc., and Life Spine, LLC Inter Partes Review of U.S. Pat. No. 6,984,234 Challenging Claims 35, 37 and 39 Case No. IPR2020-00265, dated May 22, 2020, 56 pages.
Decision Granting Institution of Inter Partes Review issued in Medacta USA, Inc., Precision Spine, Inc., and Life Spine, LLC Petition for Inter Partes Review of U.S. Pat. No. 6,984,234 Challenging Claims 1-10, 13-14, 16, 18-20, 22, 24-25, 28-29 and 31-32, Case No. IPR2020-00274, dated May 22, 2020, 52 pages.
Decision Denying Institution of Inter Partes Review issued in Medacta USA, Inc., Precision Spine, Inc., and Life Spine, LLC Petition for Inter Partes Review of U.S. Pat. No. 9,713,537 Challenging Claims 1, 3-6, 10, 13-15, 18-19- 21-22, 24, 29-30, Case No. IPR2020-00275, dated May 22, 2020, 13 pages.
Final Office Action issued by the United States Patent and Trademark Office for U.S. Apl. No. 15/723,522, dated Mar. 26, 2020, 17 pages.

(56) References Cited

OTHER PUBLICATIONS

Non-Final Office Action issued by the United States Patent and Trademark Office for U.S. Appl. No. 15/723,522, dated Aug. 23, 2019, 26 pages.

Interview Summary issued by the United States Patent and Trademark Office for U.S. Appl. No. 15/723,522, dated Dec. 16, 2019, 7 pages.

Interview Summary issued by the United States Patent and Trademark Office for U.S. Appl. No. 15/723,522, dated Jun. 29, 2020, 4 pages.

Non-Final Office Action issued by the United States Patent and Trademark Office for U.S. Appl. No. 15/723,522, dated Aug. 23, 2019, 23 pages.

Office Action—Interview Summary—issued by the United States Patent and Trademark Office for U.S. Appl. No. 15/723,522, dated Dec. 16, 2019, 7 pages.

Non-Final Office Action issued by the United States Patent and Trademark Office for U.S. Appl. No. 15/723,522, dated Sep. 11, 2020, 23 pages.

\* cited by examiner

BONE PLATE STABILIZATION SYSTEM AND METHOD FOR ITS USE

RELATED PATENT APPLICATIONS

This application claims the benefit of priority from and incorporates herein by reference in their entirety all of the several applications identified herein. Specifically, this application is a division of U.S. patent application Ser. No. 15/723,522, filed on Oct. 3, 2017, which is a continuation application of U.S. patent application Ser. No. 15/625,463, now abandoned, filed on Jun. 16, 2017, which in turn is a continuation application of U.S. patent application Ser. No. 15/413,945, filed on Jan. 24, 2017, now U.S. Pat. No. 9,713,537, which in turn is a continuation application of U.S. patent application Ser. No. 15/061,007, now abandoned, filed Mar. 4, 2016, which in turn is a continuation-in-part application of U.S. patent application Ser. No. 11/735,723, filed Apr. 16, 2007, now U.S. Pat. No. 9,278,009, which in turn claims benefit of, as a non-provisional application of, U.S. Provisional Patent Application No. 60/745,294, filed Apr. 21, 2006. U.S. patent application Ser. No. 11/735,723 also is a continuation-in-part application of U.S. patent application Ser. No. 11/620,255, filed Jan. 5, 2007, now U.S. Pat. No. 8,100,976, and a continuation-in-part application of U.S. patent application Ser. No. 11/248,651, filed Oct. 12, 2005, now U.S. Pat. No. 7,985,255. U.S. patent application Ser. No. 11/248,651 is a continuation-in-part application of U.S. patent application Ser. No. 10/419,652, filed Apr. 21, 2003, now U.S. Pat. No. 6,984,234. The contents of all of the foregoing applications are incorporated herein by reference in their entirety.

FIELD OF THE INVENTION

The present invention relates generally to implant devices for the fixation and support of bone bodies. In particular, the present invention relates to an implant device that provides and controls limited movement between bone bodies during fusion, having subsidence control.

BACKGROUND OF THE INVENTION

The spinal column of vertebrates provides support to bear weight and protection to the delicate spinal cord and spinal nerves. The spinal column comprises a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior which covers the neural structures. Between each vertebral body is an intervertebral disk, a cartilaginous cushion to help absorb impact and dampen compressive forces on the spine. To the posterior the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition congenital or acquired deformities can cause abnormal angulation or slippage of the spine. Slippage (spondylolisthesis) anterior of one vertebral body on another can cause compression of the spinal cord or nerves. Patients who suffer from one of more of these conditions often experience extreme and debilitating pain, and can sustain permanent neurologic damage if the conditions are not treated appropriately.

One technique of treating these disorders is known as surgical arthrodesis of the spine. This can be accomplished by removing the intervertebral disk and replacing it with bone and immobilizing the spine to allow the eventual fusion or growth of the bone across the disk space to connect the adjoining vertebral bodies together. The stabilization of the vertebra to allow fusion is often assisted by a surgically implanted device to hold the vertebral bodies in proper alignment and allow the bone to heal, much like placing a cast on a fractured bone. Such techniques have been effectively used to treat the above described conditions and in most cases are effective at reducing the patient's pain and preventing neurologic loss of function. However, there are disadvantages to the present stabilization devices.

The spinal fixation device needs to allow partial sharing of the weight of the vertebral bodies across the bone graft site. Bone will not heal if it is stress shielded from all weight bearing. The fixation device needs to allow for this weight sharing along with the micromotion that happens during weight sharing until the fusion is complete, often for a period of three to six months or longer, without breakage. The device must be strong enough to resist collapsing forces or abnormal angulation during the healing of the bone. Loss of alignment during the healing phase can cause a poor outcome for the patient. The device must be secure in its attachment to the spine to prevent migration of the implant or backout of the screws from the bone which could result in damage to the structures surrounding the spine, resulting in severe and potentially life threatening complications. The device must be safely and consistently implanted without damage to the patient.

Several types of anterior spinal fixation devises are in use currently. One technique involves placement of screws all the way through the vertebral body, called bicortical purchase. The screws are placed through a titanium plate but are not attached to the plate. This device is difficult to place, and over penetration of the screws can result in damage to the spinal cord. The screws can back out of the plate into the surrounding tissues as they do not fix to the plate. Several newer generation devices have used a unicortical purchase of the bone, and in some fashion locking the screw to the plate to provide stability and secure the screw from backout. Problems have resulted from over ridged fixation and stress shielding, resulting in nonunion of the bony fusion, chronic micromotion during healing resulting in stress fracture of the fixation device at either the screw or the plate, insecure locking of the screw to the plate resulting in screw backout, or inadequate fixation strength and resultant collapse of the graft and angulation of the spine.

These devices are often designed to support and bridge across a group of vertebrae, for example a group of three. Because these devices are typically bridged across the bone, for example in the cervical region, they occasionally aggravate the esophagus, making it difficult for one to swallow food. In addition, the screws are installed into the bone normal, i.e., 90° to the plate's surface. Local angularity in the vertebral column often causes high shearing stresses to be applied to the screws. These stresses may fatigue the screws or cause deformation of the screw holes.

Thus, there is a need for a device and method of supporting adjacent vertebrae that avoids these problems and risks to the patient.

Bone mechanical properties greatly influence the stiffness of vertebra-implant-vertebra constructs. Bone properties are a function of many factors including bone mineral density, age, and sex. For comparative purposes, it will be assumed that bone properties are constant in the following discussions. Preparation of the bone to receive the implant can influence strength and stiffness. Again, for comparative purposes, it will be assumed that bone preparation is not a variable except when specifically discussed.

Interbody devices are typically classified as threaded cylinders or screws (e.g., BAK C), boxes (usually tapered rectangular boxes with ridges like the Brantigan cage), or vertical cylinders (e.g., Harms cage). Threaded cylinders usually have small pores and graft material is located inside the hollow interior of the cylinder. Device stiffness might be an issue for such designs. Boxes and vertical cylinders are generally open structures and in these devices a combination of device stiffness and subsidence are responsible for loading the graft.

The stiffness of a material and the stiffness of the structure (device) are often confused. Material stiffness is quantified by Modulus of Elasticity, the slope of the stress-strain curve. Steel has a high modulus, and gold has a low modulus. Structural or device stiffness is a function of dimensions of the part and the material from which the part is made. For example, steel is a very stiff material. However, when formed into the shape of a structure like a paperclip it is easily bent. Stiffness of an assembly or construct can be influenced by connections. While a paperclip and even a piece of paper are strong in tension, when assembled with a piece of paper a paperclip can be easily pulled off because they are only held together by friction.

The same analogy holds for inter-vertebral implants. For instance, consider a simplified construct consisting of a bone block, an interbody device, and a bone block, stacked on top of each other and loaded in compression. If the device is made from a low modulus material but has a large footprint on the bone, and conforms very well to the bone, the assembly can be very stiff in compression. The slope of the load-deflection curve would be steep. A device made from a high modulus material that has a small footprint on the bone and sharp edges might simply punch into the bone under compressive load. The slope of the load-deflection curve would be low, making the construct appear very compliant despite the fact that the device is rigid.

The terms flexibility and stiffness are used in connection with both the range of motion of the spine and the mechanical performance of implant constructs, and the distinction is not always clearly defined.

The spinal column of vertebrates provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disc, a cartilaginous cushion to help absorb impact and dampen compressive forces on the spine. To the posterior the laminar arch covers the neural structures of the spinal cord and nerves for protection. At the junction of the arch and posterior vertebral body are articulations to allow movement of the spine.

Various types of problems can affect the structure and function of the spinal column. These can be based on degenerative conditions of the intervertebral disc or the articulating joints, traumatic disruption of the disc, bone or ligaments supporting the spine, tumor or infection. In addition congenital or acquired deformities can cause abnormal angulation or slippage of the spine. Slippage (spondylolisthesis) anterior of one vertebral body on another can cause compression of the spinal cord or nerves. Patients who suffer from one of more of these conditions often experience extreme and debilitating pain, and can sustain permanent neurological damage if the conditions are not treated appropriately.

One technique of treating these disorders is known as surgical arthrodesis of the spine. This can be accomplished by removing the intervertebral disc and replacing it with bone and immobilizing the spine to allow the eventual fusion or growth of the bone material across the disc space to connect the adjoining vertebral bodies together. The stabilization of the vertebra to allow fusion is often assisted by a surgically implanted device to hold the vertebral bodies in proper alignment and allow the bone to heal, much like placing a cast on a fractured bone. Such techniques have been effectively used to treat the above-described conditions and in most cases are effective at reducing the patient's pain and preventing neurological loss of function. However, there are disadvantages to the present stabilization devices.

Several types of anterior spinal fixation devices are in use currently. One technique involves placement of screws all the way through the vertebral body, called bicortical purchase. The screws are placed through a titanium plate but are not attached to the plate. This device is difficult to place, and over penetration of the screws can result in damage to the spinal cord. The screws can back out of the plate into the surrounding tissues, as they do not fix to the plate. Several newer generation devices have used a unicortical purchase of the bone, and in some fashion locking the screw to the plate to provide stability and secure the screw from back out. Problems have resulted from over rigid fixation and stress shielding, resulting in nonunion of the bony fusion, chronic micro-motion during healing resulting in stress fracture of the fixation device at either the screw or the plate, insecure locking of the screw to the plate resulting in screw back out, or inadequate fixation strength and resultant collapse of the graft and angulation of the spine.

These devices are often designed to support and bridge across a group of vertebrae, for example a group of three. Because these devices are typically bridged across the bone, for example in the cervical region, they occasionally aggravate the esophagus, making it difficult for one to swallow food. In addition, the screws are installed into the bone normal, i.e., 90° to the plate's surface. Local angularity in the vertebral column often causes high shearing stresses to be applied to the screws. These stresses may fatigue the screws or cause deformation of the screw holes.

BRIEF SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with an aspect of the present invention, at least one implant device is provided.

The following description and the annexed drawings set forth in detail certain illustrative aspects of the invention.

These aspects are indicative, however, of but a few of the various ways in which the principles of the invention may be employed and the present invention is intended to include all such aspects and their equivalents. Other objects, advantages and novel features of the invention will become apparent from the following detailed description of the invention when considered in conjunction with the drawings.

BRIEF DESCRIPTION OF THE DRAWINGS

The foregoing and other features and advantages of the present invention will become apparent to those skilled in the art to which the present invention relates upon reading the following description with reference to the accompanying drawings.

DESCRIPTION OF EXAMPLE EMBODIMENTS

Figure 1:
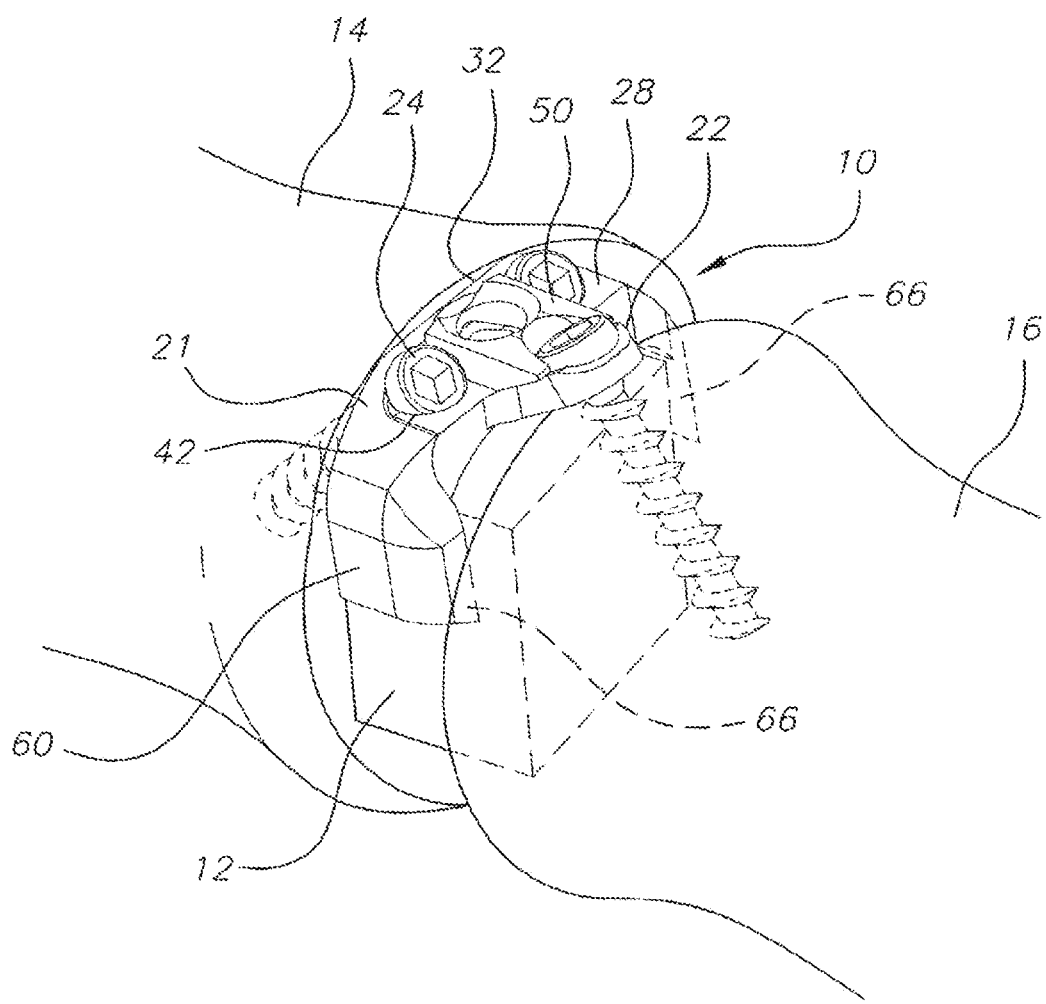
FIG. 1 is a perspective view of a bone stabilization plate system according to the invention that is assembled between adjacent vertebrae.
Figure 2:
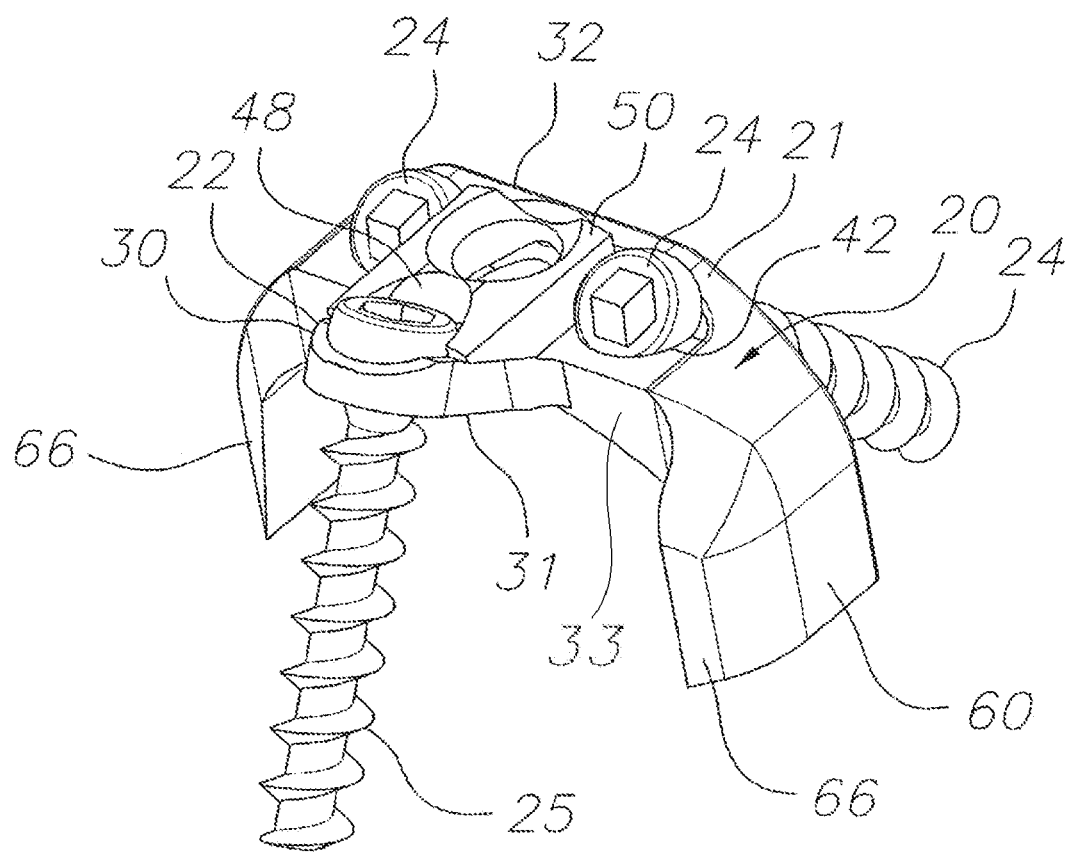
FIG. 2 is a perspective view of the bone stabilization plate system of FIG. 1.

The present invention relates to a device, such as an implant device that provides and controls limited movement between bone bodies during fusion. The present invention will now be described with reference to the drawings, wherein like reference numerals are used to refer to similar elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

While some embodiments of the present invention are described for supporting adjacent cervical vertebrae in the anterior region of the vertebrae, persons skilled in the art would recognize that the bone plate of the present invention may be utilized to support adjoining thoracic and lumbar vertebrae in the lateral or posterior regions of the vertebrae. Further, the device and method of the invention is not limited to vertebral bodies, but can also be used to join two other pieces of bone in other parts of the body.

Some aspects provide a bone stabilization plate system for stabilizing two adjacent bones (including bone fragments), such as adjacent vertebral bodies, while they heal, as well as to methods for its use. A useful bone stabilization plate system 10 constructed in accordance with the present invention is shown in FIGS. 1 to 4. The depicted bone stabilization plate system comprises a base plate 20 having first and second ends, and including a primary member 21 and a secondary member 22 at the second end 33 of the base plate. The secondary member 22 is angled relative to the primary member 21, as discussed further below, although other designs are contemplated within the scope of the invention.

The base plate 20 may be made of any suitable material, and can be made from titanium or a titanium alloy. The thickness of the base plate 20 is not critical, and can range from about 1 mm to about 2 mm, and more specifically is about 1.6 mm. The thickness of the base plate 20 will depend on the particular application.

Figure 3:
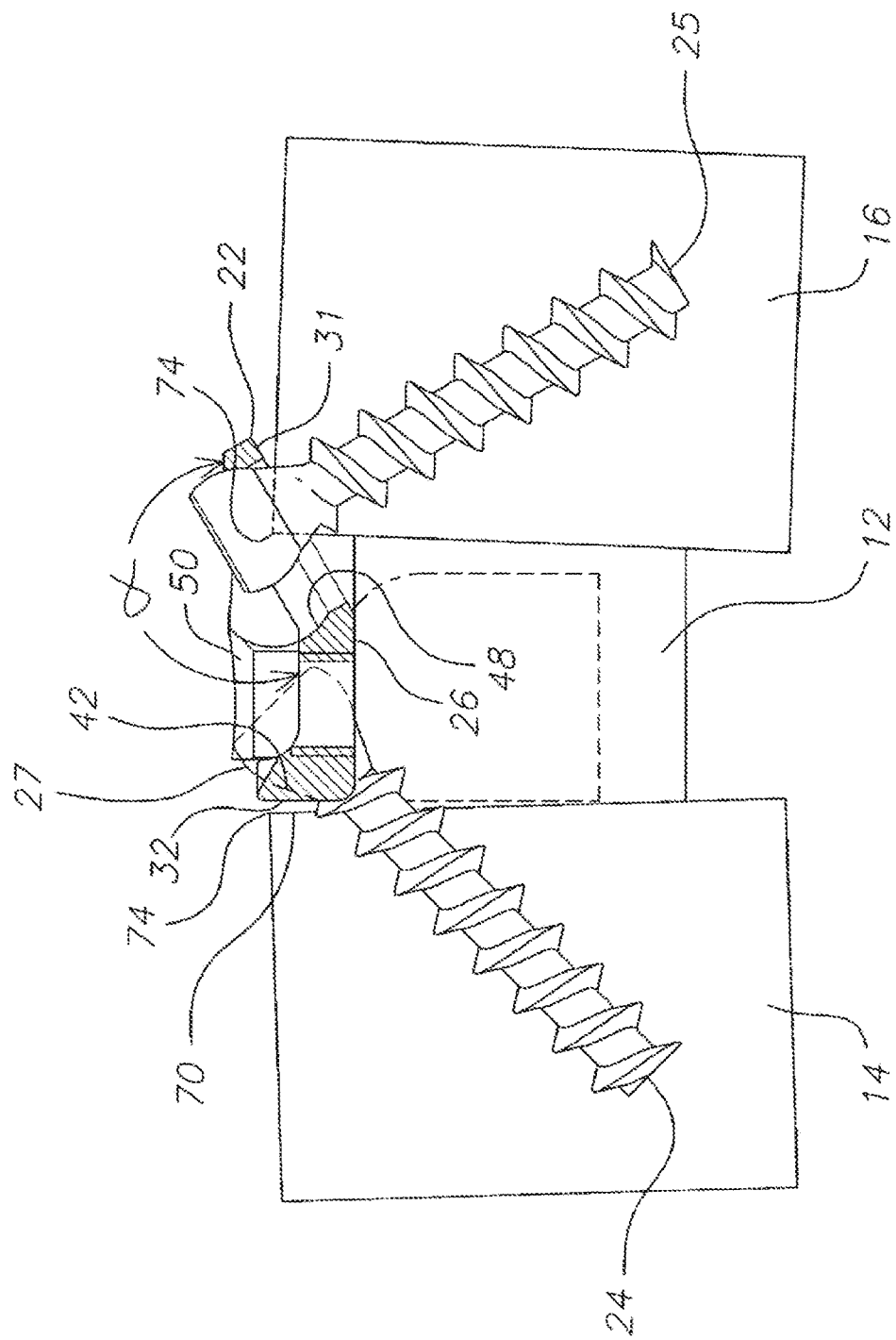
FIG. 3 is a side cross-sectional view of the bone stabilization plate system of FIG. 1 assembled between adjacent vertebrae.

FIGS. 1 and 3 show the base plate 20 mounted to first and second adjacent vertebral bodies 14 and 16 with a bone graft 12 between the vertebral bodies. The base plate 20 has a bottom surface 26 that contacts the bone graft 12. The bottom surface is therefore can be generally flat, but can have any other design that permits it to sit against the bone graft is suitable for use in the invention. In the depicted embodiment, the bottom surface 26 of the base plate 20 is the bottom surface of the primary member 21. The primary member includes a top surface 28 that is opposite the bottom surface 26 and a side wall 32 at the first end of the base plate 20 that joins the top and bottom surfaces and contacts the first vertebral bodies 14. The top surface 28 can have any suitable design so that it can receive one or more bone screws and perform as described further below.

The secondary member 22 has a front surface 30 that is generally continuous with the top surface 28 of the primary member 21 and a back surface 31 that is generally continuous with the bottom surface 26 of the primary member. The primary member 21 and secondary member 22 are arranged relative to each other so that their top surfaces form an angle $\alpha$ that is greater than 90° and less than 180°, specifically from 110° to about 160°. As will become apparent, the angle at which the primary and secondary members are joined is provided so that bone screws can be introduced through the base plate at desired angles, as discussed further below. Accordingly, the base plate 20 can be designed in any other manner that permits the bone screws to be introduced therethrough at the desired angles.

Figure 4:
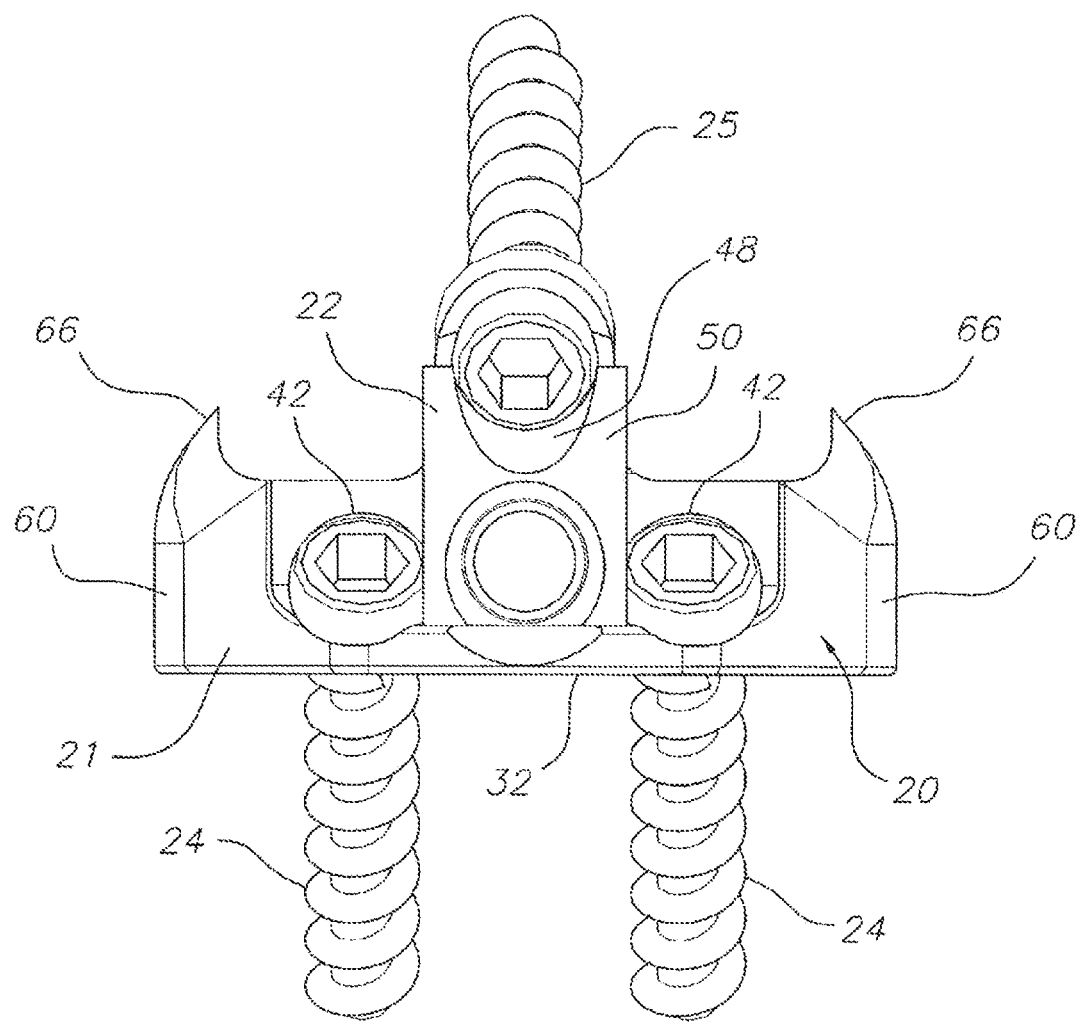
FIG. 4 is a top view of the bone stabilization plate system of FIG. 1.

The primary member 21 includes at least one, and possibly two (as shown in the depicted embodiment) first bone screw holes 42 extending therethrough for receiving a corresponding number of first bone screws 24. The bone screw holes 42 in the primary member 21 are angled relative to the bottom surface 26 of the base plate and primary member so that a first bone screw extending through first a bone screw hole extends through the base plate at an angle relative to the bottom surface, for example, through the corner joining the bottom surface 26 to the side wall 32, as best shown in FIG. 4. As a result, the each first bone screw 24 extends into the first vertebral body 14 at an angle, as discussed further below. In the depicted embodiment, each first bone screw hole 42 has a generally conical shape to receive the "radiused" shape of the bottom of the head of the corresponding first bone screw 24, described further below, but can have any other suitable shape depending upon the shape of the bone screws to be used.

The secondary member 22 includes a bone screw hole in the form of an elongated bone screw hole or slot 48 for receiving a second bone screw 25. The second bone screw 25 is introduced into the bone screw slot 48 and into the second vertebral body 16. The bone screw slot 48 is designed so that the second bone screw 25 can slide within the slot relative to the base plate 20 generally toward the primary member 21. Thus, in use, as the two vertebral bodies 14 and 16 to which the base plate 20 is fixed collapse or settle and move toward each other, the second bone screw 25 contained within the bone screw slot 48 will slide within the slot and move with the second vertebral body 16 into which it extends in a direction toward the primary member 21 and the first vertebral body 14.

Figure 5:
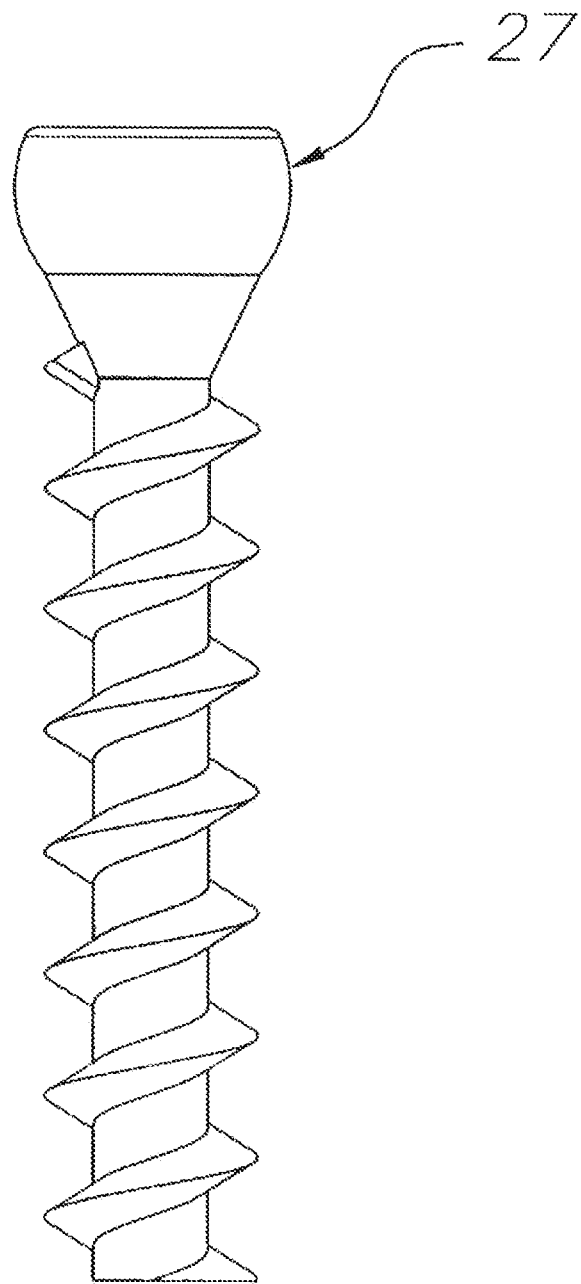
FIG. 5 is a side view of a bone screw for use in the bone stabilization plate system depicted in FIGS. 1 to 4.

The bone screws 24 and 25 can be made of any suitable material, and can be made of the same material as the base plate 20, such as titanium or a titanium alloy. The bone screws 24 and 25 can all have the same shape, such as that shown in FIG. 5. In the depicted embodiment, the bone screws 24 and 25 each have a radiused head 27. As used herein, the term "radiused head" means that the lower portion of the bone screw head, i.e., the portion that is nearest the shank, is generally rounded, to thereby permit the bone screws to toggle within their respective holes and slot. The bone screws 24 and 25 can have any other suitable shape that permits them to cooperate with the bone screw holes 42 and the bone screw slot 48.

The system 10 is designed so that the bone screws 24 and 25 are introduced into the vertebral bodies 14 and 15 at an angle other than 90° relative to the bone surface. In one case, the first bone screws 24 are introduced into the first vertebral body 14 so that the axis of each bone screw is at an angle relative to the bone surface ranging from about 20° to about 60°, more specifically from about 40° to about 50°. The second bone screw 25 can be introduced into the second vertebral body 16 so that the axis of the bone screw is at an angle relative to the bone surface ranging from about 20° to about 70°, more specifically from about 45° to about 65°.

The bone stabilization plate system includes a bone screw retaining means, which is any means for securely covering at least a part of each of the bone screws 24 and 25 so that the bone screws cannot back out from the bone once screwed in through the base plate 20. In the depicted embodiment, the bone screw retaining means comprises a retaining plate 50 and a retaining plate fixing means.

Figure 6:
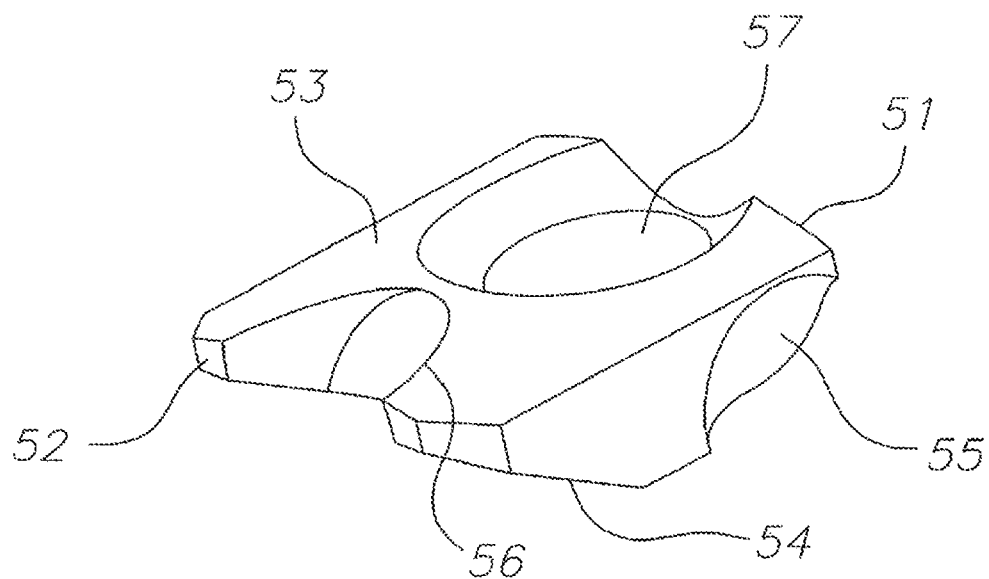
FIG. 6 is a perspective view of a retaining plate for use in the bone stabilization plate system depicted in FIGS. 1 to 4.
Figure 7:
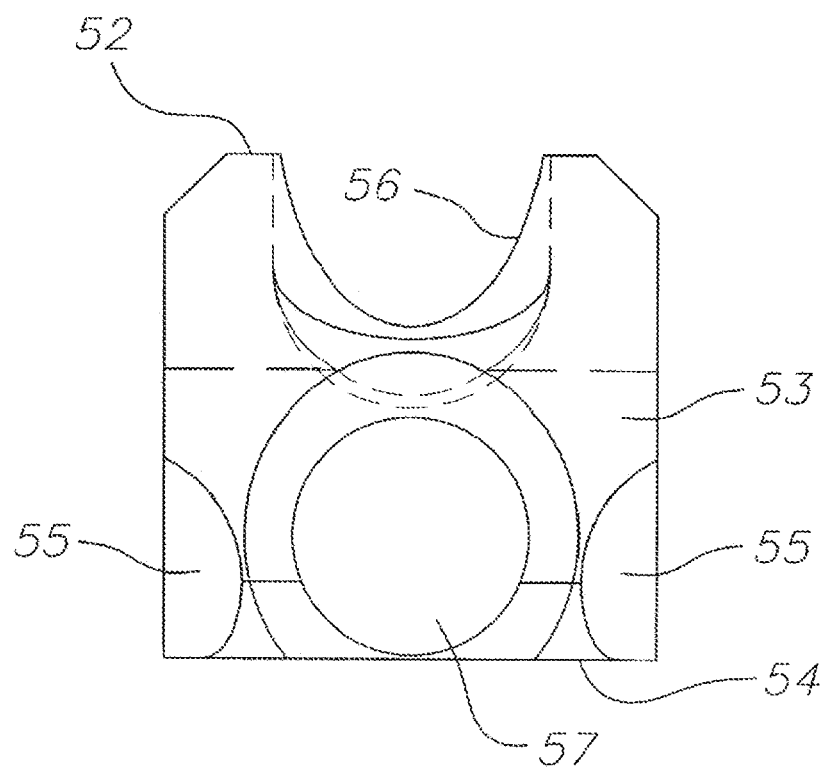
FIG. 7 is a top view of the retaining plate of FIG. 6.

As best shown in FIGS. 6 and 7, the retaining plate 50 is a generally flat plate having a first end 51, a second end 52, a top surface 53 and a bottom surface 54 that is shaped to sit against the top surface 28 of the base plate 20. In the depicted embodiment, the retaining plate 50 sits in a recessed region of the base plate 20, as best shown in FIG. 3. The use of a recessed region permits the user to more easily properly place the retaining plate on the base plate. The thickness of the retaining plate 50 is not critical, but can be ranges from about 0.5 mm to about 2 mm, more specifically from about 1 mm to about 1.5 mm.

The retaining plate 50 includes at its first end 51 two generally-rounded notches 55 on the sides of its bottom surface 54. When the retaining plate 50 is fixed in place over the base plate 20, the two generally-rounded notches 55 each cover a portion of a corresponding one of the first bone screws 24. The generally-rounded nature of the notches 55 permits the first bone screws 24 to toggle within the first bone screw holes 42.

The retaining plate includes at its second end 52 a U-shaped notch 56, which, in the depicted embodiment, is centered at the edge of the second end. The U-shaped notch 56 includes a generally U-shaped sidewall between the top and bottom surfaces of the retaining plate that is curved outwardly from the top surface 53 to the bottom surface 54 so that the opening formed by the notch is larger at the bottom surface of the retaining plate and smaller at the top surface of the retaining plate. When the retaining plate 50 is fixed in place over the base plate 20, the top of the second bone screw 25 sits within the U-shaped notch 56 with the top of the second bone screw covered by the top surface 53 of the retaining plate. With this design, the second bone screw 25 is permitted to slide and toggle within the bone screw slot 48 even when the retaining plate 50 is fixed over the second bone screw.

The retaining plate 50 also includes a set screw aperture 57 between its first and second ends. The set screw aperture 57 in the retaining plate 50 is aligned with a set screw aperture (not shown) in the base plate 20, both of which can receive a set screw (not shown) for fixing the retaining plate in place over the base plate. The set screw can be made of any suitable material well known in the art, and can be titanium or a titanium alloy. In one embodiment, the set screw is a hexagonal set screw that can be turned with a hexagonal driver. Other types of set screws can also be used, as well as any other suitable mechanism for fixing the retaining plate to the base plate. The precise mechanism by which the retaining plate is fixed to the base plate is not critical to the invention.

Any other suitable bone screw retaining means can be used in connection with the invention. For example, the bone screw retaining means can comprise multiple retaining plates that cover different bone screws. Alternatively, the bone screw retaining means can comprise one or more screws with heads that overlap at least a portion of one or more bone screws to thereby prevent the bone screws from backing out. The precise mechanism by which the bone screws are covered is not critical to the invention.

In the depicted embodiment, the base plate 20 further includes a pair of lateral tabs 60 integrally formed with the primary member 21 and extending outwardly from opposite ends of the bottom surface 26 of the primary member to form, together with the primary member, a unitary substantially U-shaped structure. In use, the lateral tabs 60 extend around the bone graft 12 to prevent lateral shift of the graft and control subsidence of adjacent vertebrae as they set during healing. The lateral tabs 60 may be made of any suitable material, and can be made of the same material as the base plate 20. Each tab 60 includes a generally-pointed nub 66 that extends outwardly from its corresponding tab. The function of the nubs 66 is described further below.

In use, the base plate 20 is placed directly on the bone graft 12 such that the bottom surface 26 contacts the bone graft and the side wall 32 engages a side 70 of the first vertebral body 14, as shown in FIGS. 1 and 3. The secondary member 22 engages a corner or the lip osteophyte 74 of the second vertebral body 16. Two first bone screws 24 are inserted into the first bone screw holes 42 in the base plate 20 to anchor the base plate to the first vertebral body 14. The first bone screws 24 received by the first bone screw holes 42 penetrate the vertebral body 14 in an angled alignment. The axial angle of the first bone screw holes 42 determines the angle at which the first bone screws 24 will be introduced through the first vertebral body 14.

The secondary member 22 is secured to the second vertebral body 16 by the second bone screw 25 being received through the bone screw slot 48. The second bone screw 25 received by the bone screw slot 48 penetrates the second vertebral body 16 through the lip osteophyte 74. It is possible to anchor the base plate 20 to the vertebral body 16 through the lip osteophyte because the lip osteophyte is structurally the strongest part of the bone. The angle of the secondary member 22 relative to the primary member 21 and the angle through which the bone screw slot 48 extends through the second member determine the angle at which the second bone screw 25 will be inserted in the second vertebral body 16.

To provide an enhanced fit, a few millimeters of bone can be trimmed or otherwise removed from the lip osteophyte 74 of the second vertebral body 16 at an angle corresponding to the angle of the secondary member 22. The trimmed surface provides a substantially flat surface for anchoring the second bone screw 25 into the lip osteophyte 74 of the second vertebral body 16.

The angles of the bone screws 24 and 25 relative to the bone surfaces of the vertebral bodies 14 and 16 are particularly important. As noted above, the lip osteophyte is the strongest part of the bone, and thus angling the bone screws through the lip osteophyte increases the ability of the base plate 20 to stay anchored to the vertebral bodies. Moreover, by being angled, each bone screw 24 or 25 is positioned along the angle of rotation of the corresponding vertebral body as well as the angle of settling of the vertebral body. This places each screw in a protected position against motion of the spinal column. As a result, significant sheer forces are not exerted on the screws as the vertebral bodies rotate and settle.

As is generally known in the art, a drilling tool may be used to drill holes in the bone to "tap" or prep the bone for receiving the bone screws 24 and 25. If desired before drilling, a tack tool, a tool having an elongated stem and a removable sharp tack at its distal end, may be used to create a starter hole in the bone to facilitate drilling. After drilling, a tapping tool may be used to tap the drilled holes. Following tapping, the bone screws 24 and 25 are screwed into the drilled and tapped holes through the bone screw holes 42 and the bone screw slot 48 of the base plate 20.

Once the bone screws 24 and 25 are inserted into the bone screw holes 42 and the bone screw slot 48, the retaining plate 50 is placed over the base plate and fixed in place to prevent the screws from "backing out" of the screw holes. The second bone screw 25 that extends through the bone screw slot 48 is nonetheless permitted to slide along the length of the slot, even when the retaining plate 50 is secured in place. Thus, the second bone screw 25 and the bone screw slot 48 cooperate to control any lateral or rotary movement of one vertebral body relative to an adjacent vertebral body during "settling" of the bone. Further, the angled orientation of the secondary member 22 provides the base plate 20 with resilient properties, for example, enabling the base plate "flex" when one vertebra is rotated relative to an adjacent vertebra.

As noted above, all of the bone screws 24 and 25 are possibly permitted to toggle, or pivot, even after the retaining plate 50 is fixed over the base plate 20. The ability of the screws to toggle permits the system 10 to migrate and self-center after it has been implanted.

If the base plate 20 includes lateral tabs 60 with nubs 66, the nubs will also share in the weight-bearing during settling of the vertebral bodies. Specifically, as the vertebral bodies move toward each other during settling, the pointed nubs 66 will contact and slowly enter the second vertebral body 16 to a limited extent. This contact can help in controlling the rate of settling.

In the alternative, relatively smaller (shorter and/or smaller in diameter) bone screws may be used. Because the bone screws penetrate the lip osteophyte, which is structurally the strongest portion of the bone, shorter bone screws may be used to anchor the base plate to the bone. Moreover, because the screws are positioned along the angle of rotation of the corresponding vertebral body as well as the angle of settling of the vertebral body, as discussed above, significant sheer forces are not exerted on the screws as the vertebral bodies rotate and settle, thereby minimizing the diameter of screw needed.

The present invention provides an additional benefit of providing a vertebral support device having a "low profile." Namely, the base plate of the present invention is specially designed to have an outer periphery that coincides with or generally matches the outer diameter of the cortex. The top surface of the base sits at, and possibly below, the top surface of the vertebral bodies. As such, the bone plate system of the present invention does not have any parts that would significantly interfere with or irritate the trachea, esophagus, and/or other sensory nerves of the user.

Another advantage of the present bone plate system is that it is stackable. Frequently after a bone graft is inserted and a bone plate joined to the surrounding vertebral bodies, for example, C4 and C5, an adjacent disk, for example, between C5 and C6, subsequently deteriorates. With traditional bone plates, it would be necessary to remove the plate from C5 before attaching a second bone plate to C5 and C6 because each plate covers a significant surface of the vertebral body. To remove a bone plate, it is necessary cut through scar tissue, which can have a negative impact on the patient. In contrast, the bone plate systems of the present invention cover an insignificant portion of the top surfaces of the vertebral bodies to which it is attached, instead being located primarily between the vertebral bodies. As a result, multiple bone plate systems can be introduced over adjacent bone grafts (i.e., between a common vertebral body) so that two bone plate systems are attached to a common vertebral body without the bone plate systems contacting one another. Thus, subsequent procedures where new bone grafts are to be inserted do not require the removal of a pre-existing bone plate prior to introduction of a new bone plate. The depicted systems where the bone screws are provided in a generally triangular arrangement further enhances the stacking ability of the bone plate systems of the invention.

It is presently considered to provide a kit having base plates of different sizes, bone screws of differing lengths and retaining plates complementary to the base plates. The kit may further comprise a tack tool, a drilling tool, tapping tool and/or one or more screw driving tools.

Figure 8:
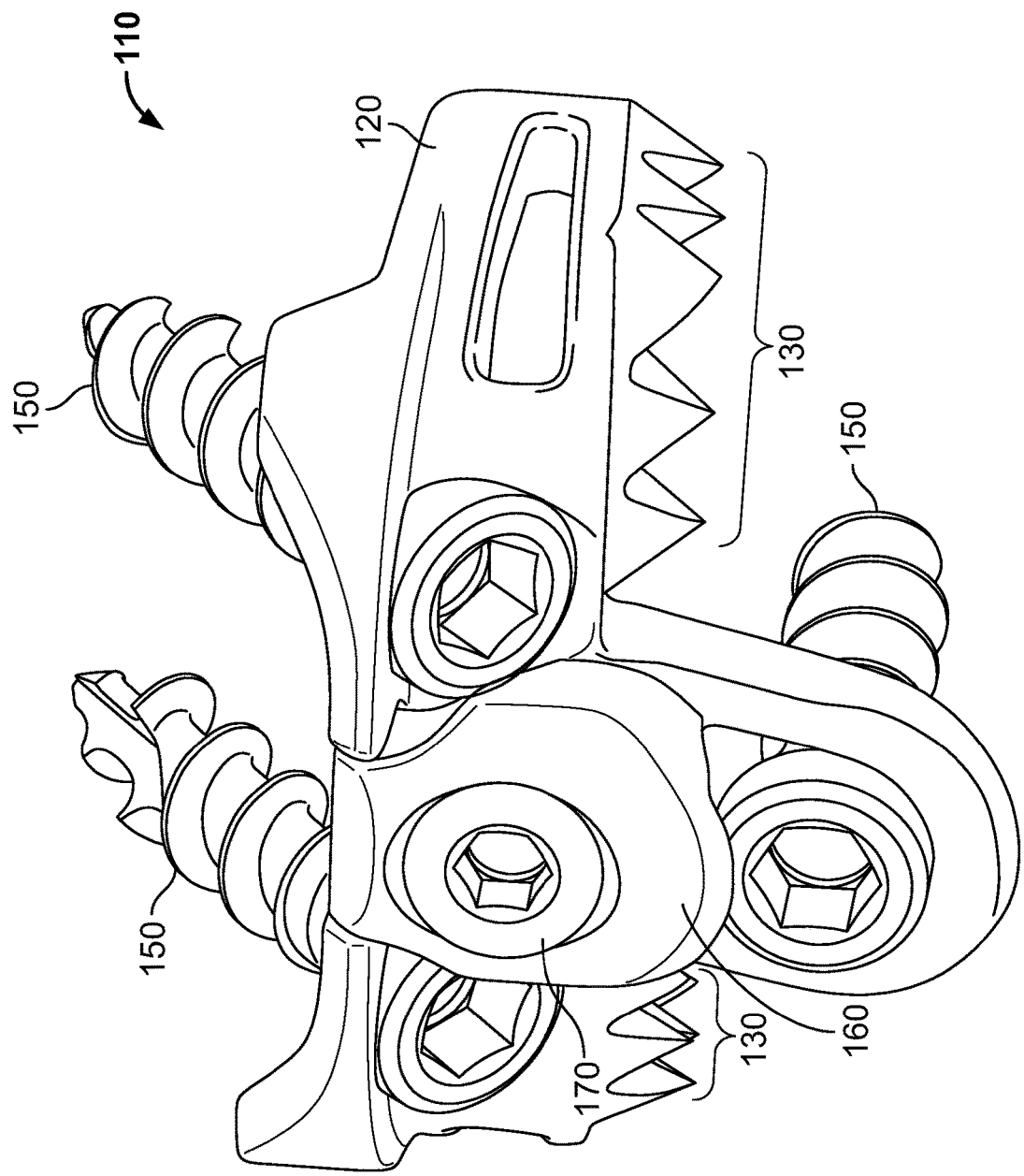
FIG. 8 is a front perspective view of an interbody device in accordance with an aspect of the present invention.
Figure 9:
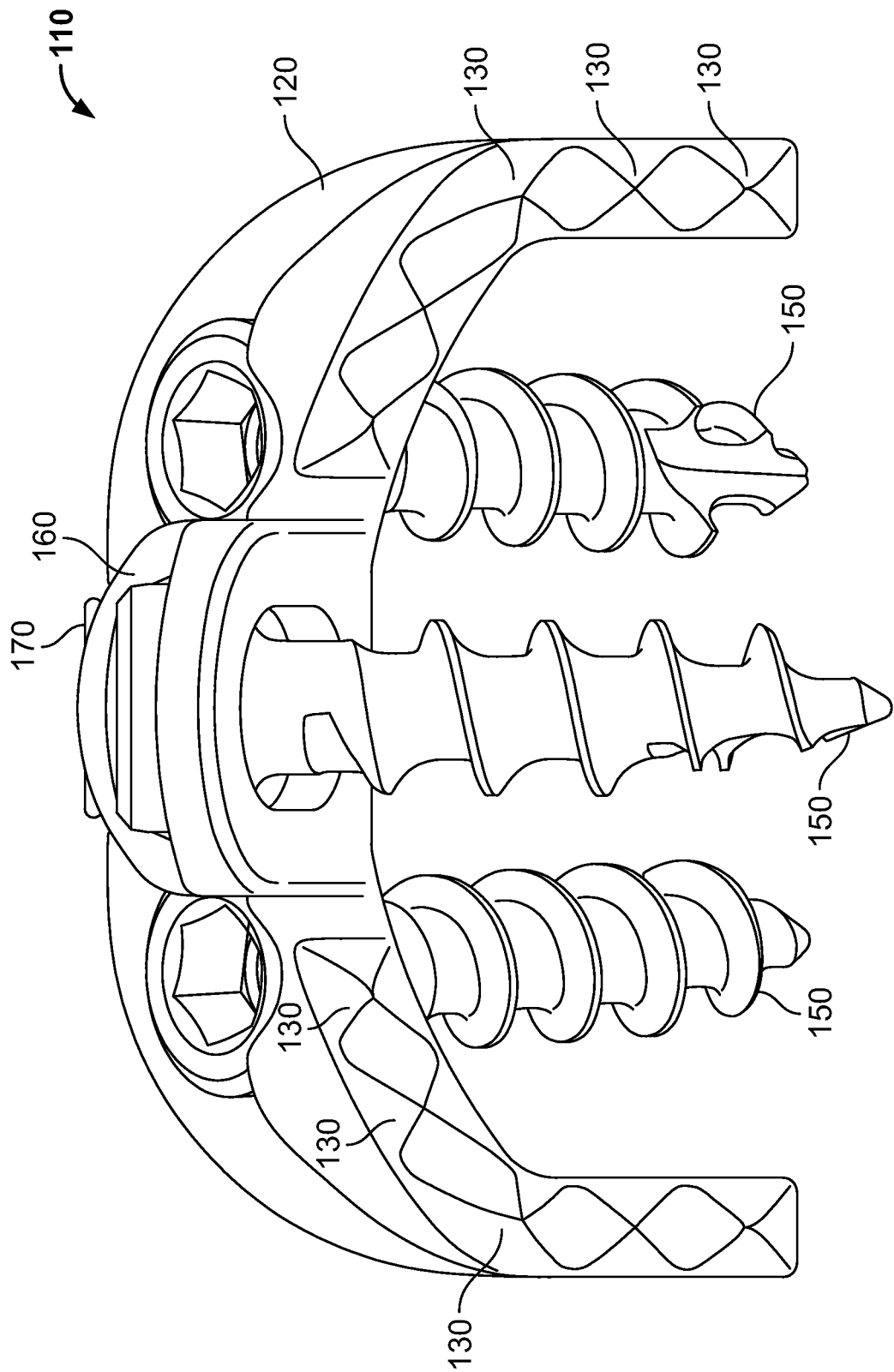
FIG. 9 is a bottom perspective view of an interbody device in accordance with an aspect of the present invention.
Figure 10:
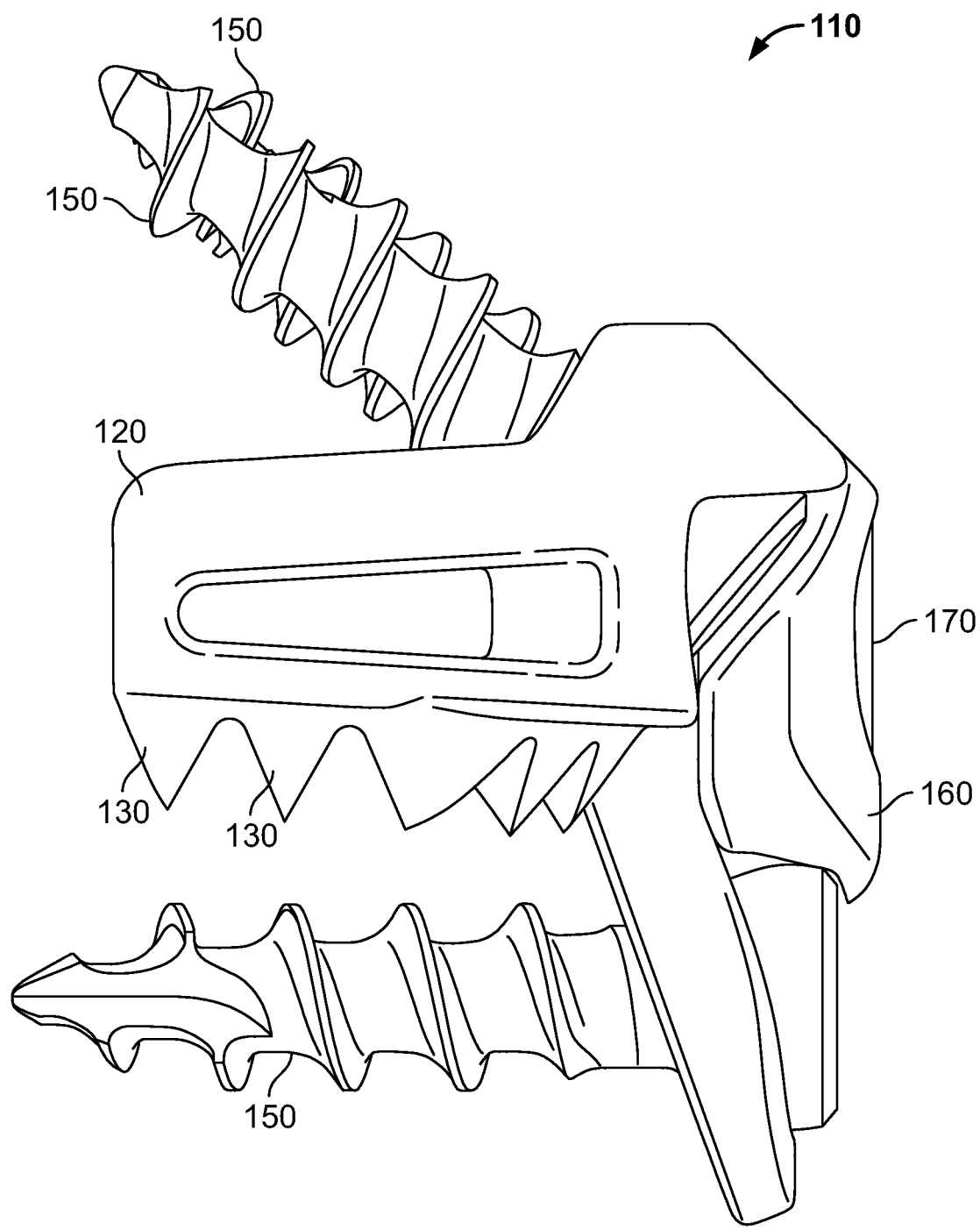
FIG. 10 is a side view of an interbody device in accordance with an aspect of the present invention.

Referring to FIGS. 8-10, an example of an interbody device 110 is illustrated in accordance with an aspect of the present invention. The interbody device 110 is configured to fix and secure two bone bodies. As used herein, the phrase "bone bodies" is intended to include individual bones as well as fragments or portions of bones. More specifically, and as will be described in further detail below, the interbody device can fix and secure adjacent vertebrae that have had cartilaginous disc between the vertebrae replaced with a graft of bone tissue or some other material that promotes the fusion of the vertebrae. It is to be appreciated that one aspect that is addressed by the present invention is load sharing with a graft. The configuration of the interbody device 110 includes a base member 120 having a plurality of protrusions or interface members 130 extending from a portion of the base member 120. As will be explained in further detail below, the interface members 130 are configured to contact at least one surface of at least one bone body to provide subsidence control for the interbody device 110. Controlled subsidence relates to resistance to subsidence and total amount of subsidence. The base member 120 of the interbody device 110 also includes a plurality of apertures, each of which is configured to receive a corresponding bone fastener or screw 150 therethrough.

The interbody device 110 also includes a restraining means for restricting movement of one or more bone fasteners 150 coupled to the base member 120. The restraining means can be any means for securely covering at least a part of each of the bone fasteners 150 so that the bone fasteners 150 cannot back out from the bone bodies once screwed in through the base member 120 of the device 110. In the depicted embodiment, the bone screw restraining means comprises a restraining plate 160 and a restraining plate fixing means 170.

Turning now to FIGS. 11-14, the base member 120 of the interbody device 110 is illustrated in greater detail. The base member 120 is generally u-shaped with a first end 180 at the open end of the u-shape and a second end 190 at the closed end of the u-shape (see FIGS. 13 and 14). The second end 190 includes a primary member 200 and a secondary member 210, which extends from and is angled relative to the primary member 200. First and second legs 220, 230 of the u-shaped base member 120 are integrally formed with the primary member 200. In use, the first and second legs 220, 230 extend around a bone graft to mitigate lateral shift of the graft and control subsidence of adjacent vertebrae as they set during fusion. Apertures 187 may be provided as shown.

Subsidence is further controlled by the presence of the interface members 130 that extend from a portion of the base member 120. The interface members 130, as depicted in the present embodiment, can include a plurality of teeth extending from bottom surfaces of the primary member 200, the first leg 220, and the second leg 230. Accordingly, when coupled with the bone bodies, the interface members 130 extend from the base member 120 in a direction that is aligned with an elongate direction of the spine. The interface members 130 thus, are configured to provide a progressive penetration into the bone body over a period of time in a direction aligned with the elongate direction of the spine. It is to be appreciated, however, that any suitable configuration of interface members can be provided at any suitable location on the base member that interfaces with a surface of the bone body.

The interface members can include teeth, knife-edges, spikes, posts, pegs, and the like, including any combination thereof. The configuration of the interface members includes interlocking external features that impact a subsidence profile, which is a relationship between an applied load and an amount of settling the interbody device 110 experiences when secured to the bone bodies. Or in other words, the subsidence profile is a relationship between a depth of subsidence of the interface members and a force required to achieve the depth of subsidence. When first implanted, the interface members 130 will rest on top of the bone surface. When load is applied to the interbody device 110, the interface members 130 will penetrate, or subside, into the bone in a controlled manner. The interface members can readily dig into the bone initially and then slow down as more of the tooth cross section embeds. Different interface member configurations provide different controlled subsidence profiles. The density of the bone body also impacts the subsidence profile. For example, in a lower density bone body representation, such as 15 pcf foam, the interface members can penetrate the bone body by about 1 mm using between about 50-100 N of force and by about 2 mm using between about 150-250 N of force. In a medium density bone body, such as 20 pcf, the interface members can penetrate the bone body by about 1 mm using between about 100-200 N of force and by about 2 mm using between about 400-900 N of force. In a higher density bone body, such as 40 pcf, the interface members can penetrate the bone body by about 1 mm using between about 100-500 N of force and by about 2 mm using between about 1000-2250 N of force. The amount of force needed for displacement and the rate of penetration of the interface members into the bone body depends, in part, upon the configuration of the interface members. It should be noted that all of the pcf densities refer to polyurethane foam (which is referenced to ASTM standards) that is used as a bone analog for test purposes. The tests were also conducted using a straight test "blade" that was 40 mm long, not an actual implant.

Figure 11:
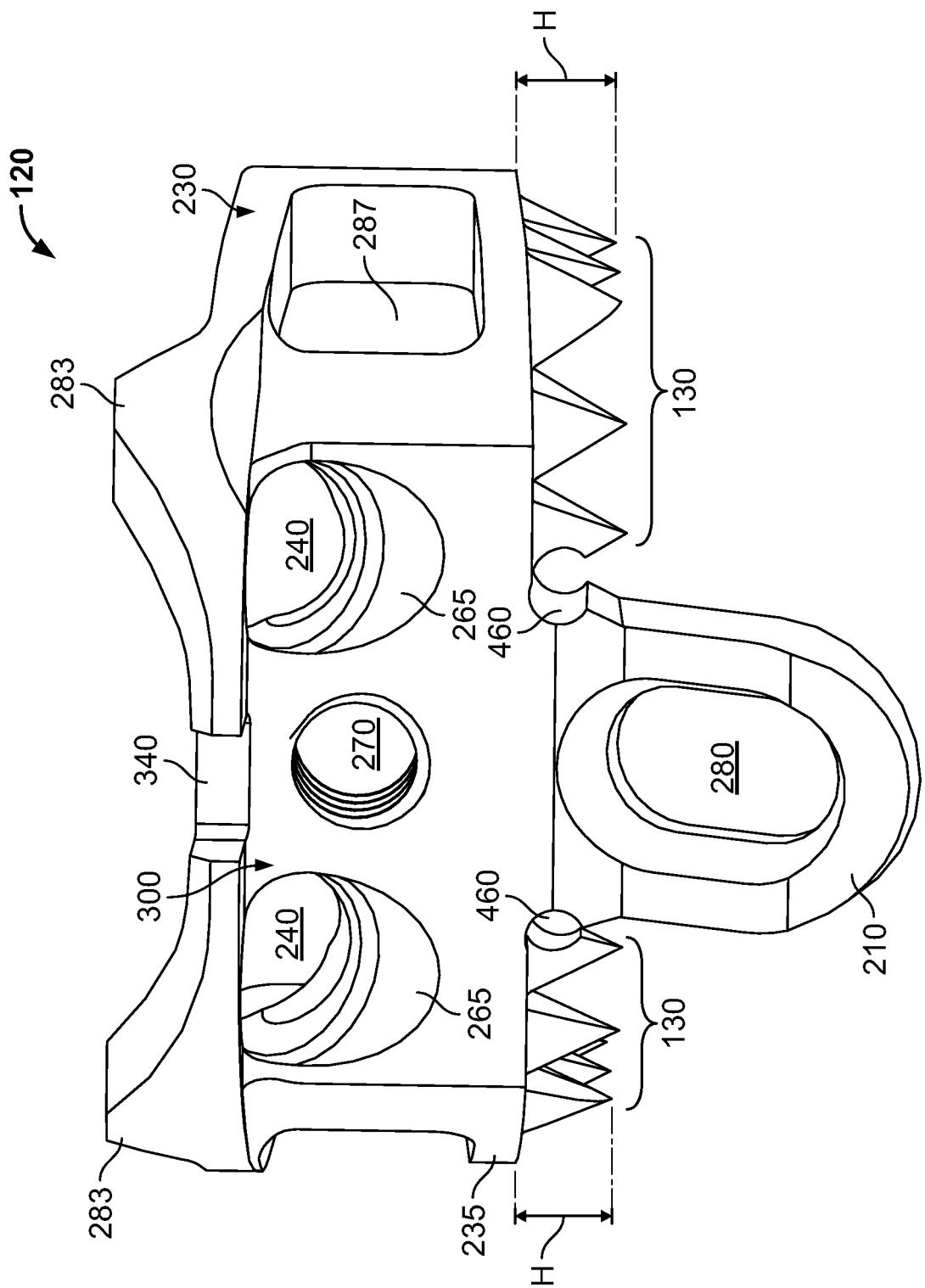
FIG. 11 is a front perspective view of a base member of an interbody device in accordance with an aspect of the present invention.
Figure 26:
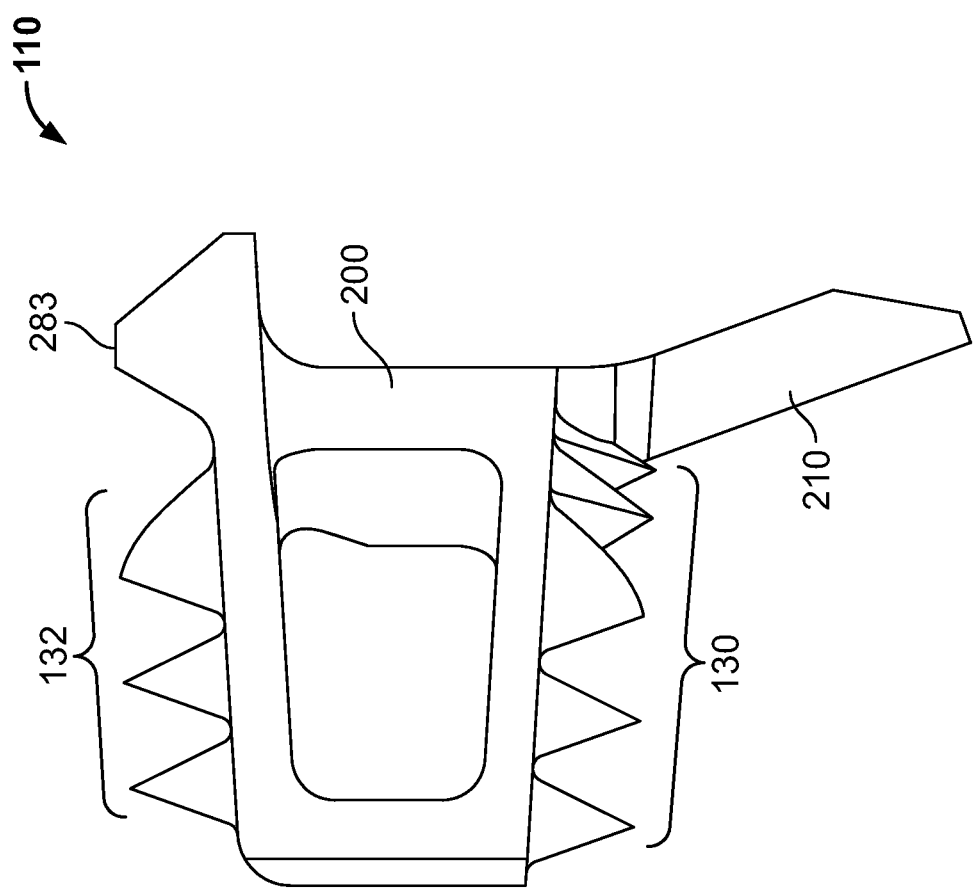
FIG. 26 is a side view of a base member of an interbody device in accordance with an aspect of the present invention.

The height (H) of the interface members 130 determines a depth of penetration into the bone body (see FIG. 11). Generally, when the interbody device 110 has subsided to a point where the interface members are fully embedded in the bone, the applied load will be distributed across the entire surface of the interbody device 110 and subsidence resistance will greatly increase. Typically, the screw will be at the end of the slot. Thus, the height (H) of the interface members can control an amount of subsidence that the interbody device 110 will permit. The interface members 130 can be of any height or combination of heights. Thus, if a plurality of interface members 130 extend from a surface of the base member, each interface member 130 can be of equal heights or substantially taller or shorter than other interface members. FIG. 26, as described in more detail below, illustrates that the interface members 130, 132 can extend from the top or bottom surfaces of the base member. The interface members 130, 132 can be of equal height or substantially dissimilar heights depending on the amount of subsidence resistance that is desired.

In addition to the height (H) of the interface members 130, the shape of the interface members 130 also affects subsidence of the interbody device 110. The shape of the interface members 130 controls a shape of the subsidence profile; and therefore, affects the load shared with the graft material. For instance, if the interface members 130 were limited to a few sharply pointed spikes, subsidence would occur substantially immediately and the interbody device 110 would rapidly seat in the bone to the fullest extent under low force. In this instance, any graft material would be immediately and highly loaded. Such immediate subsidence is not desirable because the joint space could narrow and cause nerve root or spinal cord compression. Also, the graft would be overloaded, inhibiting fusion. However, some subsidence is needed to load the graft and ensure fusion. Accordingly, by configuring the interface members 130 to have a broadly shaped portion, the interbody device 110 has increased resistance to subsidence as the interface members 130 penetrate into the bone body; and the graft material is gradually loaded as the device subsides. For instance, turning to FIG. 14, each tooth 130 is shaped with a substantially broad base, the base being defined by a length (L) and width (W) of each tooth. The substantially broad base of each tooth facilitates controlled subsidence of the interbody device 110. For instance, the as the tooth becomes wider in cross section, the penetration of the tooth into the bone body will become slower.

Once the interface members 130 have fully penetrated the bone, the surface area of the base member 120 is of an area large enough to resist further subsidence of the interbody device 110. To increase subsidence resistance, at an interface between the a plurality of teeth 130 and the bottom surfaces of the primary member 200 and the first and second legs 220, 230, a shelf-like area 235 is created. The shelf-like area 235 provides an extended surface area to contact the bone material, thereby increasing subsidence resistance once the interface members 130 have fully subsided. As mentioned, the screw will typically be at the end of the slot.

Figure 12:
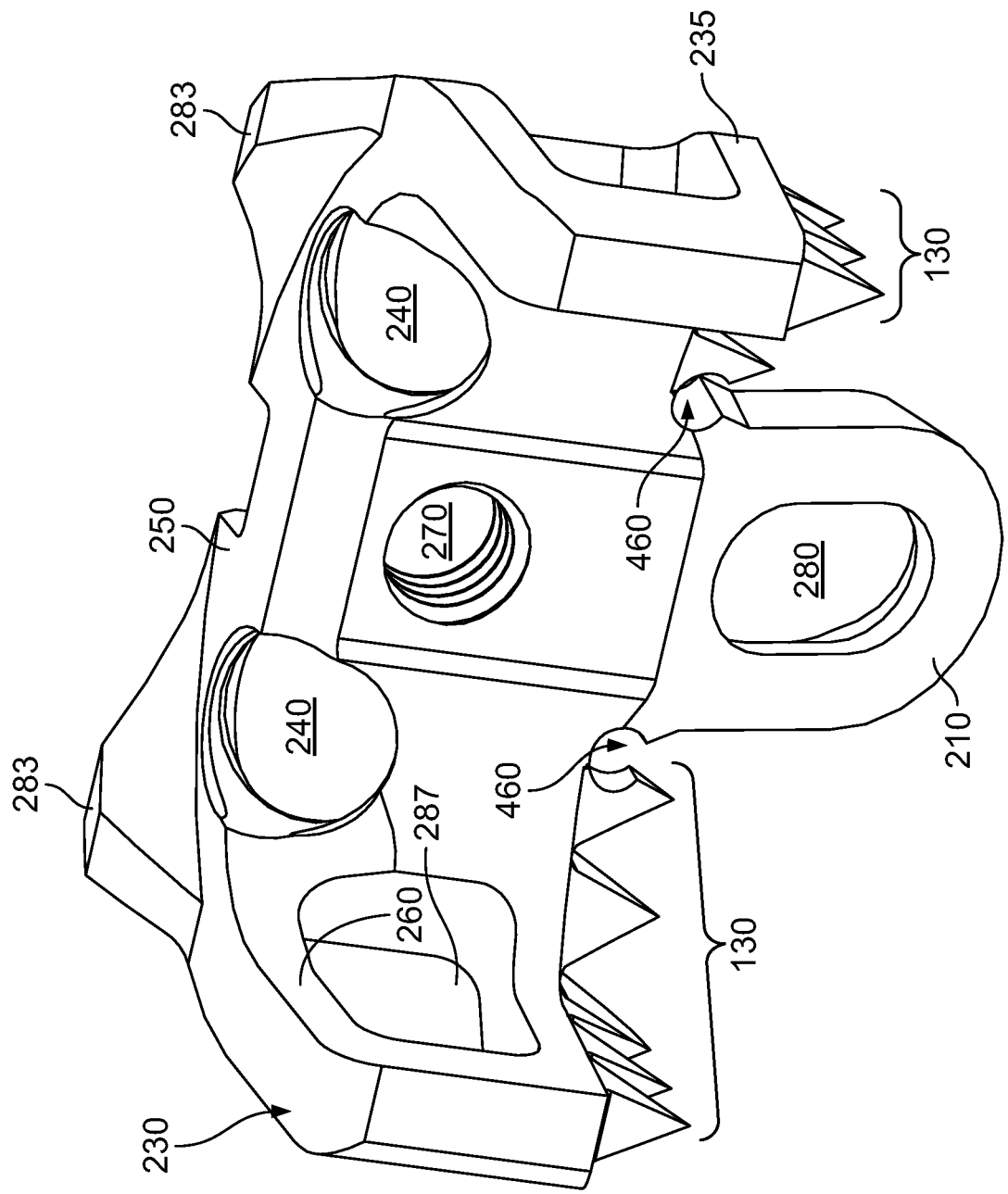
FIG. 12 is a back perspective view of a base member of an interbody device in accordance with an aspect of the present invention.
Figure 13:
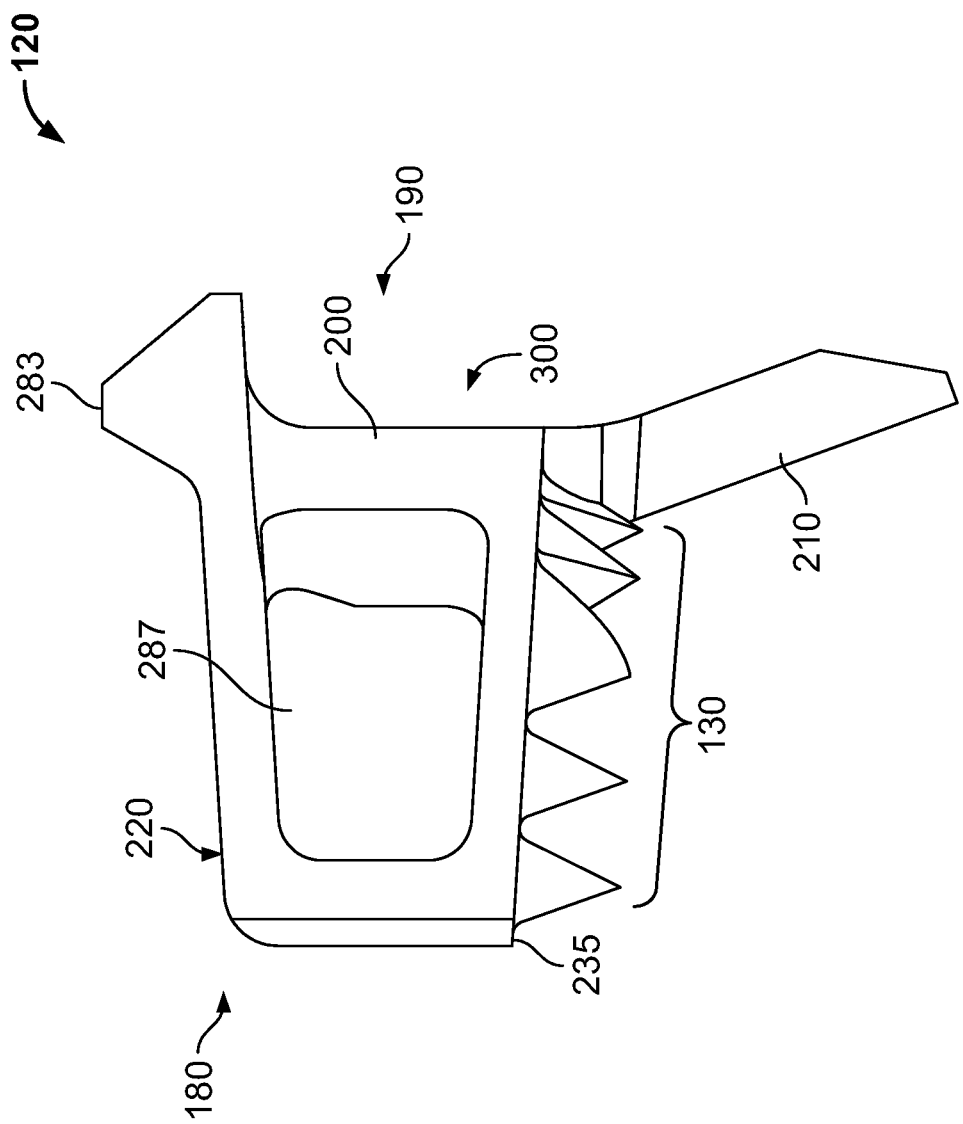
FIG. 13 is a side view of a base member of an interbody device in accordance with an aspect of the present invention.
Figure 14:
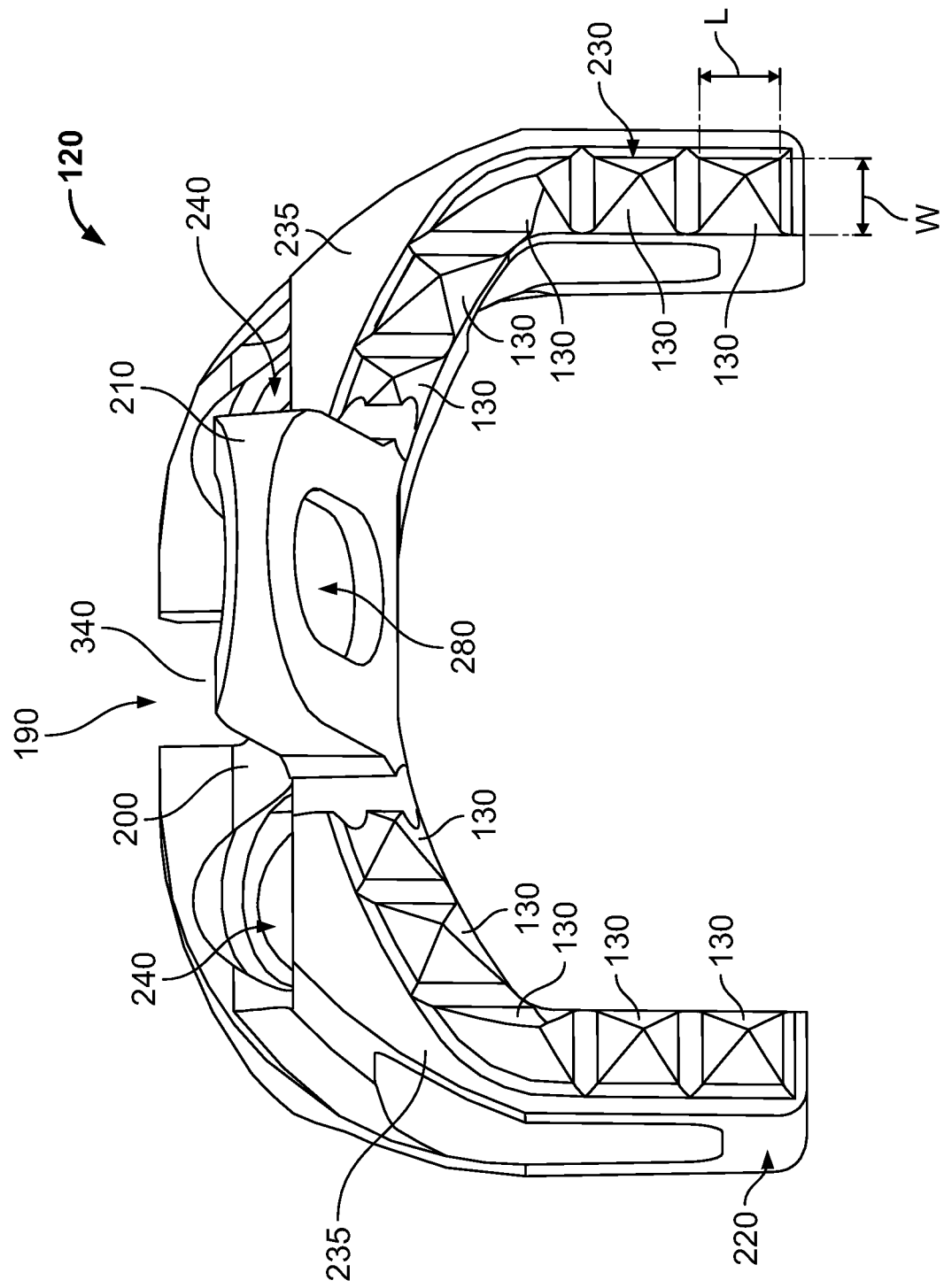
FIG. 14 is a bottom perspective view of a base member of an interbody device in accordance with an aspect of the present invention.

Turning back to the primary and secondary members 200,210 of the base member 120, the secondary member 210 has a front surface that is generally continuous with a front surface of the primary member 200, as illustrated in FIG. 11 and a back surface that is generally continuous with a back surface of the primary member 200, as illustrated in FIG. 12. FIG. 13 illustrates the angular relationship between the primary and secondary members 200, 210. The primary member 200 and secondary member 210 are arranged relative to each other so that their front surfaces form an angle greater than 90° and less than 180°, specifically from 110° to about 160°. As will become apparent, the angle at which the primary and secondary members 200, 210 are joined is provided so that bone screws can be introduced through the base member 120 at desired angles, as discussed further below. Accordingly, the base member 120 can be designed in any other manner that permits the bone screws to be introduced therethrough at the desired angles.

The primary member 200 includes at least one, and possibly two (as shown in the depicted embodiment) first bone screw holes 240 extending therethrough, each configured to receive a corresponding bone screw. The first bone screw holes 240 in the primary member 210 are configured such that bone screws extend through the holes 240 at an angle, as illustrated in FIG. 10. For example, the first bone screw holes 240 can extend through a corner that joins a top surface 250 of the base member 120 to a back surface 260 of the base member 120, as best shown in FIG. 12. As a result, each bone screw extending through the first bone screw holes 240 can enter the bone body at an angle, as discussed further below. Each of the first bone screw holes 240 is sufficiently large to allow a portion of a respective bone screw to pass therethrough but not large enough to allow a retaining portion of the bone screw through, such as the head of the bone screw. Further, each of the first bone screw holes 240 has a seat 265 on which the retaining portion of a respective bone screw rests. Each seat 265 has a generally concave spherical shape and the surface of the retaining portion of the bone fastener in contact with the seat 265 has a complementary convex spherical configuration. Consequently, the bone screws are free to pivot on the seats 265. The primary member 200 also includes a threaded hole 270 for receiving the restraining member fastener 170.

The secondary member 210 includes a second bone screw hole 280 in the form of an elongated slot for receiving a bone screw. The bone screw is introduced into the second bone screw hole 280 and into a second bone body. The second bone screw hole 280 is configured such that a bone screw can slide and rotate within the slot relative to the base member 120 and generally toward the primary member 200. Thus, in use, as two adjacent bone bodies, to which the base member 120 is fixed, collapse or settle and move toward each other, the bone screw contained within the second bone screw hole 280 will slide within the slot and move with the bone body into which it extends in a direction toward the primary member 200 and the other bone body.

At least one and possibly two projections 283 extend upwardly from the top surface 250 of the base member 120. The projections 283 contact a surface of the bone bodies to provide a stop when inserting the base member 120 between the bone bodies. The base member 120 also includes holes 287 provided through each of the first and second legs 220, 230. The holes 287 facilitate visualization of the fusion mass on x-rays and bone growth therethrough when the interbody device 110 is positioned between two bone bodies.

The base member 120 may be made of any suitable material, and can be made from titanium or a titanium alloy. The thickness of the base member 120 is not critical, and possibly ranges from about 1 mm to about 2 mm, and more specifically is about 1.6 mm. The height of the base member 120 will depend on the needs of the particular patient.

Figure 15:
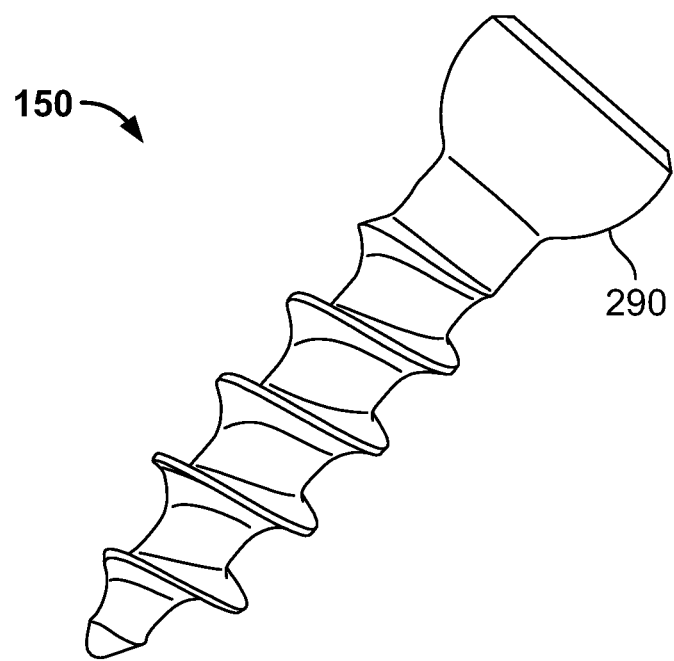
FIG. 15 is a perspective view of a bone screw of an interbody device in accordance with an aspect of the present invention.

Turning now to FIG. 15, the bone fastener 150 is illustrated in further detail in accordance with an aspect of the present invention. The bone fastener 150 can comprise a bone screw, a plurality of which is used for securing the interbody device 110 to the bone bodies. The bone fasteners 150 can be made of any suitable material, and are possibly made of the same material as the base member 120, such as titanium or a titanium alloy. The bone fasteners 150 can all have the same shape, such as that shown in FIGS. 8-10. In the depicted example, the bone fasteners each have a radiused head 290. As used herein, the term "radiused head" means that the lower portion of the bone screw head, i.e., the portion that is nearest the shank, is generally rounded, to thereby permit the bone screws to toggle within their respective holes 240 and 280. The bone fasteners 150 can have any other suitable shape that permits them to cooperate with the first and second bone screw holes 240 and 280 or the elongated slots of FIGS. 24 through 29.

The bone fasteners 150 can be undersized to permit the bone fastener to slide in a bone screw hole. For instance, the bone fastener may be positioned in a bone body such that the retaining portion, such as the head, does not rest on the seat of the hole and the portion of the bone fastener extending into a bone body is not fully embedded. In this case, it is desirable that the portion of the bone fastener extending into a bone body is substantially small. Reducing the non-embedded portion of the bone screw tends to ensure that the retaining portion of the bone fastener does not protrude outward from the hole in a manner that renders it difficult to position a retaining means over the bone fastener. To permit the bone fastener 150 to slide in the hole, the diameter of the portion extending into a bone body is substantially less than the diameter of the hole. The bone fastener 150 can be positioned at one edge of the hole so that the bone fastener may slide within the diameter of the hole until it becomes in contact with the opposite edge of the hole. The hole in this case functions as an elongated slot as described with regard to FIGS. 24 through 29. In this regard, the hole has a small elongation length that allows the bone fastener to slide. Thus, the length of travel is controlled by the difference of the respective diameters of the hole and the portion of the screw extending into a bone body. In other words, the more undersized the portion of the bone fastener that extends into a bone body, the more slide length that will be available.

Figure 16:
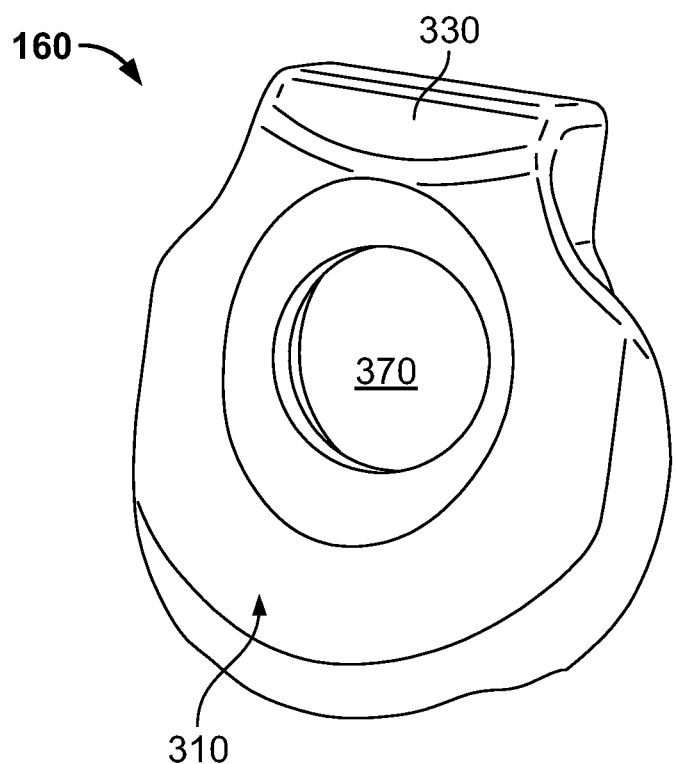
FIG. 16 is a front perspective view of a restraining member of an interbody device in accordance with an aspect of the present invention.
Figure 17:
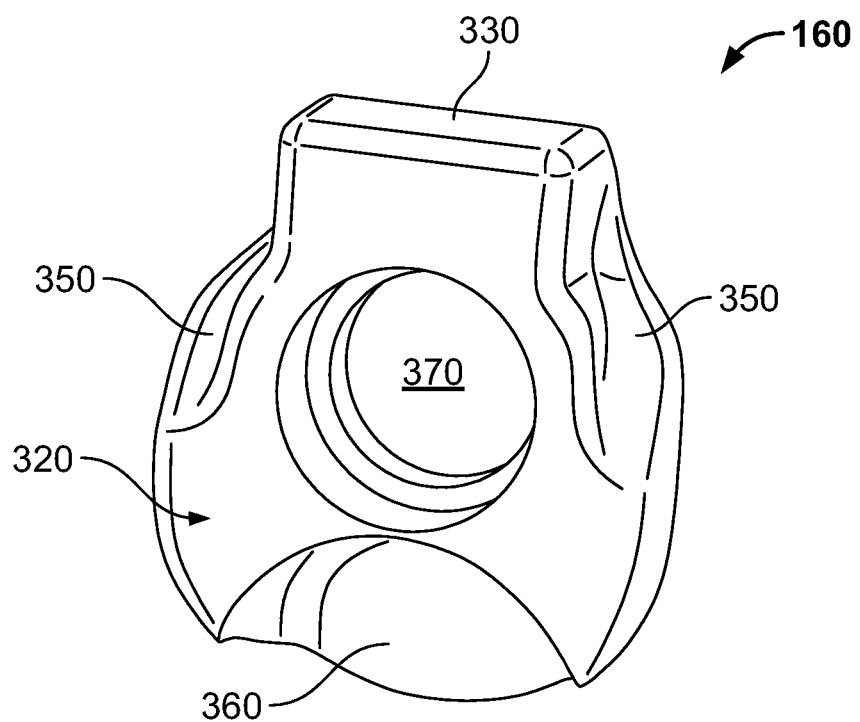
FIG. 17 is a back perspective view of a restraining member of an interbody device in accordance with an aspect of the present invention.

The bone fasteners are secured to the base member 120 via restraining means. As stated above, the restraining means can include a restraining plate 160, an example of which is illustrated in FIGS. 16 and 17 in accordance with an aspect of the present invention. The restraining plate 160 is configured to correspond with a recessed region 300 of the base member 120 of the interbody device 110 (see FIGS. 11 and 13). More specifically, the restraining plate 160 includes a generally rounded front side 310 and a generally flat back side 320. The restraining plate 160 has a flange 330 formed in a top portion of the plate, the flange 330 being configured to fit within a corresponding groove 340 formed in the base member 120. The use of the recessed region 300 and the groove 340 in the base member 120 facilitates proper positioning of the restraining plate 160 on the base member 120. The thickness of the restraining plate 160 is not critical, but should generally be as thin as possible. Some example thicknesses are possibly in the range from about 0.5 mm to about 2 mm, more specifically from about 1 mm to about 1.5 mm.

Turning to FIG. 17, the restraining plate 160 includes a plurality of notches formed along the edges of its back surface 320. The notches include at least one generally rounded notch 350, possibly two, each of the generally rounded notches 350 configured to correspond with one of the bone fasteners/screws 150. When the restraining plate 160 is fixed in place over the base member 120, the generally rounded notches 350 each cover a portion of a corresponding one of the bone fasteners 150. The notches 350 are generally rounded so as to permit the bone fasteners 150 to toggle within the first bone screw holes 140. The restraining plate 160 can also include a substantially U-shaped notch 360, which is curved outwardly towards the edge of the restraining plate 160. When the restraining plate 160 is fixed in place over the base member 120, the top of the bone fastener 150 positioned within the second bone screw hole 280 sits within the U-shaped notch 360. Thus, a top of the bone fastener 150 is covered by the top surface of the restraining plate 160. With this design, the bone fastener 150 positioned within the second bone screw hole 280 is permitted to slide and toggle within the slot even when the restraining plate 160 is fixed over the bone fasteners 150.

The restraining plate 160 also includes an aperture 370 formed therethrough. The aperture 370 in the restraining plate 160 is aligned with a hole 270 in the primary member 210 of the base member 120, both of which can receive a restraining member fastener 170 for fixing the restraining plate 160 in place over the base member 120. The restraining member fastener 170 can be made of any suitable material well known in the art, possibly titanium or a titanium alloy. The restraining member fastener 170 can be a screw, such as a hexagonal screw that can be turned with a hexagonal driver. Other types of fasteners can also be used, as well as any other suitable mechanism for fixing the restraining plate 160 to the base member 120. In one embodiment, the mechanism does not permanently fix the restraining plate 160 to the base member 120 so that device 110 can be removed if desired. The precise mechanism by which the restraining plate 160 is fixed to the base member 120 is not critical to the invention.

In one embodiment the restraining plate 160 functions to prevent the bone fasteners/screws 150 from backing out of the bone bodies once the bone fasteners 150 are screwed in. That is, the notches 350 and the U-shaped notch 360 cover the bone fasteners 150 extending through the base member 120 such that the top surface of the restraining plate 160 does not come into contact with the bone fasteners 150. When the restraining plate 160 is fixed in place over the bone fasteners 150, the top surface of the restraining plate 160 does not interfere or contact the bone fasteners 150 as they toggle or slide in the bone screw hole 140 or slot 280. The top surface of the restraining plate 160 contacts or restricts the movement of the bone fasteners when the bone fasteners 150 back out or loosen from the bone bodies. Thus, during normal use of the implanted device 110, the restraining plate 160 does not tend to impede the movement of the bone fasteners 150.

In another embodiment, which is not shown, the restraining plate 160 can have a top surface and/or notches that contact or interface with the head of at least one bone fasteners 150. The interface between the top surface or notch of the restraining plate 160 and a corresponding bone fasteners 150 prevents the bone fasteners 150 from backing out of the bone body and tends to exert force on the bone fasteners 150 so as to control the movement of the fasteners 150 in the hole 240 or slot 280 of the base member 120. Depending on the surface dimensions of the restraining plate 160 and the shape of the bone fastener 150 head, the interface between the plate 160 and a bone screw fastener can control the amount of toggle or slide of a bone fastener 150. For example, the restraining plate 160 can include a notch configured to match the rounded head of a corresponding bone fastener 150, wherein the notch also has a stop plate or restraining surface. When the bone fastener 150 toggles in the slot of the base member 120, the head rotates along the interface with the corresponding notch in the restraining plate 160 until the head of the bone fastener 150 reaches the stop plate. In this regard, the top surface or notch of the restraining plate 160 can be designed so the interface with a bone fastener 150 can be used to control the amount of movement or resistance a bone fastener 150 is subject to in order to create resistance to movement thereof.

In yet another embodiment, which is not shown, the surface portions of the restraining plate 160 that interface with the bone fasteners 150 can be substantially angled such that the interface portions of the restraining plate 160 are flush with the top surface of the bone fastener 150 heads. That is, the surface portions of the restraining plate 160 that interface with the top surface of the bone fastener 150 heads rest flat against the heads and restrain the bone screws from toggling or rotating in the hole or slot the bone fasteners 150 extend through. In the case which the bone fastener 150 extends through a slot in the interbody device 110, the restraining plate 160 can also include a stop plate that extends from the surface of the restraining plate 160 into the slot. When the bone fastener 150 is at one end of the slot, the stop plate extending downward into the slot can prevent the bone fastener 150 from sliding along the entire elongation length of the slot. The stop plate can be positioned at any point along the elongation length of the slot so that the distance the bone fastener 150 slides in the slot can be controlled. Subsidence resistance can also be controlled in part by the positioning of the stop plate in the slot. For example, if the stop plate is positioned near the opposite end of the slot from the end where the bone fastener 150 is located, the bone fastener 150 can slide along substantially the entire elongation length of the slot and thus subsidence resistance may be decreased. On the other hand, if the stop plate is positioned near the location of the bone fastener 150 in the slot, the distance the bone fastener 150 can slide along the elongation length of the slot is decreased and subsidence resistance may be increased.

Figure 30:
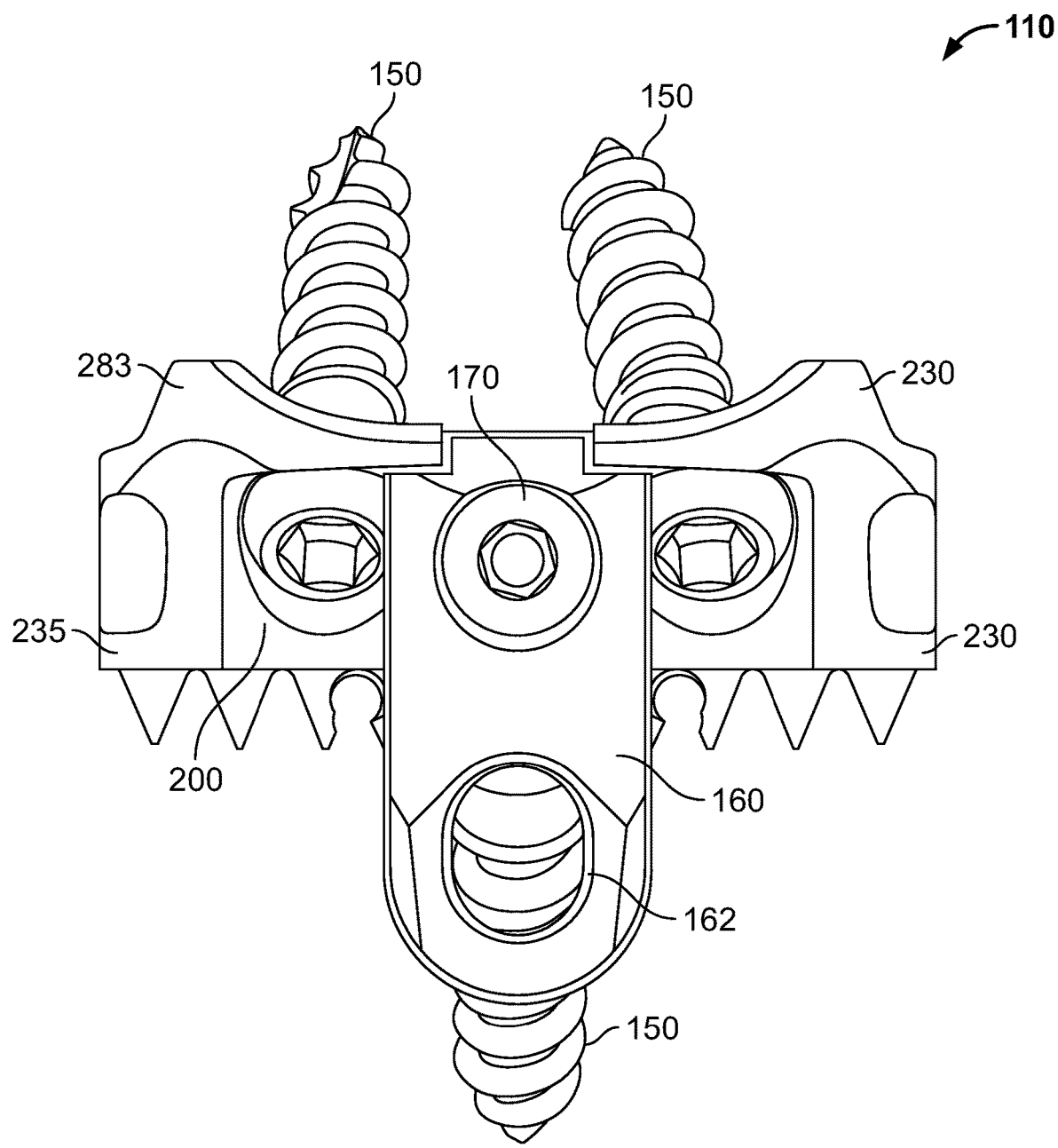
FIG. 30 is a front perspective view of an interbody device in accordance with an aspect of the present invention.
Figure 31:
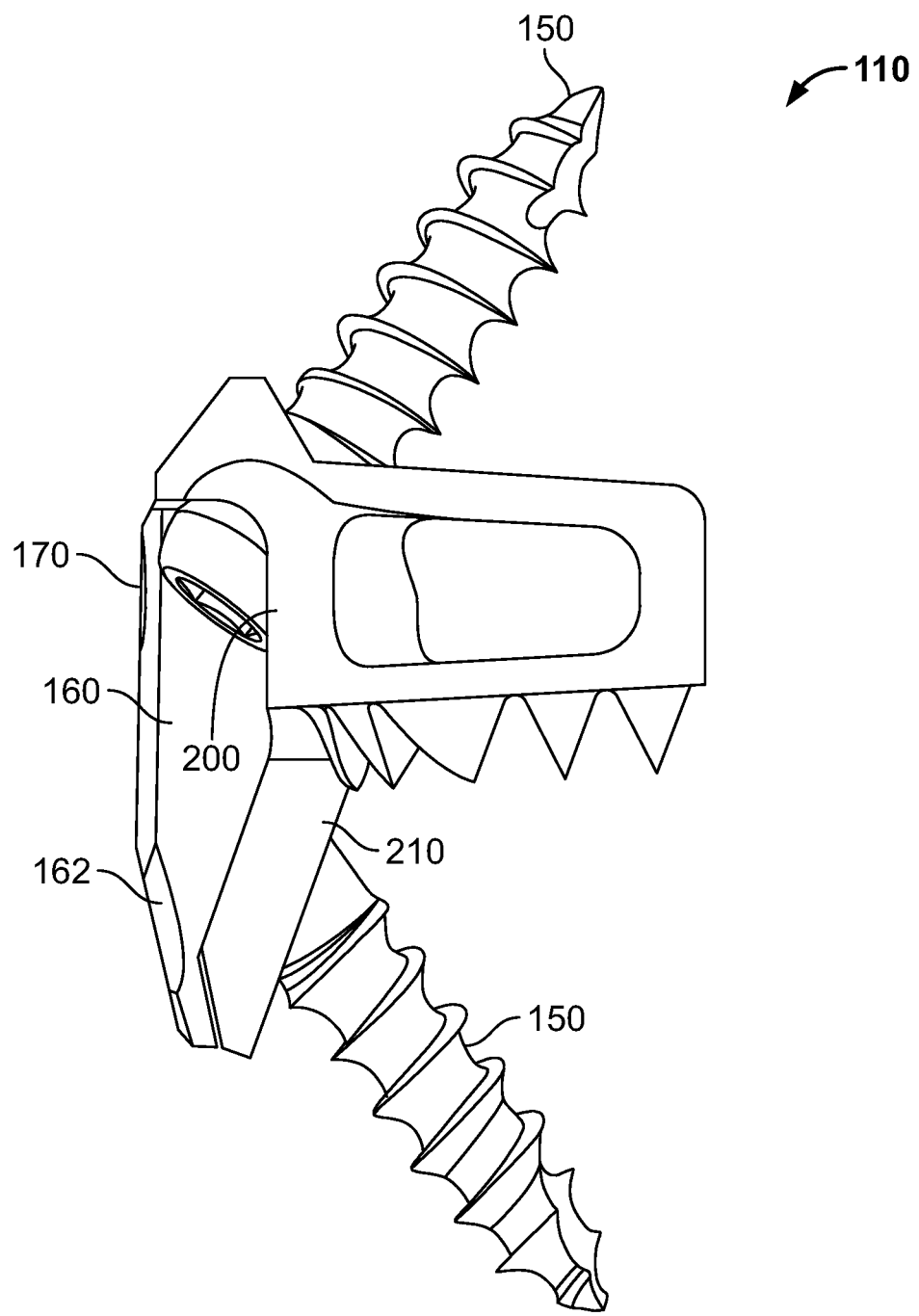
FIG. 31 is a side perspective view of another interbody device in accordance with an aspect of the present invention.

FIGS. 30 and 31 illustrate another embodiment of a restraining plate 160 that can be used with the interbody device 110. The restraining plate 160 of FIGS. 30 and 31 is attached or fixed to the interbody device 110 by means of a screw 170. The restraining plate 160 covers a portion of the bone fastener 150 heads passing through the primary member 200 and extends downward over the bone fastener 150 passing through the secondary member 210. The bone fastener 150 passing through the secondary member 210 is substantially covered by the restraining plate 160. As shown in FIG. 30, the restraining plate 160 can have an open area 162 that exposes the bone fastener 150 passing through the secondary member 210. The open area 162 of the restraining plate 160 allows the bone fastener 150 to more easily slide or toggle in the aperture it passes through. As shown in FIG. 31, the restraining plate 160 rests flush against the interbody device 110 on the surfaces of the primary member 200 and secondary member 210. The shape or contour of the restraining plate 160 allows for a custom fit with the interbody device 110 such that the front portion of the interbody device 110 is substantially flat.

Additionally, it is to be appreciated that any other suitable bone screw restraining means can be used in connection with the present invention. For example, the bone screw restraining means can comprise multiple restraining plates that cover different bone screws. Alternatively, the bone screw restraining means can comprise one or more screws with heads that overlap at least a portion of one or more bone screws to thereby prevent the bone screws from backing out.

Figure 18:
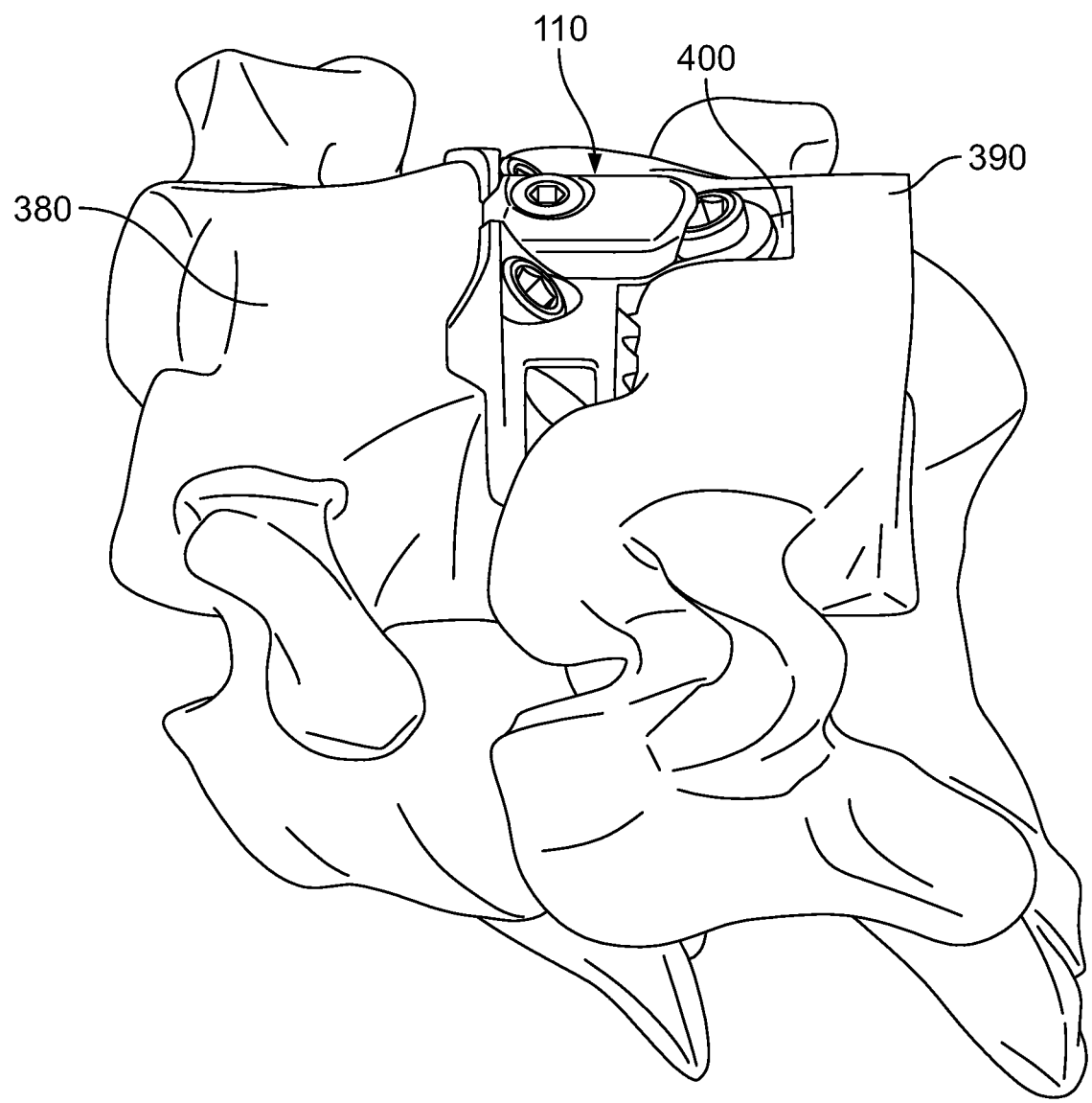
FIG. 18 is a side perspective view of an interbody device positioned between two bone bodies in accordance with an aspect of the present invention.
Figure 19:
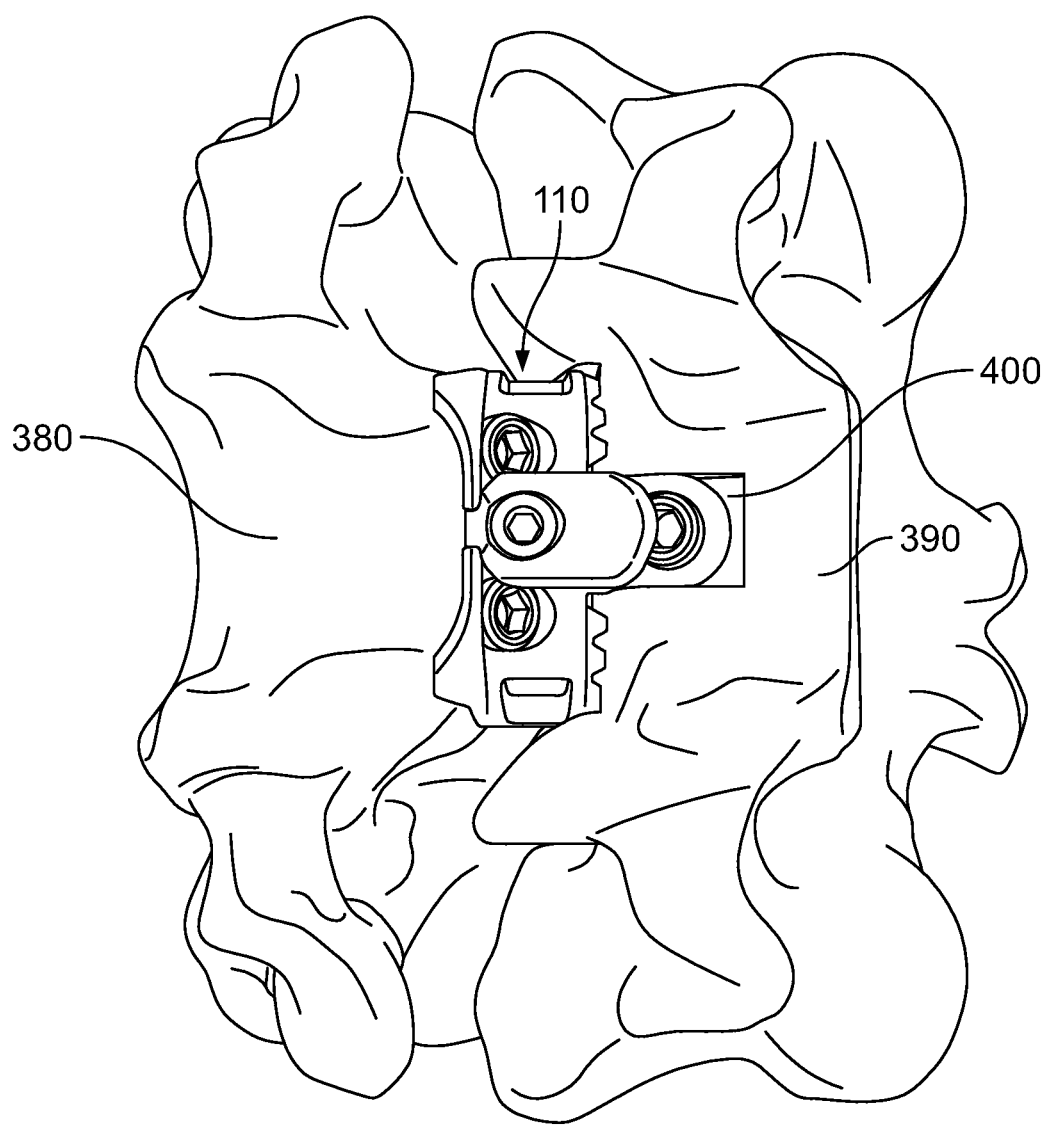
FIG. 19 is a top perspective view of an interbody device positioned between two bone bodies in accordance with an aspect of the present invention.

FIGS. 18 and 19 illustrate the interbody device 110 secured between two bone bodies 380 and 390 in accordance with an aspect of the present invention. The bone bodies 380 and 390 can be two adjacent vertebrae and the interbody device 110 can be mounted to the vertebrae with a bone graft (not shown) between the vertebrae. More specifically, the base member 120 of the device 110 is mounted to the vertebrae by attaching the bone fasteners 150, which are located in bone screw holes 240, to one of the cervical vertebrae 380 to be stabilized and the bone fastener 150, which is located in slot 280, to the other of the cervical vertebrae 390 to be stabilized. The base member 120 is positioned such that the first and second legs 220, 230 lie generally opposite the bone graft between the two vertebrae. The bone fasteners 150 are driven into the vertebrae 380, 390 sufficiently so that the convex spherical configuration of the bone fasteners 150 bear against the seats 265 of the bone screw holes 240 and secure the base member 120 against anterior surfaces of the two cervical vertebrae 380, 390. More specifically, the bone fasteners 150 provided through the bone screw holes 240 are driven through an end surface of bone body 380; and the bone fastener 150 provided through the slot 280 is driven through a top surface of bone body 390.

To provide an enhanced fit, a few millimeters of bone can be trimmed or otherwise removed from a lip osteophyte of the second vertebral body 390 at an angle corresponding to the angle of the secondary member 210 of the base member 120. The trimmed surface provides a substantially flat surface 400 for anchoring the bone fastener 150 into the lip osteophyte of the second vertebral body 390. The surface also accommodates sliding of the tab as the teeth subside into the second vertebral body 390.

The angles of the bone fasteners/screws 150 relative to the bone surfaces of the vertebral bodies 380, 390 are important. The lip osteophyte is the strongest part of the bone, and thus angling the bone fasteners/screws 150 through the lip osteophyte increases the ability of the base member 120 to stay anchored to the vertebral bodies 380, 390. Moreover, by being angled, each bone fastener 150 is positioned along an angle of rotation of a corresponding vertebral body 380, 390 as well as an angle of settling of the vertebral body 380, 390. This places each fastener/screw 150 in a protected position against motion of the spinal column. As a result, significant shear forces are not exerted on the screws 150 as the vertebral bodies 380, 390 rotate and settle.

Figure 20:
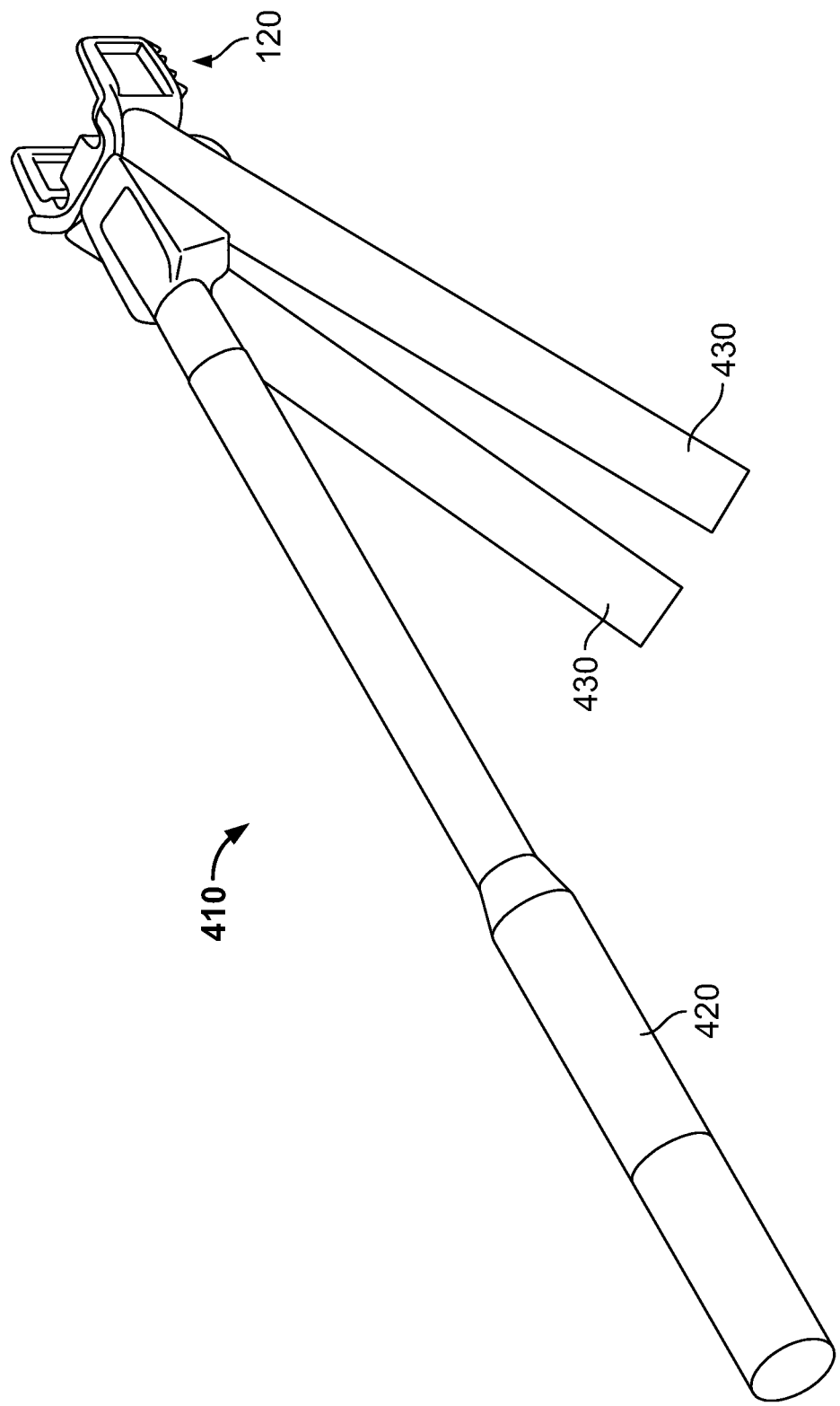
FIG. 20 is a perspective view of a guide tube system for inserting bone screws into a base member of an interbody device in accordance with an aspect of the present invention.

A first guide tool 410 as illustrated in FIG. 20 can be provided to allow a surgeon to hold and position the base member 120 against the bone, and to accurately drill into the bone. The guide tool 410 includes a handle 420 for holding and manipulating a position of the guide tool 410. A projection (not shown) extends from a base portion of the guide tool 410 and is configured to engage hole 270 in the primary member 200 of the base member 120 to hold the guide tool 410 in position. When the handle 420 is properly engaged with the base member 120, a pair of guide tubes 430 is properly lined up with corresponding bone screw holes 240. The surgeon then inserts a drill or center punch (not shown) through one of the guide tubes 430 to drill a hole in the bone, through the screw hole 240. Then, after removing the drill, the surgeon inserts a bone fastener/screw 150 held at the end of a suitable driver (not shown) through the guide tube 430, and screws it into the bone. The process is repeated until the desired number of screws are placed, leaving the base member secured to the bone via the first bone screw holes 240. Or, since the first guide tool 410 includes two guide tubes 430, the bone fasteners/screws 150 can be inserted at substantially the same time.

Figure 21:
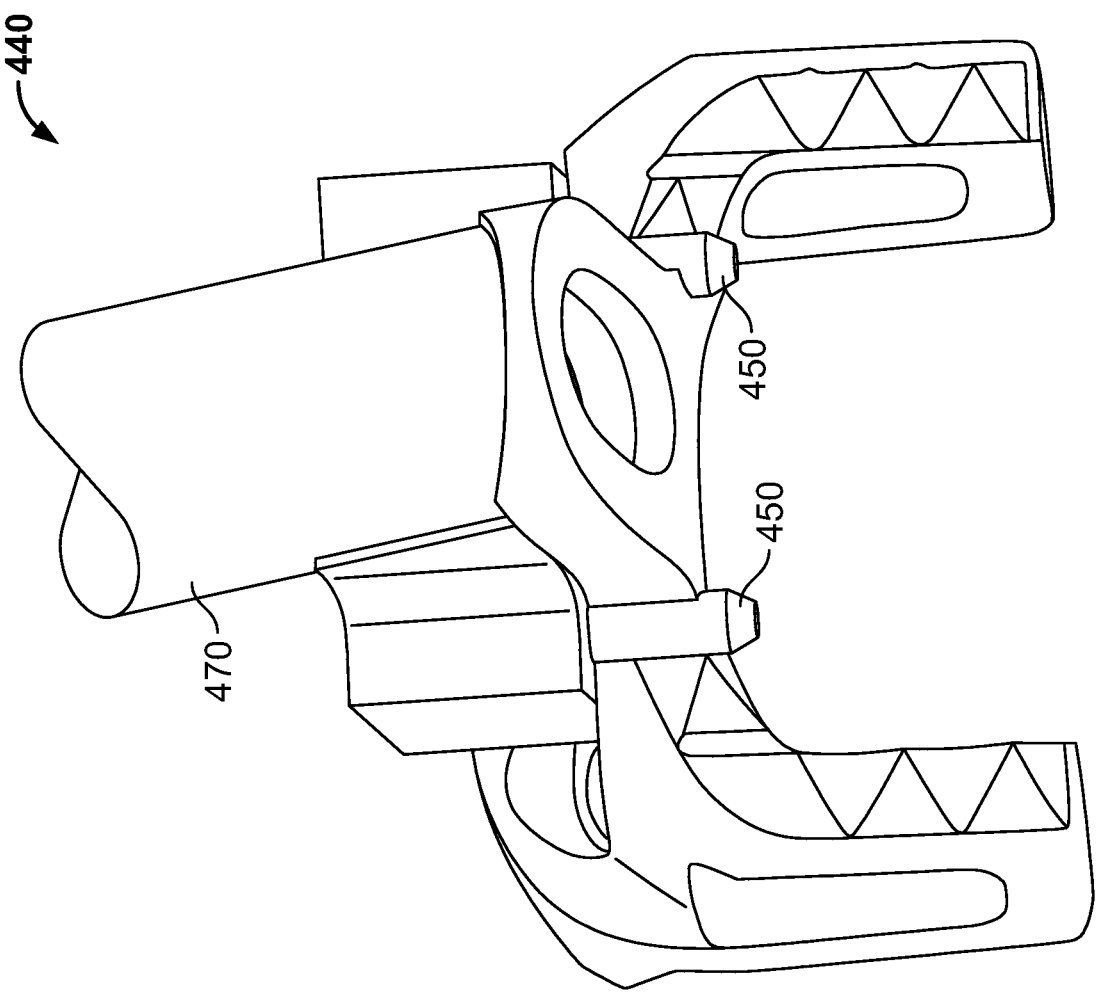
FIG. 21 is a bottom perspective view of another guide tube system for inserting a bone screw into a base member of an interbody device in accordance with an aspect of the present invention.

A second guide tool 440 as illustrated in FIG. 21 is also provided to allow a surgeon to hold and position the base member 120 against the bone, and to accurately drill into the bone. More specifically, the second guide tool 440 is employed to drill a fastener screw 150 into the bone slot 280. The second guide tool 440 includes two substantially round projections 450 that engage corresponding notches 460 provided between the secondary member 210 of the base member 120 and an adjacent interface member 130 provided on each side of the secondary member 210 (see FIGS. 11 and 12) to hold the second guide tool 440 in position. As above, the surgeon then inserts a drill (not shown) through a guide tube 470 to drill a hole in the bone, through the screw slot 280. Then, after removing the drill, the surgeon inserts a bone fastener 150 held at the end of a suitable driver (not shown) through the guide tube 470, and screws it into the bone. It should be noted that one function of the guide is to locate the screw at the end of the slot so the screw travel can match subsidence of the teeth. If for example the screw was placed in the center of the slot it would bottom out in the slot before the teeth had fully embedded.

In another embodiment, the bone fastener/screw 150 configured to pass through the apertures in the base member 120 can have pointed ends which comprise a cutting flute on the tip. The cutting flute at the tip of the bone fastener 150 allows the screw to be self-drilling or self-tapping. Thus, the use of a bone fastener 150 having a self-drilling or self-tapping tip makes the use of a drill or center punch optional.

Turning back to FIGS. 18 and 19, once the bone screws 150 are inserted into the bone screw holes 240 and the bone screw slot 280, the restraining plate 160 is placed over the base member and fixed in place to prevent the fasteners/screws 150 from "backing out" of the screw holes 240, 280. The second bone fastener 150 that extends through the bone screw slot 280 is nonetheless permitted to slide along the length of the slot 280, even when the restraining plate 160 is secured in place. Thus, the second bone fastener 150 and the bone screw slot 280 cooperate to control any lateral or rotary movement of one vertebral body relative to an adjacent vertebral body during "settling" of the bone. Further, the angled orientation of the second member 210 provides the base member 120 with resilient properties, for example, enabling the base member 120 "flex" when one vertebra is rotated relative to an adjacent vertebrae.

As shown in FIG. 19, the interbody device 110 of the present invention has a substantially low profile. Namely, the base member of the present invention is designed to have an outer periphery that coincides with or generally matches the outer diameter of the cortex. The top surface of the base sits at, and possibly below, the top surface of the vertebral bodies. As such, the interbody device 110 of the present invention does not have any parts that would significantly interfere with or irritate the trachea, esophagus, and/or other anatomic structures of the patient.

Another advantage of the interbody device 110 is that it is stackable. Frequently after a bone graft is inserted and a bone plate joined to the surrounding vertebral bodies, for example, C4 and C5, an adjacent disk, for example, between C5 and C6, subsequently deteriorates. With traditional bone plates, it would be necessary to remove the plate from C4-C5 before attaching a second bone plate to C5 and C6 because each plate covers a significant surface of the vertebral body. To remove a bone plate, it is necessary dissect scar tissue, which can have a negative impact on the patient. In contrast, the interbody device 110 of the present invention covers an insignificant portion of the top surfaces of the vertebral bodies to which it is attached, instead being located primarily between the vertebral bodies. As a result, multiple interbody devices can be introduced over adjacent bone grafts (i.e., between a common vertebral body) so that two interbody devices are attached to a common vertebral body without the bone plate systems contacting one another. Thus, subsequent procedures where new bone grafts are to be inserted do not require the removal of a pre-existing device prior to introduction of a new device. The depicted systems where the bone screws are provided in a generally triangular arrangement further enhance the stacking ability of the interbody devices of the invention.

Figure 22:
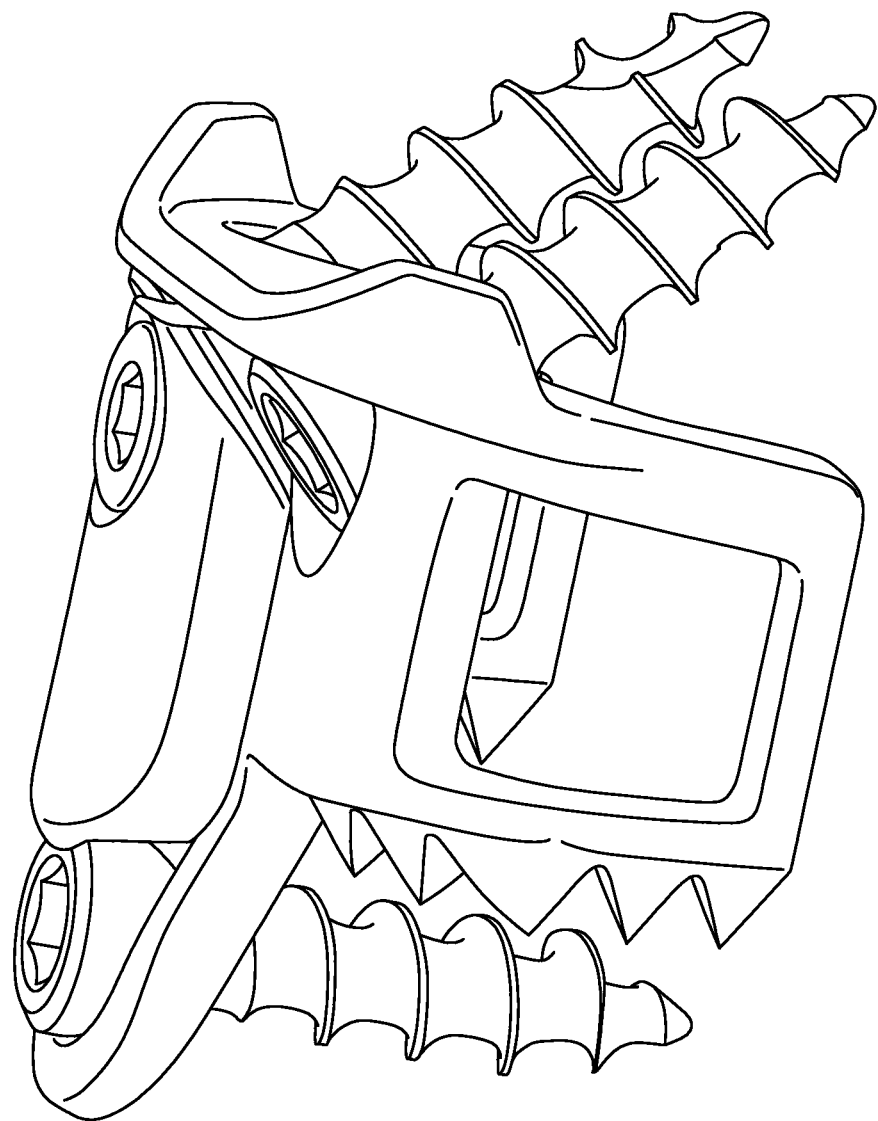
FIG. 22 is a side perspective view of another interbody device in accordance with an aspect of the present invention.
Figure 23:
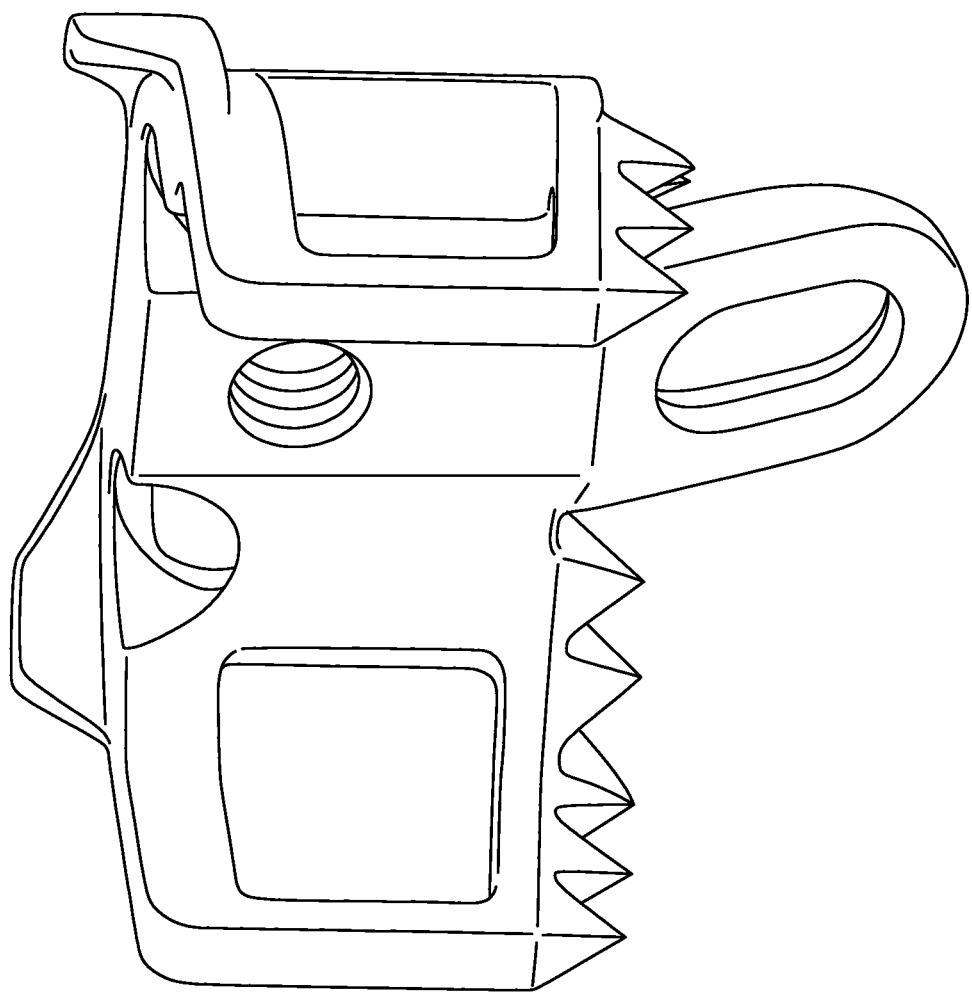
FIG. 23 is a back perspective view of another base member of an interbody device in accordance with an aspect of the present invention.

It is to be appreciated that a kit having base plates of different sizes, bone screws of differing lengths and restraining plates complementary to the base plates can be provided. For instance, because of the different physical dimensions of the patients on whom the invention is used, it is considered that bone plate systems of correlative dimensions be available. The present invention is capable of being provided in various sizes for that purpose. FIGS. 22 and 23 illustrate examples of a base member and interbody device, respectively, having a larger size than the interbody device 110 described with respect to FIGS. 8-20. The kit may further comprise a tack tool, a drilling tool, tapping tool and/or one or more screw driving tools.

As noted above, all of the bone fasteners/screws 150 may be permitted to toggle, or pivot, even after the restraining plate 160 is fixed over the base member 120. The ability of the fasteners/screws 150 to toggle permits the interbody device 110 to migrate and self-center after it has been implanted.

The base member 120 is configured such that when first installed on the cervical vertebrae, the interface members 130 contact a surface of at least one of the bone bodies. For instance, in the present example, the base member 120 is positioned between the vertebrae 380 and 390 such that the top surface 250 of the base member 120 contacts an end surface of one vertebral body 380 and the interface members 130 contact an end surface of the other vertebral body 390. As discussed above, the interface members 130 are configured such that substantially immediate penetration does not occur. Rather, the interbody device 110 gradually subsides as the vertebrae and bone graft fuse to share in the weight bearing during settling of the vertebral bodies. Specifically, as the vertebral bodies move toward each other during settling, the interface members 130 will contact and enter the second vertebral body 390 with increased resistance to subsidence. This contact controls the rate of settling.

The interbody device 110 provides such an interface design by controlling the height, size, shape, and spacing of the teeth that interdigitate with the endplate of the vertebral body. In addition screw fixation is provided. The length of screw travel in the slot 280 is possibly matched to the height of the interface members 130. Accordingly, subsidence is arrested once the bone fastener 150 reaches the intended limit as provided by the slot 280. Screw fixation also addresses expulsion of the interbody device, a concern common to all interbody devices. The interbody device 110 accommodates a large graft surface area further increasing the probability that fusion will occur.

The interbody device 110 as described above can have a variety of alternative configurations. Various configurations can include, but are not limited to, those shown in FIGS. 24 through 29.

Figure 24:
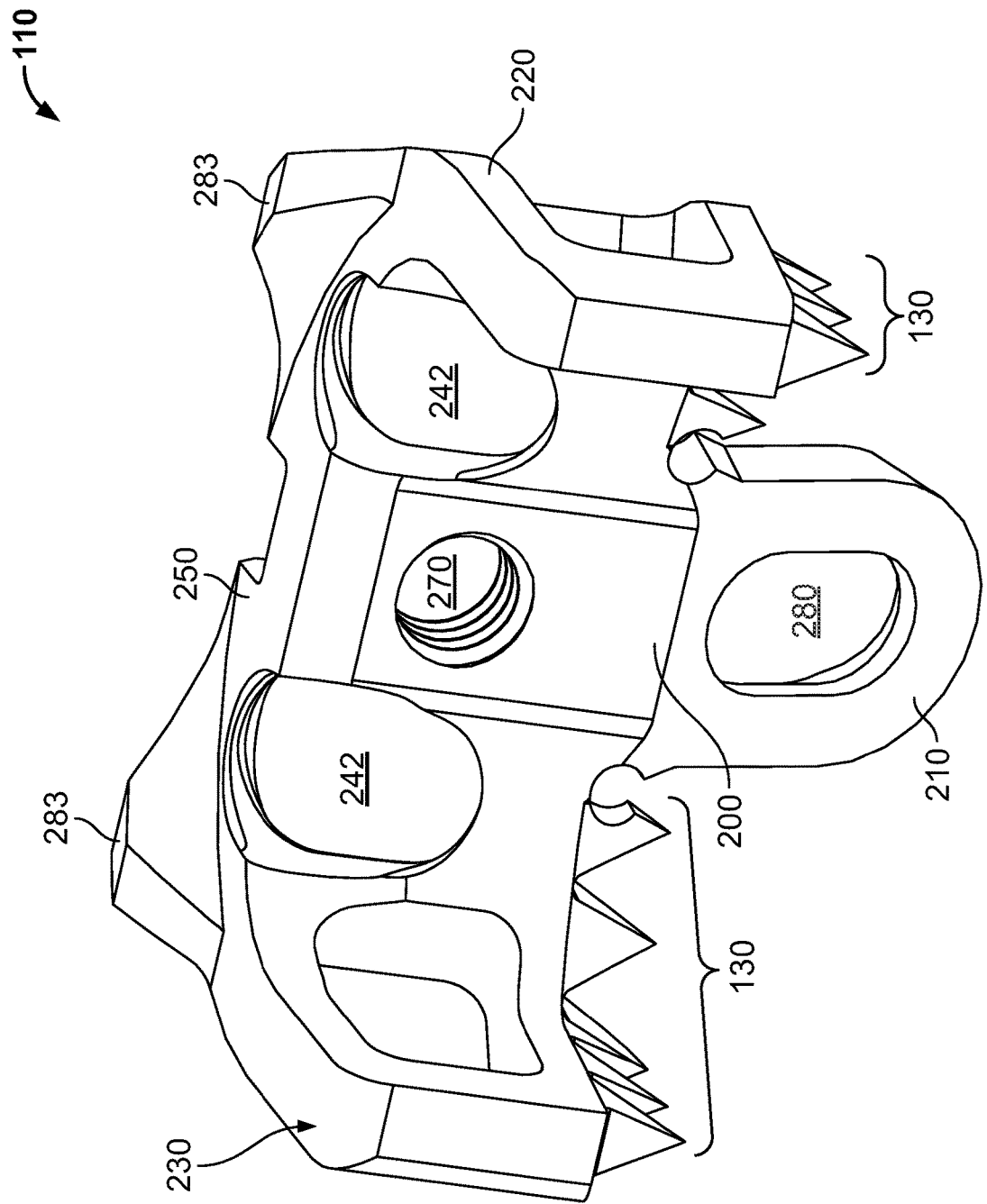
FIG. 24 is a back perspective view of a base member of an interbody device in accordance with an aspect of the present invention.

FIG. 24 illustrates an interbody device 110 comprising a base member 120 having a primary member 200 and a secondary member 210. The primary member 200 includes at least one first elongated slot 242 extending therethrough that is configured to receive a corresponding bone screw or fastener. Further, the secondary member 210 includes at least one second elongated slot 280 extending therethrough that is configured to receive a bone screw. The elongated slot 280 of the secondary member 210 is similarly referenced and described above with regard to FIGS. 11 and 12. The primary member 200 also includes a threaded hole 270 for receiving a restraining means configured to mitigate the backing out of at least one bone fastener from a bone body.

Figure 27:
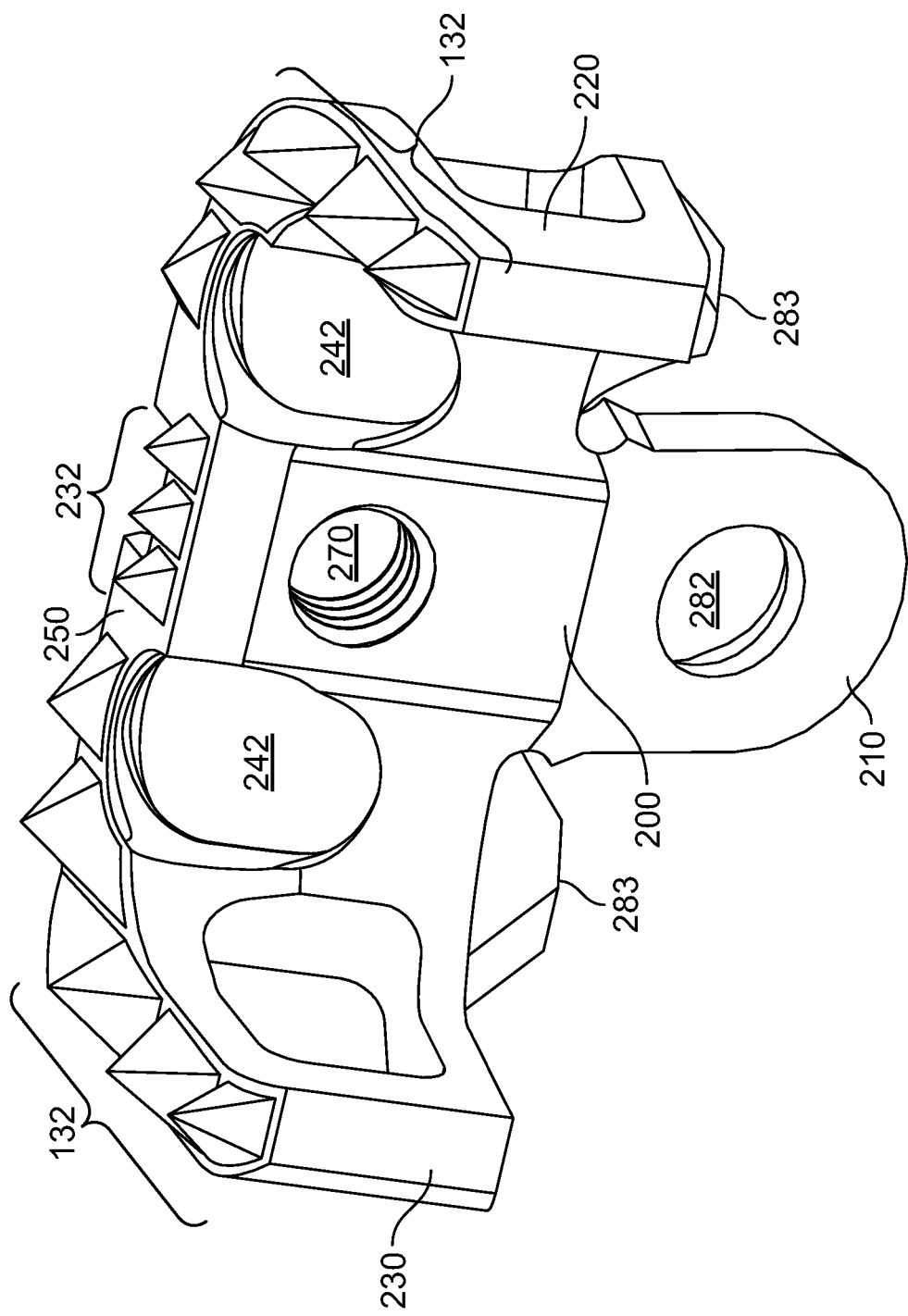
FIG. 27 is a back perspective view of a base member of an interbody device in accordance with an aspect of the present invention.

The interbody device 110 of FIG. 24 can include at least one (two are shown) projection 283 that extends upward from the top surface 250 of the primary member 200. The projection 283 provides a base or shelf that contacts a bone body in order to stop the interbody device 110 against a corresponding bone body upon insertion into a human. Although not shown in FIG. 24, the at least one projection 283 can alternatively be positioned to extend from the bottom surface of the primary member 200. In one example, FIG. 27 illustrates two projections 283 extending from the bottom surface of the primary member.

Figure 25:
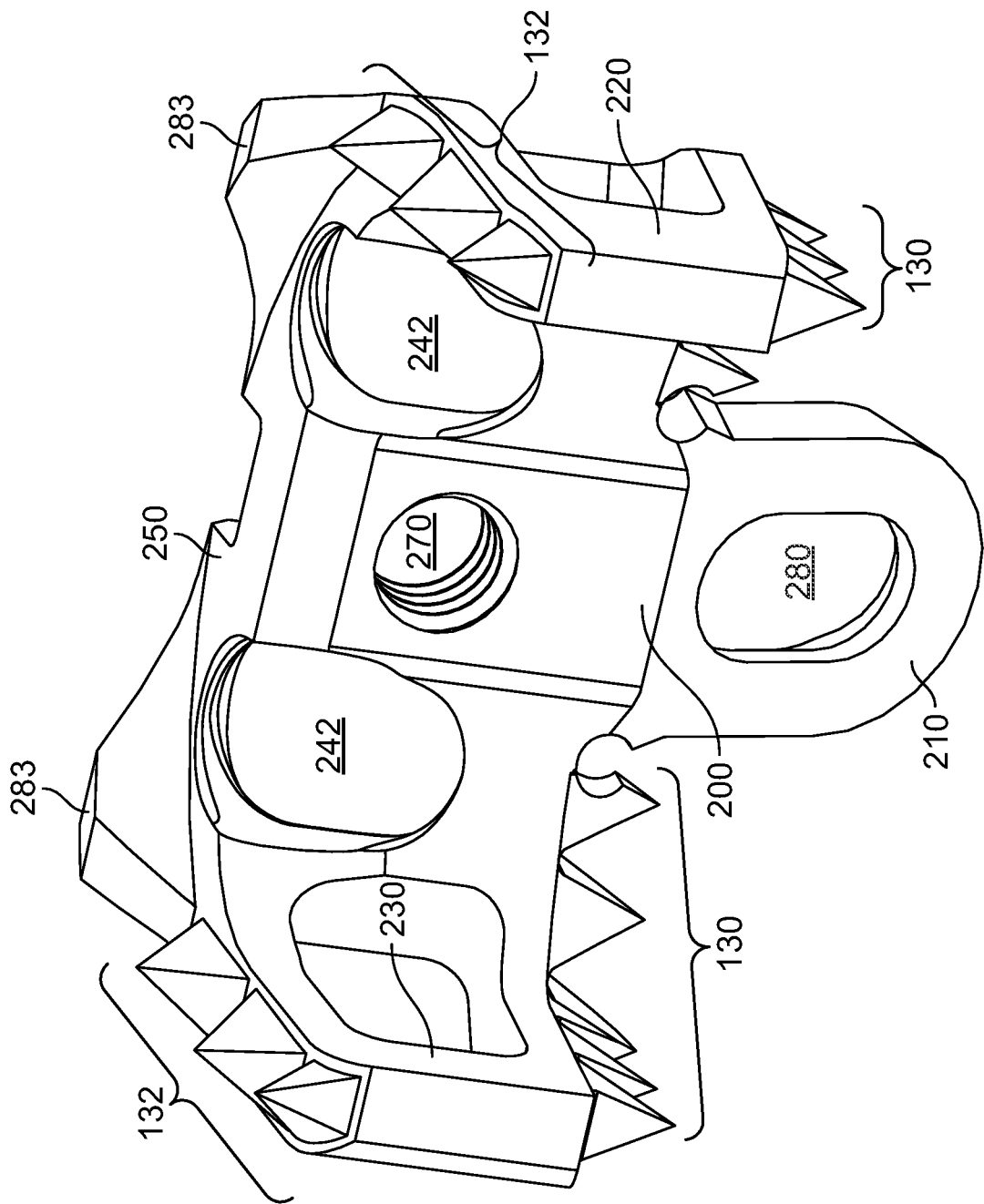
FIG. 25 is a back perspective view of a base member of an interbody device in accordance with an aspect of the present invention.

The primary member 200 of the interbody device 110 has a plurality of interface members 130 extending from the bottom surface. The interface members 130 can comprise, for example, teeth, knife-edges, spikes, posts, pegs, or combinations thereof. The interface members 130 provide a controlled subsidence interface between the interbody device 110 and a corresponding bone body. Although not shown in FIG. 24, interface members may also extend from the top surface of the primary member 200 so as to provide two controlled subsidence interfaces between the interbody device 110 and two adjacent bone bodies. In one example, FIGS. 25 and 27 illustrate various configurations of interface members 132 that may extend from the top surface of the primary member 200. To promote controlled subsidence, the interface members may extend from the top or bottom surface of the primary member 200 in a direction that is aligned with an elongate direction of two adjacent bone bodies, such as two vertebrae in a spine. For example, FIGS. 18 and 19 illustrate the interbody device 110 positioned between two adjacent bone bodies.

As illustrated in FIG. 24, the primary member 200 can have two elongated slots 242 configured such that bone screws extend through the slots 242 at an angle. Thus, each bone screw extending through the first bone screw slots 242 can enter a bone body at an angle. The elongated slots 242, 280 of the primary and secondary members 200, 210 are sufficiently large to allow a portion of a bone screw, such as a threaded shaft that extends into a bone body, to pass therethrough but not large enough to allow a retaining portion of the bone screw through, such as the head of the bone screw. The general aspects of the bone screw or bone fastener are described above with regard to FIG. 15. The elongated slots 242, 280 may have a seat portion on which the retaining portion of a bone screw can rest. The seat portion of the slots 242, 280 has a generally concave spherical shape and the surface of the retaining portion of a bone screw in contact with the seat has a complementary convex spherical configuration. In this regard, the retaining portion, such as the head, of a bone screw is free to pivot on the seat of the elongated slot 242, 280.

The elongated slots 242, 280 of the primary and secondary members 200, 210 in FIG. 24 are configured to permit bone screws extending therethrough to slide and rotate along the elongation length of the slots 242, 280 during controlled subsidence. In other words, the bone screws can slide relative to the interbody device 110 as the interface members 130 progressively penetrate into a corresponding bone body over time. As the bone screws slide along the elongation length of the slots 242, 280, at least one bone screw can eventually slide against the end of a slot 242, 280 it extends through. In this case, the bone screw becomes secured at the end of the corresponding slot 242, 280 such that the bone screw can no longer slide relative to the interbody device 110 as the interface members 130 may continue to penetrate into the corresponding bone body. Subsidence resistance increases as the at least one bone screw becomes secured at the end of the slot 242, 280 and can no longer slide relative to the interbody device 110. At the end of the slot 242, 280, the bone screw can toggle in order to assist the interface members 130 to further penetrate into a corresponding bone body.

Although FIG. 24 illustrates interface members 130 extending only from the bottom surface of the primary member 200, the following description of the affect the elongation length of the slots 242, 280 may have on subsidence resistance is based on interface members 130, 132 extending from the bottom and top surface of the primary member 200, for example, as illustrated in FIGS. 12, 25 and 27. Each elongated slot 242, 280 of FIG. 24 can have an elongation length that is less than, about the same as or greater than the height of at least one single interface member 130, 132. Alternatively, each elongated slot 242, 280 can have an elongation length that is less than, about the same as or greater than the height of any single interface member 130, 132.

The elongation length of the at least one slot 242 in the primary member 200 can be substantially the same as, less than or greater than the elongation length of the at least one slot 280 in the secondary member 210 depending on the desired controlled subsidence profile. Varying the elongation length of at least one slot 242, 280 can mitigate the effects that poor bone quality or an irregular surface of a bone body can have on the controlled subsidence profile. In the case that the elongation length of any one slot 242, 280 is matched to or about the same as the height of the interface members 130, 132, further subsidence resistance can occur after the bone screw slides relative to the interbody device 110 the intended limit as provided by the elongation length of the slot 242, 280. As at least one interface member 130, 132 becomes fully penetrated into a bone body, at least one bone screw becomes positioned at the end of the slot 242, 280 the screw extends through. As the bone screw rests at the end of the slot 242, 280, further subsidence resistance can occur as the bone screw toggles at the end of the slot 242, 280. The toggling of the bone screw at the end of the slot 242, 280 permits the interface members 130, 132, of which some members 130, 132 may not be fully embedded in a bone body, to further penetrate into the bone body. In theory, without being bound thereto, one reason for the continued penetration of a fully-embedded interface member 130 into a bone body is poor bone quality. In another aspect, the surface of a bone body can be irregular such that a substantially flat or flush surface is not available on which the shelf-like bottom or top surface of the primary member 200 can rest. The irregular surface of a bone body can result in some of the interface members 130 not becoming fully embedded in a bone body. Depending on the degree of irregularity of a bone body surface, some of the interface members 130, 132 may also not be in contact with a bone body when the bone fastener/screw 150 slides relative to the interbody device 110 to the end the slot 242, 280. Therefore, as discussed above, toggling of the bone screw at the end of the slot 242, 280 can force the interface members 130, 132 that are not fully embedded in a bone body to penetrate further and become fully embedded.

In the case that the elongation length of any one slot 242, 280 is less than the height of the interface members 130, 132, the bone screw tends to not reach or slide to the end of the slot 242, 280 prior to any single interface member 130, 132 becoming fully embedded into a bone body. Thus, the subsidence resistance is increased when the elongation length of any one slot 242, 280 is less than the height of at least one single interface members 130, 132. In use, as the interface members 130, 132 begin to penetrate into a bone body, but before any single member becomes fully embedded, a bone screw may slide along the elongation length of the slot 242, 280 and reach the end of the slot 242, 280. Being positioned at the end of the slot 242, 280, the bone screw is forced to toggle so the interface members can further penetrate into a bone body and thus subsidence resistance is increased. In this instance, toggling of the bone screw at the end of the slot 242, 280 can assist the interface members 130, 132 that are not fully embedded in a bone body to penetrate further and become fully embedded.

In the case that the elongation length of any one slot 242, 280 is greater than the height of the interface members 130, 132, the bone screw tends to not reach or slide to the end of the slot 242, 280 prior to any single interface member 130, 132 becoming fully embedded into a bone body. Increasing the length a bone screw can travel or slide in a slot 242, 280 can decrease subsidence resistance. For example, an irregular bone body surface can cause at least one interface member 130, 132 to become fully embedded in a bone body before a bone screw slides relative to the interbody device 110 to the end of the slot 242, 280. The bone screw in this instance can continue to slide along the elongation length of the slot 242, 280 as the remaining interface members 130, 132 continue to further penetrate into a bone body surface. The additional distance or length the bone fastener 150 can travel before reaching the end of the slot 242, 280 generally makes it unnecessary for the bone fastener 150 to toggle in slot 242, 280 to ensure that the interface members 130, 132 become fully embedded in a bone body. The subsidence resistance profile in this case would be substantially lower because, in part, the bone screw generally does not need to toggle in the slot 242, 280 in order to ensure the interface members 130, 132 become fully embedded. Further, the bone fastener 150 in this case will not generally rest at the end of the slot 242, 280, which can increase the subsidence resistance.

In another aspect, the elongation length of any one slot 242, 280 of the interbody device 110 of FIG. 24 can be substantially zero. The slot 242, 280 in this instance tends to function substantially the same as a bone screw hole as described above, for example, with regard to hole 240 of FIGS. 11 and 12. Thus, the slot 242, 280 has substantially no elongation over which a bone screw can travel along. In this regard, a bone screw is forced to toggle in the slot 242, 280 to assist penetration of the interface members 130, 132 into at least one bone body and thus subsidence resistance is increased in this configuration. That is, a stiff construct comprising at least one bone body and the interbody device 110 results from the elongation length of any one slot 242, 280 being substantially zero.

As can be seen above with regard to the interbody device 110 of FIG. 24, the subsidence resistance profile can be controlled and/or affected by the combination of the elongation length of any single slot 242, 280 and the shape, location and height of the interface members 130, 132. Each of these features of the present invention can be adjusted, modified or combined in order to compensate for poor bone quality, an irregular surface of a bone body or to ensure full penetration of the interface members 130, 132 into at least one bone body.

Turing to FIG. 25, the interbody device 110 can have interface members 132 on the top surface of the first and second legs 220, 230 of the primary member 200. The interbody device 110 can further have interface members 130 extending from the bottom surfaces of the primary member 200, the first leg 220 and the second leg 230. FIG. 26 illustrates interface members 130, 132 extending from the top and bottom surface of a representative leg of the primary member 200. Although not shown in FIG. 25, the interbody device 110 can have additional interface members 132 which extend upward from the top surface 250 of the primary member 200. In one example, FIG. 27 illustrates interface members 132 extending upward from the top surface 250 of the primary member 200. The interbody device 110 of FIG. 25 has at least one bone screw slot 242 in the primary member 200 and at least one bone screw slot 280 in the secondary member 210. As shown, FIG. 25 illustrates two bone screw slots 242 in the primary member 200 and one bone screw slot 280 in the secondary member 210. In this embodiment, the interbody device 110 provides controlled subsidence at the interface of the top interface members 132 with a corresponding bone body and at the interface of the bottom interface members 130 with a corresponding bone body. The primary member 200 also includes a threaded hole 270 for receiving a restraining means configured to mitigate the backing out of at least one bone fastener from a bone body.

Each elongated slot 242, 280 of FIG. 25 can have an elongation length that is less than, about the same as or greater than the height of at least one single interface member 130, 132. Further, each elongated slot 242, 280 can have an elongation length that is less than, about the same as or greater than the height of any single interface member 130, 132. The at least one slot 242 in the primary member 200 and at least one slot 280 in the secondary member 210 can have about the same or varying elongation lengths depending on the desired controlled subsidence profile. As discussed above with regard to FIG. 24, the elongation length of each slot 242, 280 in the interbody device 110 of FIG. 25 can also be modified to increase or decrease the subsidence resistance as the interface members 130, 132 penetrate into corresponding bone bodies.

In one aspect, the height of the interface members 130, 132 may be about half of the overall desired controlled subsidence distance. For example, if it is desirable to have a total of 2 mm of penetration into the corresponding bone bodies, the top interface members 132 and bottom interface members 130 may each respectively have a height of about 1 mm. In another aspect, the interface members 130, 132 may each respectively have about 1 to 99 percent of the overall desired subsidence control. In yet another aspect, interface members 132 can be located on only the top surface of the first leg 220, second leg 230 or primary member 200 (see FIG. 27) or the interface members 130 can be located on only the bottom surface of the first and second legs 220, 230 or the primary member 200 (not shown). In this case, controlled subsidence would only occur at the interface of the top members 132 and a corresponding bone body or at the interface of the bottom members 130 and a corresponding bone body.

FIG. 27 illustrates an interbody device 110 having a pair of elongated slots 242 extending through the primary member 200. The interface members 132 of the device 110 extend from the top surface of the primary member 200 and first and second legs 220, 230. The secondary member 210 has a single bone screw hole 282 configured for receiving a bone screw. Projections 283 extend from the bottom surface of the primary member 200 and provide a shelf or surface to stop the interbody device 110 against a bone body upon insertion into a spine. The projections 283 may be positioned on the bottom surface of the primary member 200 in order to increase the area on the top surfaces 250 of the primary member 200 and first and second legs 220, 230 on which the interface members 132 may be located.

Figure 28:
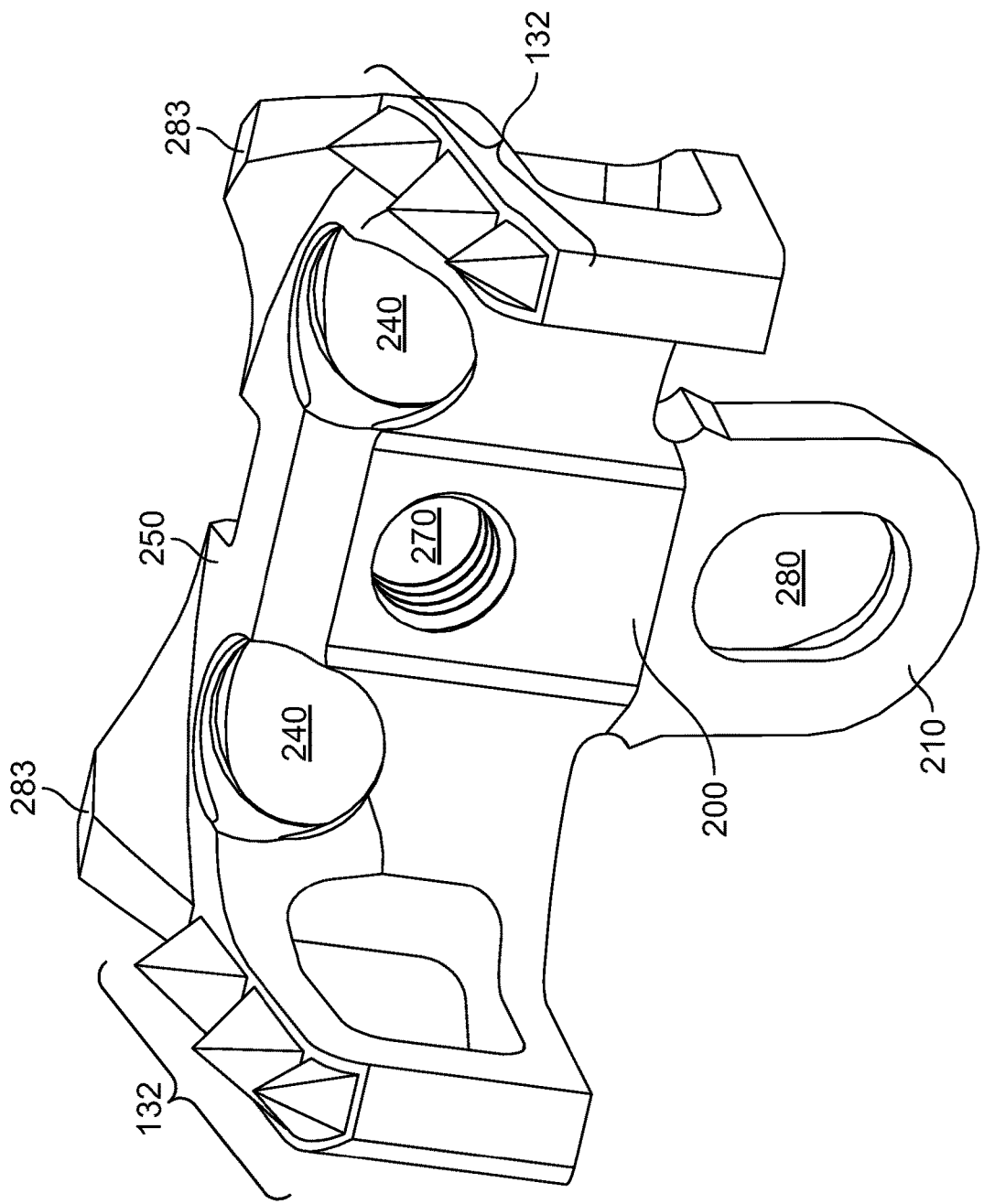
FIG. 28 is a back perspective view of a base member of an interbody device in accordance with an aspect of the present invention.

In another aspect, the single screw hole 282 in the secondary member 210 of the interbody device 110 of FIG. 27 may be an elongated slot 280 and the pair of elongated slots 242 of the primary member 200 may be a pair of screw holes 240. For example, the interbody device 110 of FIG. 28 illustrates an interbody device 110 having two bone screw holes 240 in the primary member 200 and an elongated slot 280 in the secondary member 210. The primary member 200 also may include a threaded hole 270 for receiving a restraining means configured to mitigate the backing out of at least one bone fastener from a bone body.

Figure 29:
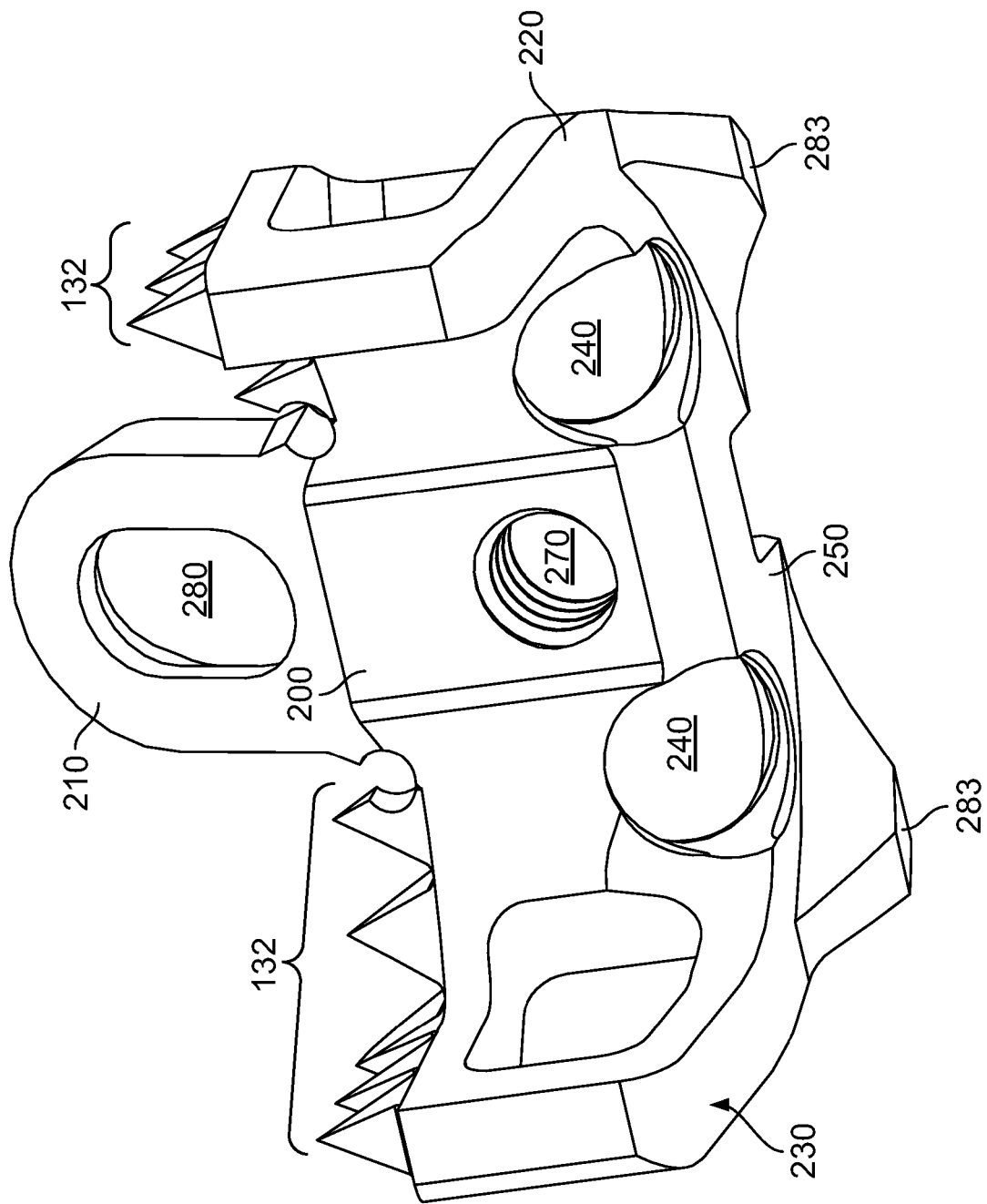
FIG. 29 is a back perspective view of a base member of an interbody device in accordance with an aspect of the present invention.

FIG. 29 illustrates yet another alternative configuration of the interbody device 110. The interbody device 110 of FIG. 29 may be configured for insertion into a spine such that the secondary member 210 extends upward from a surface of the primary member 200. That is, FIG. 29 illustrates an inverted view of the interbody device 110 shown in the other Figures herein. The interface members 132, which generally extend downward as representatively shown in FIGS. 24 through 28, extend upward in the direction of the secondary member 210. In this embodiment, the interbody device 110 provides controlled subsidence at the interface of the top interface members 132 and a corresponding bone body. The primary member 200 and secondary member 210 are arranged relative to each other so that their front surfaces at their interface form an angle greater than 90° and less than 180°, or about 110° to about 160°. As shown, the primary member 200 can include at least one bone screw hole 240 and the secondary member 210 can include at least one elongated slot 280. The elongated slot 280 can have an elongation length that is less than, about the same as or greater than the height of at least one single interface member 132. Alternatively, the elongated slot 280 can have an elongation length that is less than, about the same as or greater than the height of any single interface member 132. As discussed above with regard to FIG. 24, the elongation length of slot 280 in the interbody device 110 of FIG. 29 can be modified to increase or decrease the subsidence resistance as the interface members 132 penetrate into a bone body. Further, as shown in the Figures herein, the primary member 200 may also include a threaded hole 270 for receiving a restraining means configured to mitigate the backing out of at least one bone fastener from a bone body.

Although not shown in FIG. 29, the interbody device 110 can have additional interface members extending from a bottom surface of the primary member 200, for example, as illustrated in FIGS. 25 and 27. In another aspect, the secondary member 210 may include an aperture other than the elongated slot 280 shown, such a bone screw hole as shown in FIG. 27. In yet another aspect, the primary member 200 may include an aperture other than the bone screw holes 240 shown, such as an elongated slot as shown in FIGS. 24 and 25.

In another embodiment, the various configurations of the interbody device 110, including but not limited to those shown in FIGS. 24 through 29, may include a plurality of interface members of any desirable height and shape. In one example, as shown in FIG. 24, each of the plurality of interface members 130 extending upward from the surface of the primary member 200 can have the same height.

Alternatively, the plurality of interface members 130 of FIG. 24 may have different heights such that at least one of the plurality of members 130 extending from the primary member 200 has a height substantially not equal to at least one other interface member 130 (not shown). In this regard, the profile of interface members 130 extending from a surface of the primary member 200 may be varied or contoured to the surface of a corresponding bone body, such as an irregular or substantially non-flush surface for the interbody device 110 to rest upon. The shape and height of the plurality of interface members 130 may be modified to fit into or conform with the irregularities of a bone body surface, such a peaks, bumps, cavities, voids and the like. Such irregularities may reduce the number of interface members 130 which fully penetrate a bone body and the depth to which interface members 130 may become embedded. Thus, irregular bone body surfaces provide different controlled subsidence profiles.

While shown embodiments of the present invention are described for supporting adjacent cervical vertebrae in the anterior region of the vertebrae, persons skilled in the art would recognize that the bone plate of the present invention may be utilized to support adjoining thoracic and lumbar vertebrae in the lateral or posterior regions of the vertebrae. Further, the device and method of the invention is not limited to vertebral bodies, but can also be used to join two other pieces of bone in other parts of the body.

Figure 32:
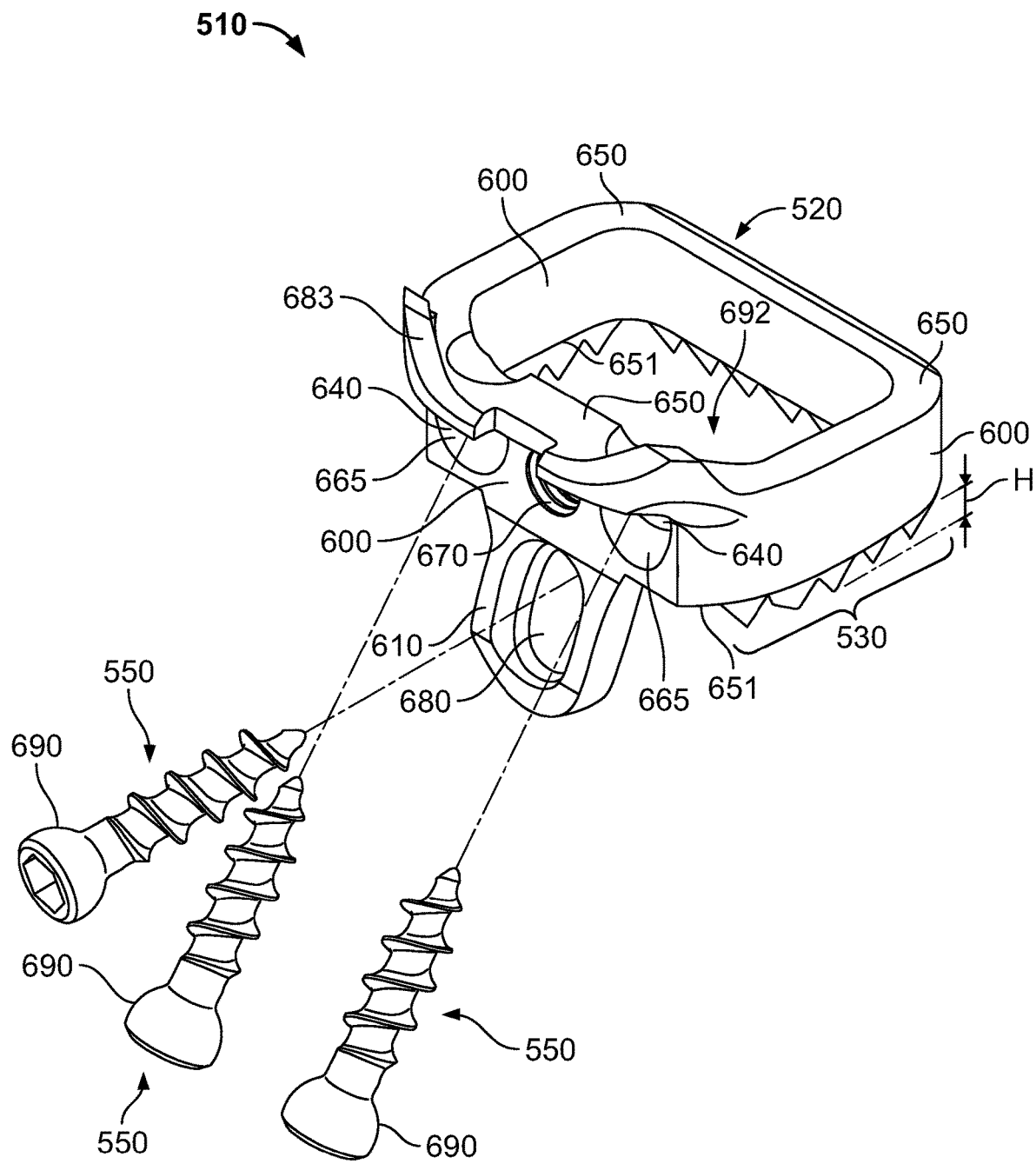
FIG. 32 is an angled front perspective view of an implant device including a base member having a peripherally-surrounded chamber in accordance with an aspect of the present invention.

Referring initially to FIG. 32, an example of a device or implant device 510 is illustrated in accordance with an aspect of the present invention. The implant device 510 is configured to fix and secure two or more bone bodies. As used herein, the phrase "bone bodies" is intended to include individual bones as well as fragments or portions of bones. For example, the bone bodies can be two adjacent vertebrae and the implant device 510 can be mounted to the vertebrae with graft material (not shown) between the vertebrae. More specifically, and as will be described in further detail below, the implant device 510 can fix and secure adjacent vertebrae that have had cartilaginous disc between the vertebrae replaced with material that promotes the fusion of the vertebrae such as a graft of bone tissue or some other similar material. It is to be appreciated that one aspect that is addressed by the present invention is load sharing with a graft.

As shown in FIG. 32, the configuration of the implant device 510 includes a base member 520 having a plurality of protrusions or interface members 530 extending from a surface of the base member 520. The base member 520 has a top surface 650 and a bottom surface 651. As shown, the interface members 530 extend from the bottom surface 651 of the base member 520. Although not shown, the interface members 530 can alternatively extend from only the top surface 650 of the base member 520, or from both the top surface 650 and the bottom surface of the base member 520 in order to provide two controlled subsidence interfaces between the implant device 510 and adjacent bone bodies. The interface members 530 are configured to contact at least one surface of a bone body to provide subsidence control for the implant device 510. The interface members 530 can include, for example, teeth, knife-edges, spikes, posts, pegs, or combinations thereof.

The base member 520 is configured such that when first inserted between two adjacent bone bodies, the interface members 530 contact a surface of at least one of the bone bodies. The interface members 530 are configured such that substantially immediate penetration into a bone body occurs. The implant device 510 gradually subsides as the bone bodies and bone graft fuse to share in the weight bearing during settling of the bone or vertebral bodies. Specifically, as the bone bodies move toward each other during settling, the interface members 530 will penetrate the bone bodies with increased resistance to subsidence.

Controlled subsidence relates to resistance to subsidence and total amount of subsidence. To promote controlled subsidence, the interface members 530 may extend from a surface of the base member in a direction that is aligned with an elongate direction of two adjacent bone bodies, such as two vertebrae in a spine. The interface members are thus configured to provide progressive penetration into a bone body over a period of time. The subsidence profile, which is a relationship between an applied load and an amount of settling the implant device 510 experiences when secured to the bone bodies, is dependent on the configuration or shape of the interface members 530. For example, the interface members 530 can readily penetrate into a bone body initially and then slow down as more of the interface member cross section embeds. The height (H) of the interface members 530 relative to the depth of penetration into a corresponding bone body. Generally, when the implant device 510 has subsided to a point where the interface members are fully embedded in the bone, the applied load will be distributed across the entire surface of the implant device 510 and subsidence resistance will increase. The controlled subsidence relationship between the interface members 530 and the at least one corresponding bone body that the members 530 extend into is described herein.

The base member 520 of the implant device 510 includes a primary member 600 and a secondary member 610, which extends from and is angled relative to the primary member 600. The primary member 600 forms an enclosed loop or peripherally-surrounded chamber 692 that is configured to receive and hold fusion material, such as a bone graft. As shown, the chamber 692 is peripherally-surrounded, but not fully enclosed, such that bone bodies residing above and below the chambers 692 can be in contact with fusion material located in the chamber 692. It is to be appreciated, and for the description purposes of the present invention herein, the peripherally-surrounded chamber 692 can be positioned at any angle in order to accommodate the orientation of bone bodies to be fused together. In any case, the chamber 692 can mitigate lateral shift of the fusion material and control subsidence of adjacent bone bodies as they set during fusion. Subsidence is further controlled by the presence of the interface members 530 that extend from a surface of the base member 520. In the present embodiment, the primary and secondary members 600, 610 are contiguous and unitary. The secondary member 610 has a front surface that is generally continuous with a front surface of the primary member 600, and a back surface that is generally continuous with a back surface of the primary member 600. The primary member 600 and secondary member 610 are arranged relative to each other so that their front surfaces form an angle. Of course, the angle is not of great importance and typically depends upon a compromise between low profile and the amount of bone that would need to be removed. Suffice to say that the angle can be any angle (e.g., greater than 90° and less than 180°). However, a typical angle would be in the range, from about 140° to about 170°. The angle at which the primary and secondary members 600, 610 are joined is provided so that bone screws can be introduced through the base member 520 at desired angles. Alternatively, the base member 520 can be designed in any other manner that permits the bone screws to be introduced there through at the desired angles.

The primary member 600 can form the peripherally-surrounded chamber 692 to be of any shape or size to accommodate adjacent bone bodies of various shapes, sizes and positions. The peripherally-surrounded chamber 692 of the present invention is designed to have an outer periphery that coincides with or generally matches the outer diameter of the cortex or adjacent vertebrae. The top surfaces of the implant device 510 sit at, and possibly below, the top surface of the vertebral bodies. As such, the implant device 510 of the present invention does not have any parts that would significantly interfere with or irritate the adjacent anatomic structures of the patient. As shown, the peripherally-surrounded chamber 692 has a rounded-edge rectangular shape that would adequately accommodate two adjacent vertebrae of a spinal column. The primary member 600 generally forms the vertically-open and peripherally-surrounded area 692, when viewed in the implanted position in a spinal column, that can receive and hold fusion material between two or more bone bodies. In use, the primary member 600 laterally extends around an amount of fusion material, such as a bone graft, in order to mitigate lateral shift of the graft and control subsidence of adjacent vertebrae as the vertebrae set during fusion. The fusion material can be packed into the peripherally-surrounded chamber 692 formed by the primary member 600. The chamber 692 of the implant device 510 creates a one-piece fusion material housing that substantially reduces the need for other devices that may be necessary to fuse multiple bone bodies together. The peripherally-surrounded chamber 692 adequately houses fusion material that would generally be supported by a cage design implant. In this case, a plate would generally also be needed to keep the bone bodies and the cage in the desired location. The implant device 510 described herein significantly reduces the cost associated with multiple-device fusion methods such as those associated with the above cage and plate combination devices.

Another advantage of the implant device 510 is that it is stackable. The implant device 510 of the present invention covers an insignificant portion of the top surfaces of the vertebral bodies to which it is attached. As a result, multiple implant devices can be introduced over adjacent bone grafts (i.e., between a common vertebral body) so that two implant devices 510 are attached to a common vertebral body without devices 510 contacting one another. Thus, subsequent procedures where new bone grafts are to be inserted do not require the removal of a pre-existing device prior to introduction of a new device. The depicted systems where the bone screws are provided in a generally triangular arrangement further enhance the stacking ability of the implant devices 510 of the invention. It is to be appreciated that the implant device 510 can be of different scales or sizes, have differing bone screw lengths and restraining plates that are complementary to different physical dimensions of the patients on whom the invention is used and the spinal location or level at which the device is implanted. The present invention is capable of being provided in various sizes for that purpose.

The peripherally-surrounded chamber area 692 provides a retaining region or open area into which fusion material can be packed or loaded. It is possible to load fusion material, such as particulate graft material including bone chips and/or bone paste, into the chamber 692 prior to the insertion of the implant device 510 between adjacent bone bodies such as vertebrae. Bone chips and/or bone paste and possibly in combination with growth factors can be used in place of a block of bone graft material. Often it is the case that bone chips and bone paste are more easily retained in a peripherally-surrounded chamber 692 as opposed to an implant device 510 which has an open posterior end. Thus, a combination of bone chips and bone paste is better retained in a center region of an implant device 510 such as that provided in the Figures shown herein.

In accordance with another aspect of the present invention, any portion or the entire implant device 510 can be constructed from radiotransparent or radiolucent materials. Specifically, in order to facilitate radiographic evaluation of the fusion material and the corresponding bone bodies, the base member 520, primary member 600, secondary member 610, any other portion or component of the implant device 510 or combinations thereof can be constructed from radiotransparent or radiolucent materials. For example, the entire implant device 510 can be constructed from radiolucent material. Radiolucent materials permit x-rays to pass through components of the implant device 510 so that developed x-ray pictures provide more visibility of the fusion material and bone bodies without significant interference, such as imaging artifacts, caused by the device 510. Radiolucent materials enable clear visualization through imaging techniques such as x-ray and computer tomography (CT), whereas traditional metallic or alloy implant materials that are radiopaque can generate imaging artifacts and scatter that prevent a comprehensive inspection of the surrounding tissue, bone and fusion material. Thus, radiolucent materials allow for clearer imaging of bone bodies and fusion materials.

Radiolucent materials can include, but are not limited to, polymers, carbon composites, fiber-reinforced polymers, plastics, combinations thereof and the like. One example of a radiolucent material that can be used with the aspects of the present invention described herein is PEEK-OPTIMA® polymer supplied by Invibio Inc., Greenville, S.C. The PEEK-OPTIMA® polymer is a polyaromatic semicrystalline thermoplastic known generically as polyetheretherketone. The PEEK-OPTIMA® polymer is a biocompatible and inert material. Known alternatives to PEEK-OPTIMA® include, but are not limited to, biocompatible polymers such as ENDOLIGN® polymer composite supplied by Invibio Inc., Greenville, S.C. The ENDOLIGN® polymer is a biocompatible carbon fiber-reinforced thermoplastic material. Radiolucent materials, including those described above, can optionally be doped or combined with radiopaque materials in different concentrations in order to vary the level of x-ray contrast and/or visual characteristics. The portions of the implant device 510 constructed from radiolucent material can be prepared by any conventional technique known in the art such as machining, injection molding or compression molding.

Figure 35:
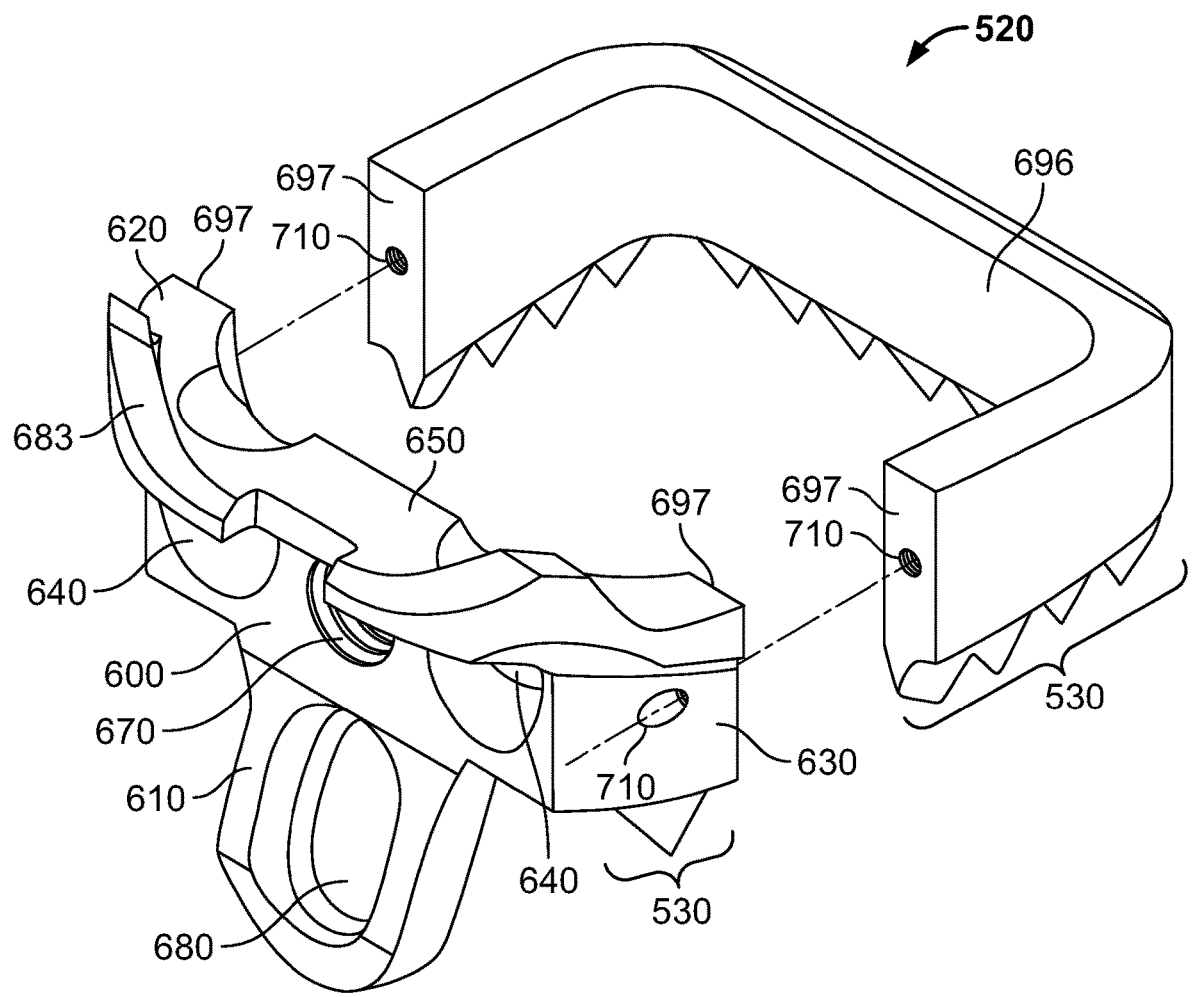
FIG. 35 is an angled front perspective view of a base member of an implant device including a peripherally-surrounded, chamber in the unassembled position in accordance with an aspect of the present invention.

In another embodiment, the implant device 510 can include a combination of components constructed from both radiolucent materials and radiopaque materials. Radiopaque materials are traditionally used to construct devices for use in the medical device industry. Radiopaque materials include, but are not limited to, metal, aluminum, stainless steel, titanium, titanium alloys, cobalt chrome alloys, combinations thereof and the like. Radiopaque materials tend to obstruct x-rays and thus restrict x-ray visibility to the regions in which the materials are located. However, radiopaque materials generally have structural characteristics that are advantageous with regard to medical devices. That is, some radiolucent materials lack the strength and/or rigidity of radiopaque materials and certain design modifications may be made to provide adequate structural integrity of the implant device 510. Radiopaque materials generally have increased rigidity as compared to radiolucent materials and thus radiopaque materials may tend to maintain bone body alignment despite the rigorous pressures and forces generated by a patient implanted with the implant device 510. Thus, it may be desirable to construct portions of the implant device 510 from radiopaque materials such as metal and other portions of the implant device 510 from radiolucent materials so that a desired level of strength and/or rigidity is obtained and also x-ray visibility is enhanced. For example, as shown in FIG. 35, the chamber member 696 connected to the first and second legs 620, 630 of the primary member 600 can be constructed from radiolucent material in order to enhance the x-ray visibility of the fusion material located in the peripherally-enclosed area formed by the chamber member 696 and first and second legs 620, 630 of the primary member 600 and the surrounding bone bodies. However, it is to be appreciated that radiopaque material may be used in otherwise radiolucent devices for other reasons. For example, devices that are primarily radiolucent may include radiopaque markers such that the location of the device may be readily ascertained.

The base member 520 of the implant device 510 can include a plurality of apertures, each of which is configured to receive a corresponding bone fastener or screw 550 there through. The bone fastener 550 can include a bone screw, a plurality of which is used for securing the implant device 510 to adjacent bone bodies. The bone fasteners 550 can be made of any suitable material, such as titanium or a titanium alloy, a radiolucent material, a radiopaque material, or combinations thereof. The plurality of bone fasteners 550 can all have the same shape, such as that shown in FIGS. 32 and 33. In the depicted examples, the bone fasteners each have a radiused head 690. As used herein, the term "radiused head" means that the lower portion of the bone screw head, i.e., the portion that is nearest the shank, is generally rounded, to thereby permit the bone screws to toggle within their respective holes 640 and slots 680.

In another embodiment, the bone screws 550 configured to pass through the apertures in the base member 520 can have pointed ends which include a cutting flute on the tip. The cutting flute at the tip of the bone screw 550 allows the screw to be self-drilling or self-tapping. Thus, the use of a bone screw 550 having a self-drilling or self-tapping tip makes the use of a drill or center punch optional.

For an enhanced fit of the implant device 510, a portion of bone can be trimmed or otherwise removed from a lip osteophyte of a bone body at an angle corresponding to bone screw holes 640, 680. The angles of the bone screws 550 relative to the bone surfaces of the bone bodies can affect the anchoring of bone screws 550. For example, the lip osteophyte is the strongest part of a vertebra, and thus angling the bone screws 550 through the lip osteophyte increases the ability of the base member 520 to stay anchored to the vertebral bodies. By being angled, each bone screw 550 is positioned along an angle of rotation of a corresponding bone body as well as an angle of settling of the bone body. This configuration places each screw 550 in a protected position against motion of the spinal column. As a result, significant shear forces are not exerted on the screws 550 as the vertebral bodies rotate and/or settle.

The primary member 600 includes at least one, and possibly two as shown, first bone screw holes 640 extending there through, each being configured to receive a corresponding bone fastener or screw 550. The first bone screw holes 640 in the primary member 600 are located on the front face of the primary member 600 and face outward from the patient when the implant device 510 is inserted. The bone screw holes 640 are configured such that the bone screws 550 extend through the holes 640 at an angle. As a result, each bone screw extending through the first bone screw holes 640 can enter the bone body at an angle. Each of the first bone screw holes 640 is sufficiently large to allow a portion of a respective bone screw 550 to pass there through but not large enough to allow a retaining portion of the bone screw through, such as the head 690 of the bone screw. Further, each of the first bone screw holes 640 has a seat 665 on which the retaining portion of a respective bone screw rests. Each seat 665 has a generally concave spherical shape and the surface of the retaining portion of the bone screw 550 in contact with the seat 665 has a complementary convex spherical configuration. Consequently, the bone screws 550 are free to pivot on the seats 665. The primary member 600 also includes a threaded hole 670 for receiving a restraining means configured to mitigate the backing out of at least one bone fastener from a bone body.

The secondary member 610 includes a second bone screw hole 680 in the form of an elongated slot for receiving a bone screw. The bone screw is introduced into the second bone screw hole 680 and into a second bone body. The second bone screw hole 680 is configured such that a bone screw can slide and rotate within the slot relative to the base member 520 and generally toward the primary member 600. Thus, in use, as two adjacent bone bodies, to which the base member 520 is fixed, collapse or settle and move toward each other, the bone screw contained within the second bone screw hole 680 will slide within the slot and move with the bone body into which it extends in a direction toward the primary member 600 and the other bone body. It is worth noting that since the slot is at an angle to the surface features, it is actually longer in the plane of the secondary member than the surface features are tall. In other words, the slot provides screw movement in the vertical direction equivalent to the height of the surface features.

At least one and possibly two projections 683 extend upwardly from the top surface 650 of the base member 520. The projections 683 contact a surface of the bone bodies to provide a stop when inserting the base member 520 between the bone bodies. The projection 683 provides a base or shelf that contacts a bone body in order to stop the implant device 510 against a corresponding bone body upon insertion into a patient. Although not shown in FIG. 32, the at least one projection 683 can alternatively be positioned to extend from the bottom surface of the primary member 600.

Figure 33:
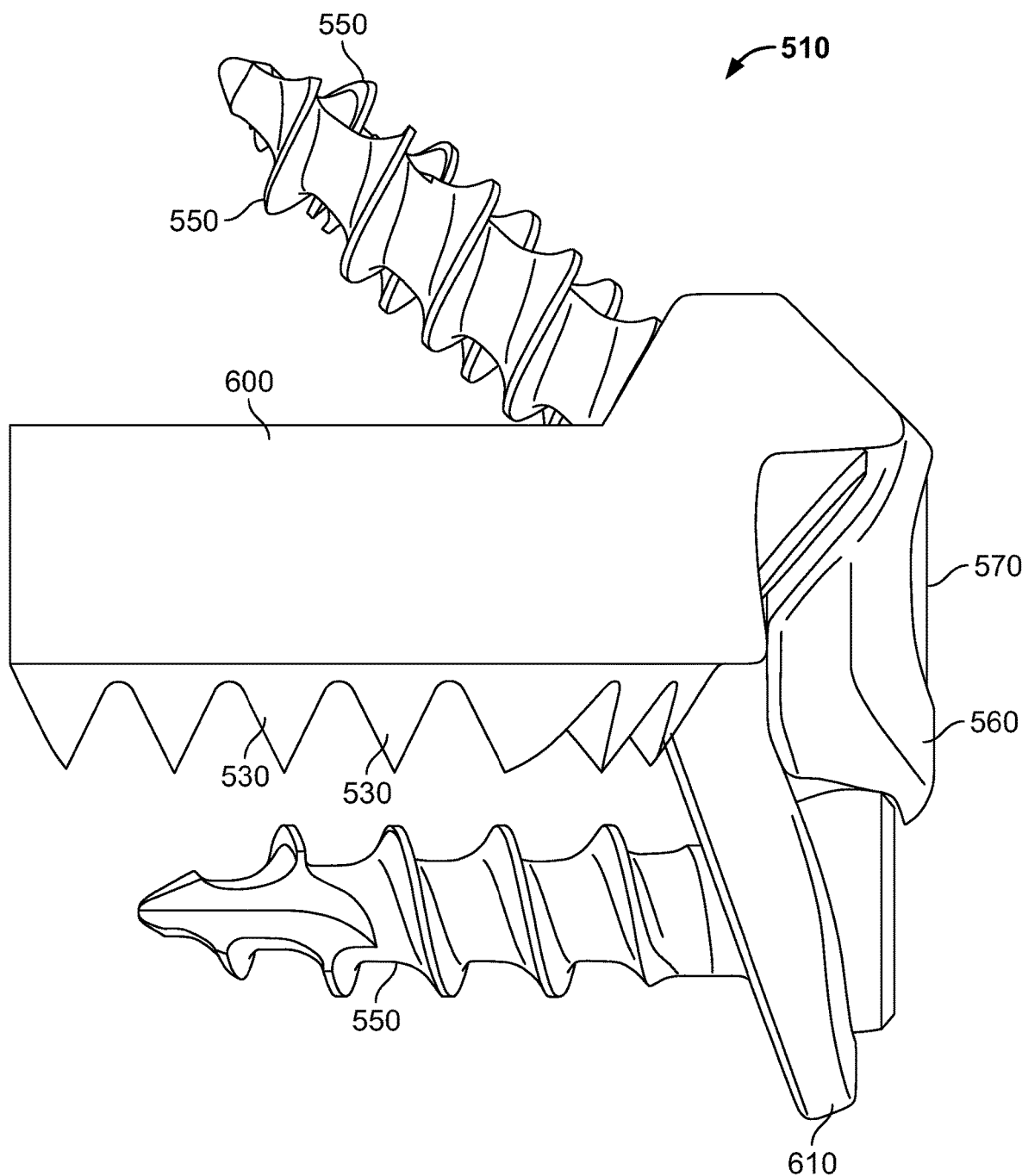
FIG. 33 is a side view of an implant device in accordance with an aspect of the present invention.

As shown in FIG. 33, the implant device 510 may include restraining means for restricting movement of one or more bone fasteners 550 coupled to the base member 520. The restraining means may be any means for securely covering at least a portion of at least one bone fastener 550 so that the bone fastener 550 is prevented from backing out of a bone body once screwed in. In the depicted embodiment, the bone screw restraining means includes a restraining plate 560 and a restraining plate fixing means 570, such as a screw that can be configured to fit into hole 670. As such, the restraining plate 560 could merely be a cover plate. The restraining plate 560 may be made of any suitable material known in the art, such as titanium or a titanium alloy, a radiolucent material, a radiopaque material, or combinations thereof. The restraining means does not have to be permanently fixed to the base member and may be removable. In the shown example, the restraining plate 560 is configured to correspond with a recessed region of the base member 520. The recessed region facilitates proper positioning of the restraining plate 560. The thickness of the restraining plate 560 should generally be as thin as possible, for example in the range from about 0.5 mm to about 2 mm. Alternative example embodiments of the restraining plate 560 and the way the embodiments interface with the bone fasteners are described herein. Also, the restriction of movement of one or more bone fasteners provided by restraining means may include control of relative motion (i.e., resistance to relative motion or changing resistance to relative motion) between one or bone fasteners and the base plate during subsidence. Still further, it is to be appreciated that within yet another example the restriction of movement as provided by restraining means may be considered to include both (1) bone fastener back-out prevention and (2) control of relative motion between one or bone fasteners and the base plate during subsidence.

Additionally, it is to be appreciated that any other suitable bone screw restraining means can be used in connection with the present invention. For example, the bone screw restraining means can include multiple restraining plates that cover different bone screws. Alternatively, the bone screw restraining means can include one or more screws with heads that overlap at least a portion of one or more bone screws to thereby prevent the bone screws from backing out.

In another embodiment, the peripherally-surrounded chamber 692 formed by the primary member 600 can be divided into multiple interior compartments by interior members. Interior members can be composed or radiolucent or radiopaque materials. In order to increase radiographic evaluation of adjacent bone bodies and fusion material contained in each compartment of the peripherally-surrounded chamber 692, the interior members are possibly composed of radiolucent material. The peripherally-surrounded chamber 692 has a substantially flat inner face surface formed by the primary member 600. As illustrated, the interface members 530 can extend from the bottom surface of the peripherally-surrounded chamber 692 in order to provide controlled subsidence with an adjacent bone body. Although not shown, the interface members can alternatively extend from the top surface of the peripherally-surrounded chamber 692 or from both the top and bottom surfaces of the chamber 692.

Figure 34:
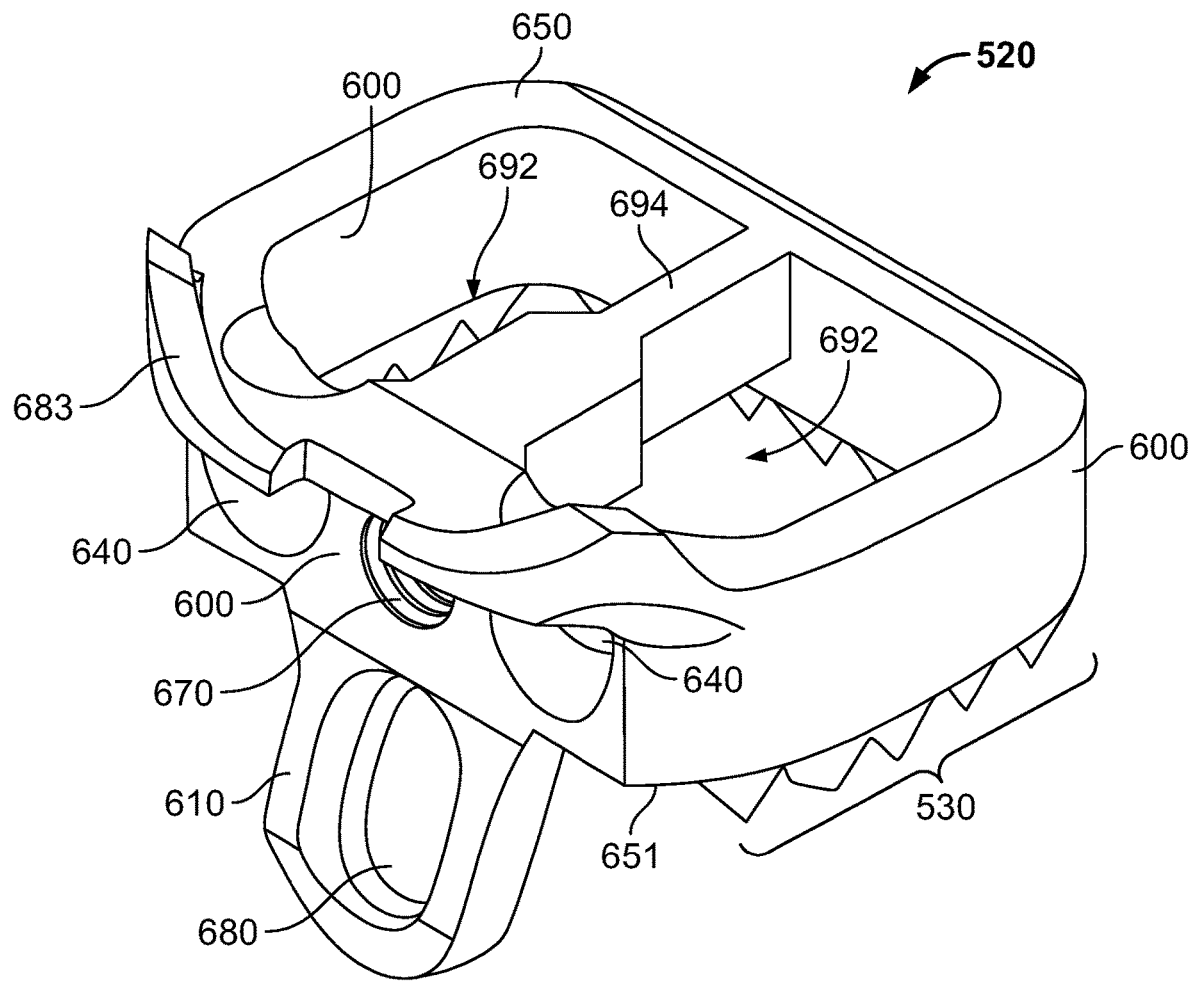
FIG. 34 is an angled front perspective view of a base member of an implant device including a peripherally-surrounded, multiple-compartment chamber in accordance with an aspect of the present invention.

As shown in FIG. 34, a center interior member 694 can extend between the opposing inner surface faces of the chamber 692 such that the chamber 692 is divided into two or more compartments that can each hold or house fusion material to be placed between two adjacent bone bodies. As illustrated, the interior member 694 of FIG. 34 extends from a portion of the inner face of the peripherally-surrounded chamber 692 and is connected to an opposing inner face of the chamber 692 or primary member 600. The addition of interior members, such as member 694, in the peripherally-surrounded chamber 692 can add overall support and strength to the implant device 510. Interior members can further secure the fusion material between two bone bodies. It should be appreciated that one possible benefit associated with the presence of the interior member 694 is that it helps prevent PEEK implants from fracturing if they are impacted between the bones with excessive force.

It is possible to load fusion material such as bone paste or bone chips into the peripherally-surrounded chamber 692 prior to insertion of the implant device 510 between adjacent bone bodies (e.g., vertebrae). However, it may be easier to insert a chamber member having an open anterior face between adjacent bone bodies. In this case, the chamber member can then be packed with fusion material from the anterior face and then sealed off with a plate, such as the base member 520. Along this line, in order to ease the packing of the peripherally-surrounded chamber 692 and the overall insertion of the implant device 510 into a patient, it may be desirable to detach the chamber member 696 which forms a portion of the peripherally-surrounded chamber 692 from the primary member 600. In accordance with another aspect of the present invention, FIG. 35 illustrates that the primary member 600 can include a detachable chamber member 696 that encloses the open area or peripherally-surrounded chamber 692 that is configured to receive fusion material. The primary member 600 can further include a first leg 620 and a second leg 630 that form a curved open arc for receiving fusion material. As illustrated, the first and second legs 620, 630 of the primary member 600 can form generally a U-shape. The detachable function of the chamber member 696 allows the U-shaped open area formed by the first and second legs 620, 630 of the primary member 600 and the U-shaped chamber member 696 itself to be packed with fusion material separately before being subsequently implanted between two adjacent bone bodies.

The chamber member 696 can be constructed from radiolucent material or radiopaque material. Because the chamber member 696 can potentially limit radiographic evaluation of the fusion material and adjacent bone bodies, it may be desirable to construct the chamber member 696 from radiolucent material. As shown, the chamber member 696 has a U-shape. However, the chamber member 696 can have any shape or be configured to match the shape of an adjacent bone body. When the chamber member 696 is connected with the first and second legs 620, 630 of the primary member 600, the peripherally-surrounded chamber 692, as shown, is generally rectangular. Although not shown, the peripherally-surrounded chamber 692 can be circular or any other desirable shape depending on the configuration of the chamber member 696 and first and second legs 620, 630. The chamber member 696 further has a top surface and a bottom surface that corresponds and aligns with the top 650 and bottom 651 surfaces of the primary member 600.

As shown in FIG. 35, the chamber member 696 can be connected to the first and second legs 620, 630 of the primary member 600 by a fastener, such as a screw or dowel, which can be inserted in the illustrated attachment holes 710. The attachment holes 710 extend through the first and second legs 620, 630 of the primary member 600 and are designed to be in register with the corresponding attachment holes 710 in the chamber member 696 when the implant device 510 is assembly such that the chamber member 696 is attached or fastened to the primary member 600 in order to form the peripherally-surrounded chamber 692. The attachment face 697 of the first and second legs 620, 630 is substantially flat such that it fits flush with the attachment face 697 of the chamber member 696. Thus, when the first and second legs 620, 630 are fastened to the chamber member 696, the attachment faces 697 are in register and the chamber member 696 is tightly secured to the primary member 600.

Figure 36:
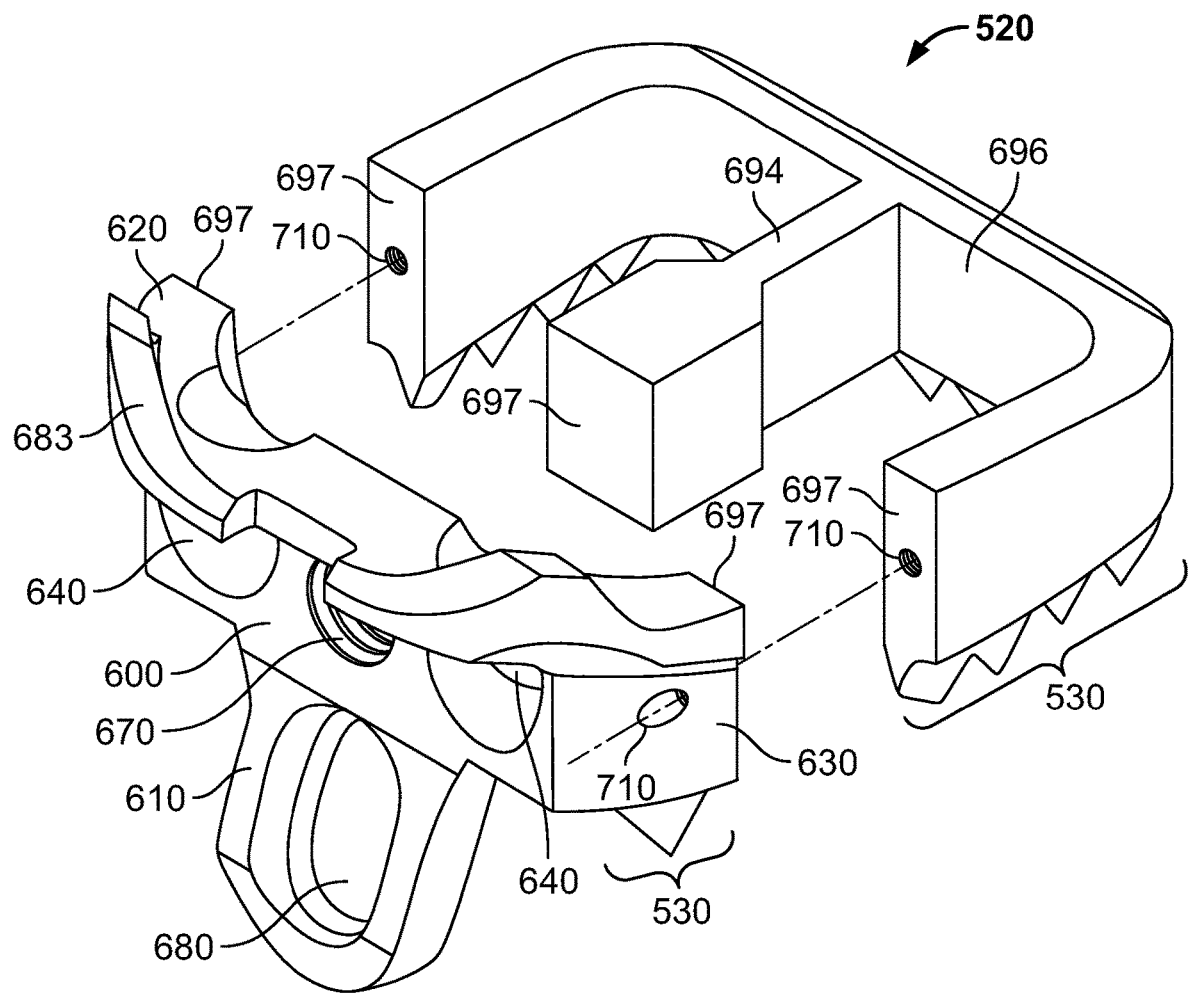
FIG. 36 is an angled front perspective view of a base member of an implant device including a laterally-enclosable, multiple-compartment chamber in an unassembled position in accordance with an aspect of the present invention.

It is to be appreciated that the peripherally-surrounded chamber 692 can be divided into more than one interior compartment if desired, such as that shown in FIG. 36, for example. FIG. 36 illustrates a U-shaped detachable chamber member 696 having an interior member 694 extending outwardly from the inner face of the chamber member 696 in a direction parallel with the ends of the chamber member 696 having the attachment faces 697. The primary member 600 and chamber member 696 can be coupled together by any suitable structure or conventional means known in the art. As shown, the interior member 694 has an attachment face 697 that is substantially flat. The attachment face 697 of the interior member 694 is designed to align and fit flush with a portion of the surface of the primary member 600.

Although not shown, the attachment face 697 of the interior member 694 can include a threaded fastener hole. The hole 670 could be configured differently, e.g., as a clearance hole, such that the restraining means can extend into the fastener hole of the interior member 694. In this case, the fastener used to attach the restraining means to the base member 520 can extend into the interior member 694 in order to secure the detachable chamber member 696 to the primary member 600. Similarly as shown in FIG. 35, the attachment faces 697 of the chamber member 696 and first and second legs 620, 630 can include attachment holes 710 for fastening the two together. A screw, dowel or like fastener can be used to secure the chamber member 696 to the first and second legs 620, 630 of the primary member 600.

Figure 37:
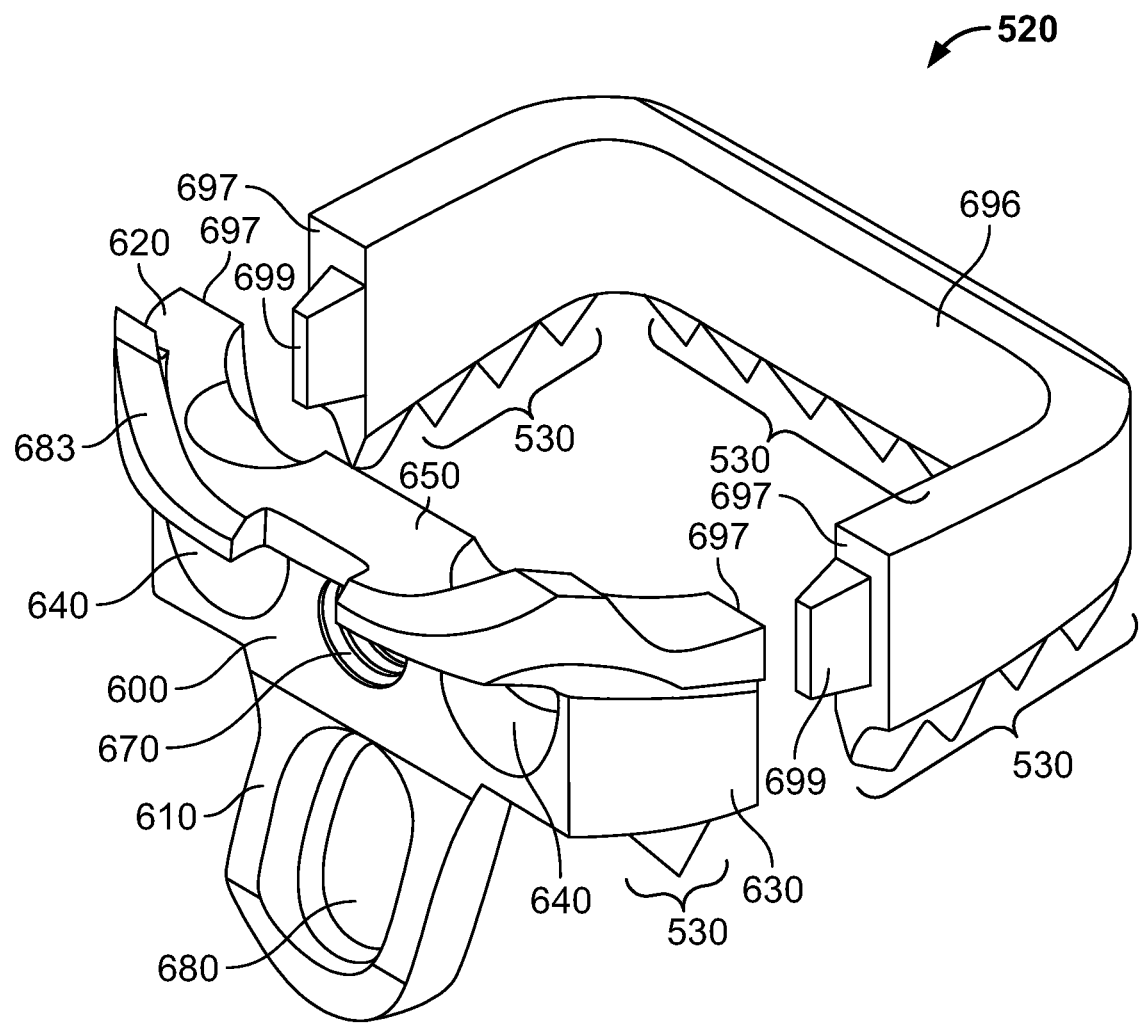
FIG. 37 is an angled front perspective view of a base member of an implant device including a laterally-enclosable chamber in the unassembled position in accordance with an aspect of the present invention.
Figure 38:
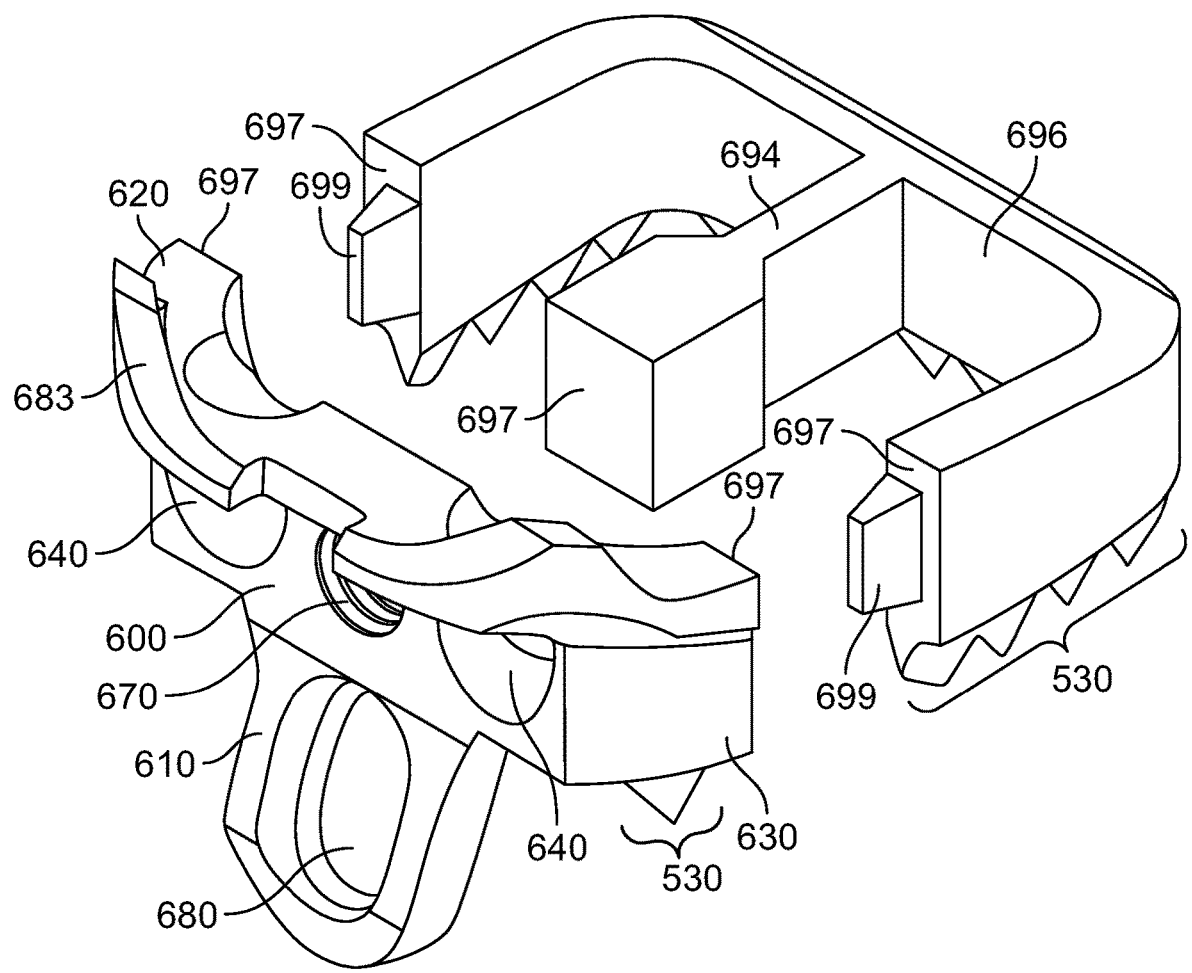
FIG. 38 is an angled front perspective view of a base member of an implant device including a laterally-enclosable, multiple-compartment chamber in an unassembled position in accordance with an aspect of the present invention.

The chamber member 696 can be attached to the primary member 600 in a number of alternative methods. For example, in another embodiment, FIGS. 37 and 38 illustrate a peg and slot system that can be used to secure the chamber member 696 to the primary member 600. The attachment faces 697 of the chamber member 696 can include a peg 699 that corresponds to a slot (not shown) in the attachment faces 697 of the first and second legs 620, 630 of the primary member 600. The slot is of like shape and has dimensions as that of the peg 699 so when fit together the peg 699 and slot are secured tightly. An adhesive that is conventional in the art can also be used to secure the peg 699 and slot together in order to ensure that the chamber member 696 is securely attached to the primary member 600 of the implant device 510.

Figure 39:
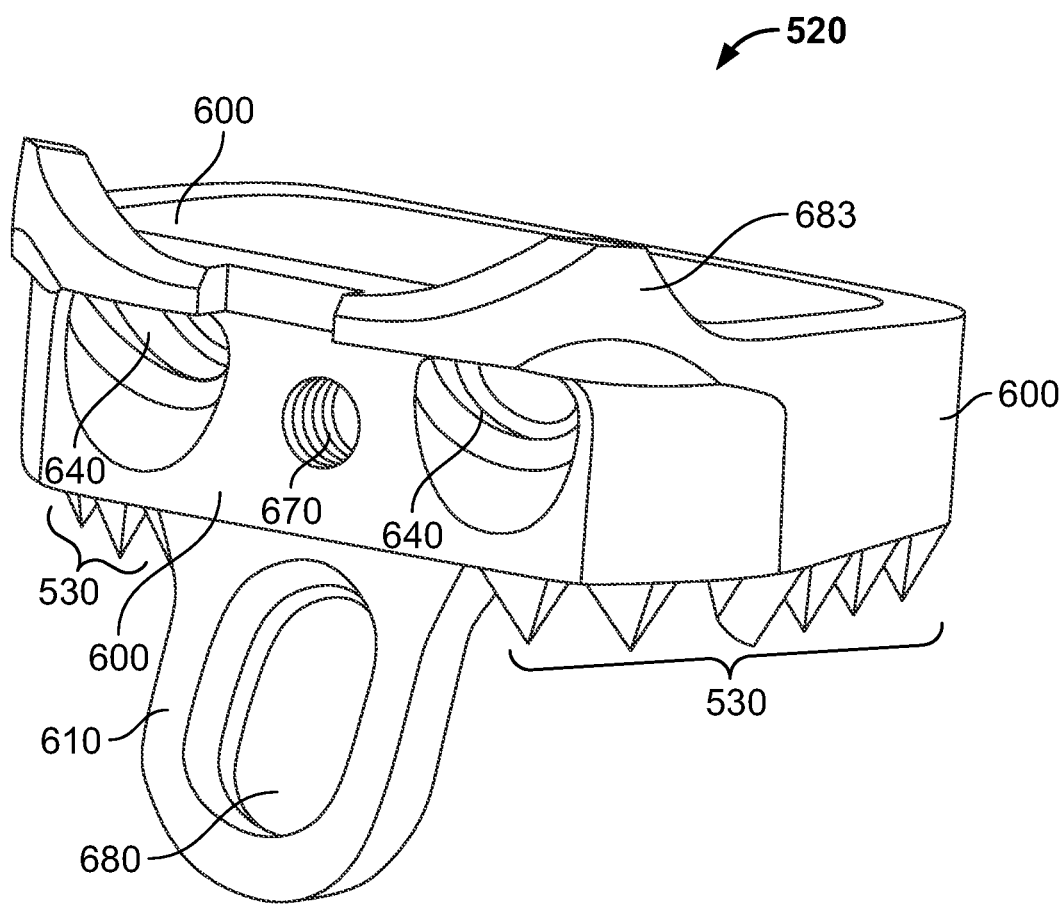
FIG. 39 is a front perspective view of a base member of an implant device including a peripherally-surrounded chamber in accordance with an aspect of the present invention.

In order to address the disadvantage that some radiolucent materials lack the strength of radiopaque materials, design modifications may be required to provide adequate structural integrity to the implant device 510. As illustrated in FIG. 39, the thickness of portions of the primary member 600 and secondary member 610, for example the bone screw holes 640 and slot 680 and portions surrounding the same, can be increased. Increasing the thickness of the bone screw holes 640 and/or slots 680 strengthens and adds support to the interface area between the bone screws 550 that extend into a bone body and the primary and secondary members. Increasing the thickness of these portions likewise will increase the thread length or slot thickness. Designing portions of the implant device 510, such as the primary member 600 and secondary member 610, to be thicker or bulkier than other portions can mitigate the stresses of bone body migration and toggling of the bone screws the forces that may cause the implant device 510 to bend, crack or otherwise be damaged.

It is to be appreciated that the implant device may include various other features. Some of these features may include features set forth within the patent applications identified herein and incorporated herein by reference. Some examples of the feature are shown in FIGS. 40-44. Some of the views are sectioned to show specific details. Such example feature may be utilized within any of the above mentioned embodiments. Of course, the shown features are merely examples and are not to be construed as limitations on the present invention.

Figure 40:
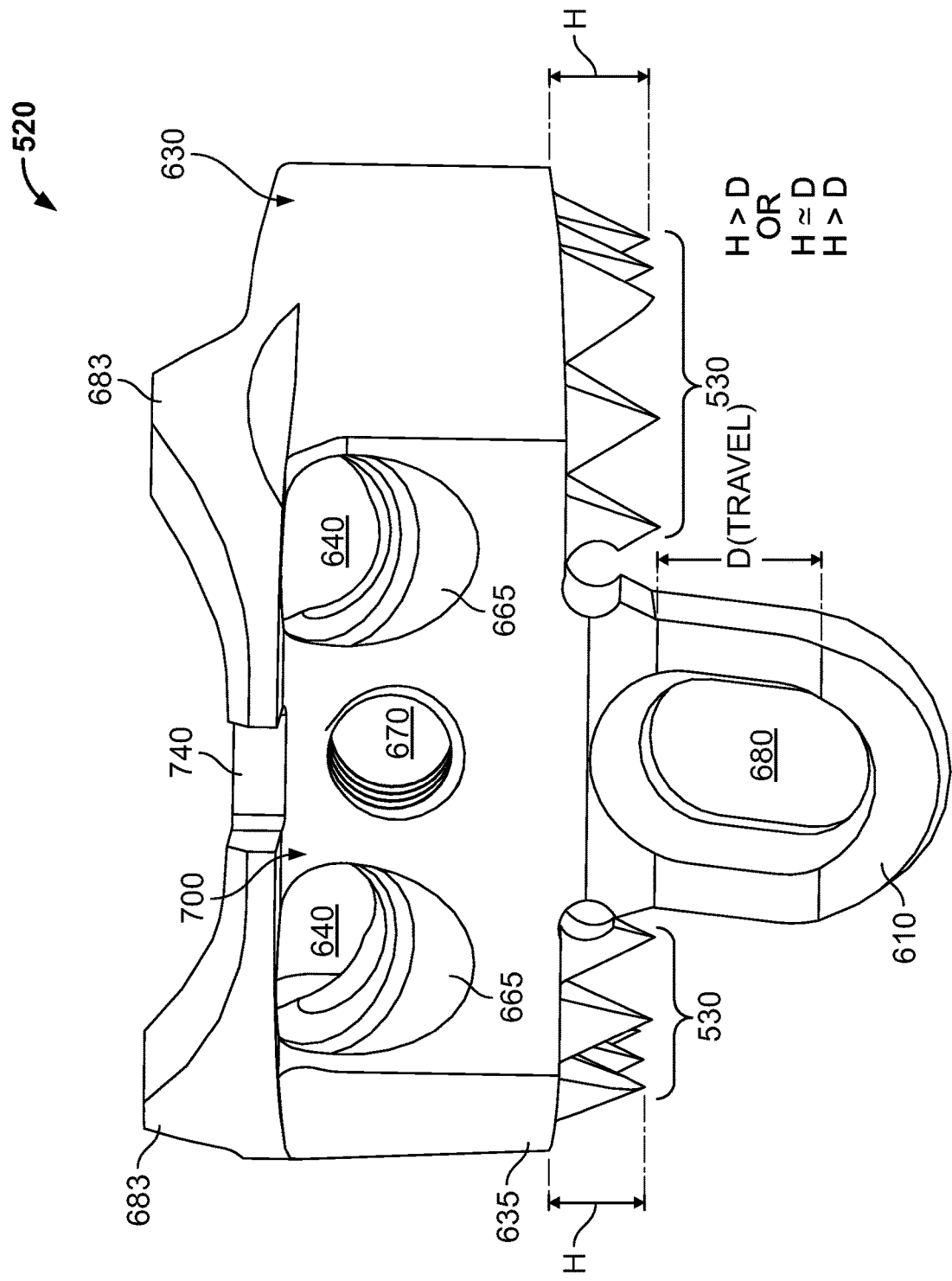
FIG. 40 is a front perspective view of a base member of an implant device illustrating possible modifications to the above-identified embodiments in accordance with an aspect of the present invention.

Turning to FIG. 40, as mentioned, the effective travel height (H) of the interface members 530 relates to a depth of penetration of the interface members into the bone body. However, the height (H) can also have an interrelationship with other relative movements that are associated with the implant device 510. For example, penetration of the interface members 530 into the bone body can be coordinated with pivoting and/or sliding of one or more bone screws relative to their respective holes 640 and slots 680 for controlled subsidence. As shown in FIG. 40, the bone screw associated with the slot can have a travel distance D. In one example concerning relative sliding within the slot 680, as the interface members 530 reach a fully-embedded state, the screw will reach the at the end of the slot 680. Such an example can be generally characterized by considering H to be equal to or approximately equal to D. Thus, the respective bone fastener is located within the slot so the screw travel matches penetration subsidence of the interface members into the bone body. Also the two projections 683 extend upwardly from the top surface 650 of the base member 520 with a space 740 there between.

Other examples concerning relative dimensioning are contemplated. Such other examples include relative sliding travel of the screw within the slot 680 to end before the interface members 530 reach a fully-embedded state and relative sliding travel of the screw within the slot 680 to still be permitted after the interface members 530 reach a fully-embedded state. Such examples can generally be characterized by considering H to be greater than D and by considering H to be less than D, respectively. Also, placement and sliding travel are possible variables. For example, the respective bone fastener can be placed to reach an end of the elongated slot and then toggle in the slot to permit the interface members to further penetrate into the bone body.

Figure 41:
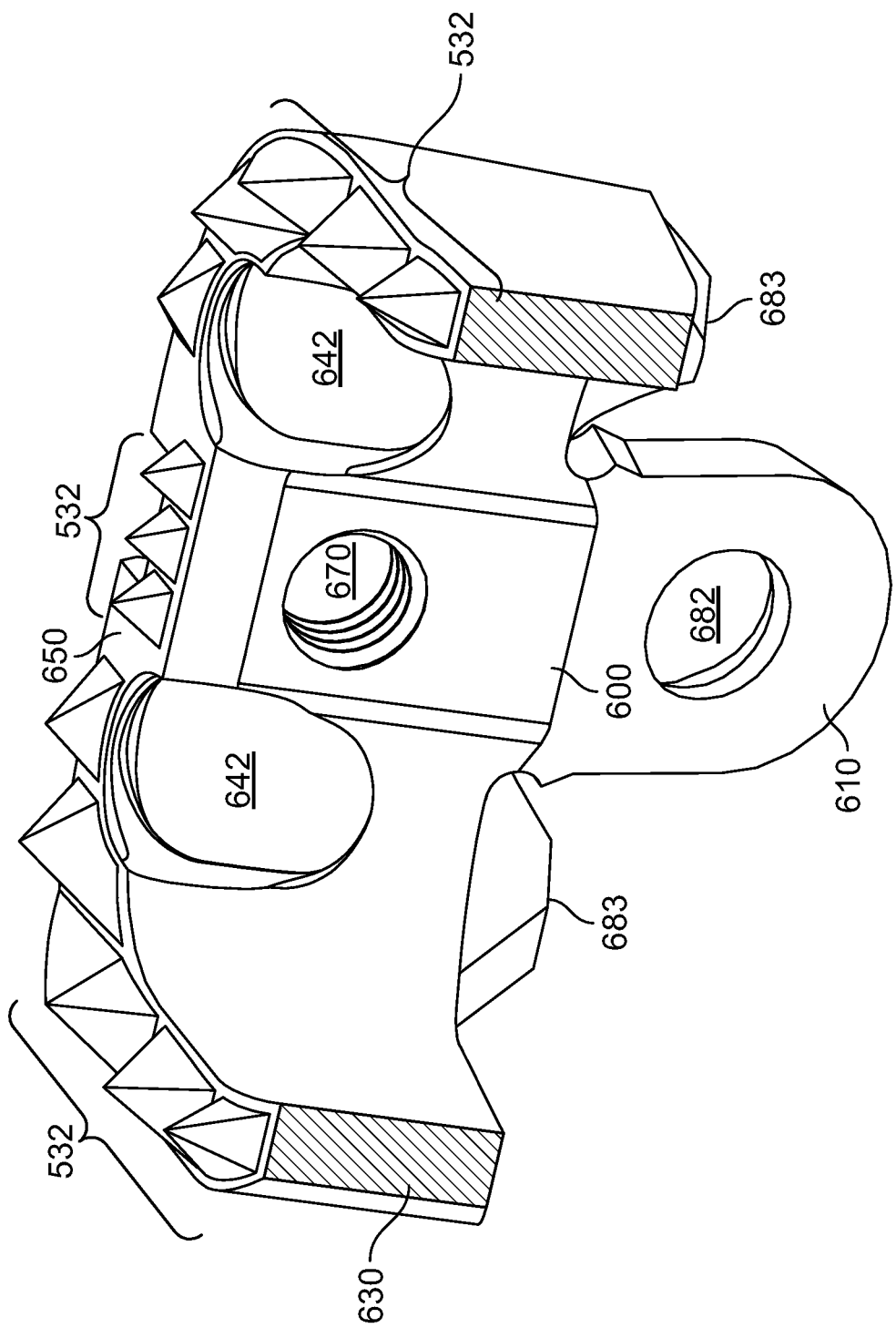
FIG. 41 is partially broken away rear perspective view of a base member of an implant device illustrating possible modifications to the above-identified embodiments in accordance with an aspect of the present invention.
Figure 42:
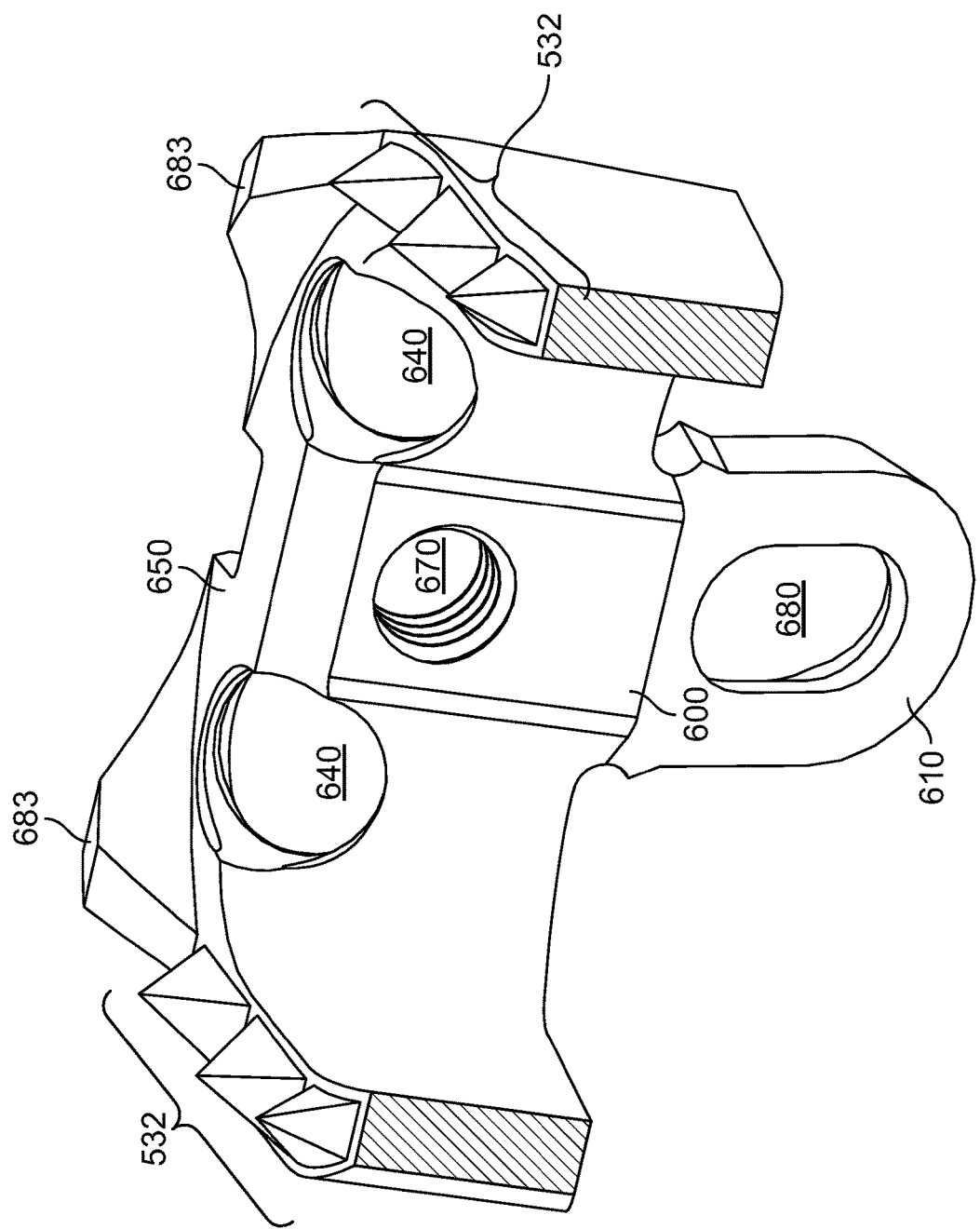
FIG. 42 is partially broken away rear perspective view of a base member of an implant device illustrating possible modifications to the above-identified embodiments in accordance with an aspect of the present invention.

FIG. 41 shows yet another example of another feature. Specifically, the interface members 532 could be located on the top surface. Thus, the location of the interface members is inverted. Another possible inversion relates to the holes and slots. Specifically, FIG. 42 shows the replacement of the holes (640, FIG. 41) with elongate slots 642 (FIG. 42) and replacement of the elongate slot (680, FIG. 41) with a non-elongate hole 582.

Figure 43:
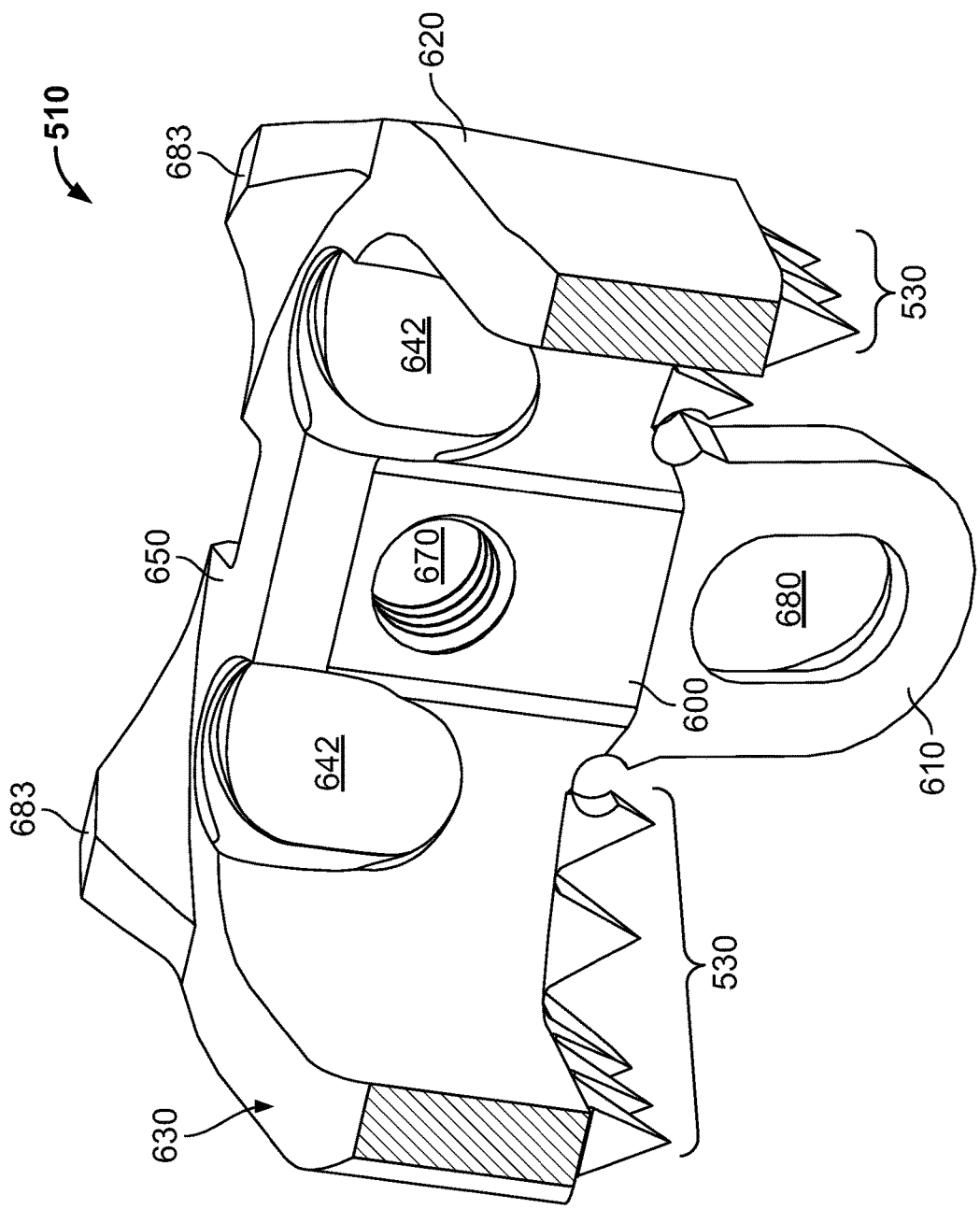
FIG. 43 is partially broken away rear perspective view of a base member of an implant device illustrating possible modifications to the above-identified embodiments in accordance with an aspect of the present invention.
Figure 44:
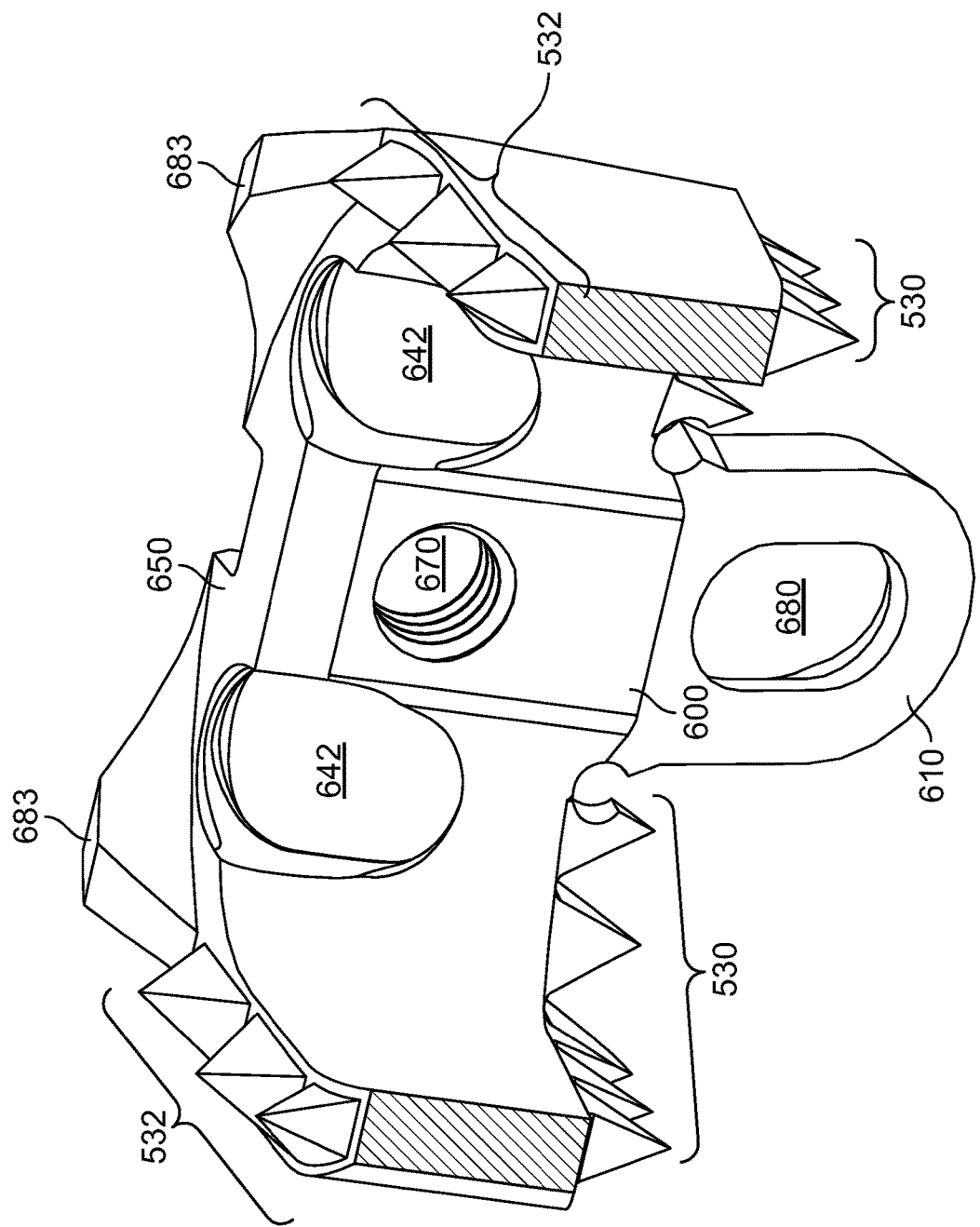
FIG. 44 is partially broken away rear perspective view of a base member of an implant device illustrating possible modifications to the above-identified embodiments in accordance with an aspect of the present invention.

Also, the above-mentioned modifications can be combined within various arrangements. For example, FIG. 43 shows that only slots 642 and 680 are provided. In other words, all holes are modified to slots. As another example, FIG. 44 shows that interface member 530, 532 can be located on both the bottom and top. FIG. 44 also shows the use of only slots 642 and 680. It is to be appreciated that such a combination of interface member 530, 532 and slots 642, 680 can provide for many types of subsidence control. The penetration of interface members and movement along slots can be configured and utilized in many different ways to provide different subsidence profiles. For example, subsidence could require more or less force and or time. Also, the subsidence may have different segments, each with a different profile.

Also, another aspect that can affect the subsidence profile, the interface members 530, 532 can be of any height or combination of heights. Thus, if a plurality of interface members 530, 532 extend from a surface of the base member, each interface member can be of equal heights or substantially taller or shorter than other interface members. FIG. 42 shows interface members 532 that have substantially dissimilar heights depending on the amount of subsidence resistance that is desired. Also, as compared to the interface members on the top and bottom, any relative dimensioning is possible. For example, the height of the interface members extending from the top surface may be greater, about the same, or less than height of the interface members extending from the bottom surface.

Still further, it is contemplated that no relative sliding movement occurs between one, some or all of the plurality of fasteners and the base member during the controlled subsidence. This could be accomplished via use of only holes and no slots. In the alternative, a bone screw could be held against movement along a slot. For such a scenario, pivoting may occur and one of more of the bone screws.

While shown embodiments of the present invention are described for supporting adjacent cervical vertebrae in the anterior region of the vertebrae, persons skilled in the art would recognize that the bone plate of the present invention may be utilized to support adjoining cervical, thoracic and lumbar in the region of the vertebral body. Further, the device and method of the invention is not limited to vertebral bodies, but can also be used to join two other pieces of bone in other parts of the body.

While embodiments and applications of this invention have been shown and described, it would be apparent to those skilled in the art that many more modifications are possible without departing from the inventive concepts herein. The invention, therefore, is not to be restricted except in the spirit of the appended claim(s).

What is claimed is:

1. An apparatus, comprising:
a base plate having a top surface, a bottom surface, and first and second ends, the base plate defining a plurality of bone anchor holes that each extend from the top surface toward one of the first and second ends, the plurality of bone anchor holes including a first bone anchor hole extending from the top surface and terminating in a first opening at least partially defined by the first end and a second bone anchor hole extending from the top surface and terminating in a second opening at least partially defined by the first end, the first end including a substantially flat portion extending from the first opening to the second opening; and
a chamber structure configured to be coupled to the base plate, the chamber structure configured to maintain disc space across a bone graft site between adjacent vertebral bones,
the base plate and the chamber structure configured to be implanted between the adjacent vertebral bones with (1) the base plate fitting primarily between anterior portions of the adjacent vertebral bones and (2) the chamber structure extending posteriorly from the base plate,
the base plate, when implanted, configured to bear weight along portions of the first and second ends of the base plate fitted between the anterior portions of the adjacent vertebral bones, while sharing weight with bone graft material placed between the adjacent vertebral bones and in a space at least partially defined by the chamber structure;
the top surface of the base plate is generally (1) flat and (2) of rectangular shape when viewed in an anterior-to-posterior direction.

2. The apparatus of claim 1, wherein the base plate, when implanted, does not contact an anterior surface of at least one of the adjacent vertebral bones.

3. The apparatus of claim 1, wherein the base plate, when implanted, fits primarily between anterior portions of lip osteophytes of the adjacent vertebral bones.

4. The apparatus of claim 1, wherein all weight-bearing portions of the first and second ends of the base plate are shaped to fit between the anterior portions of the adjacent vertebral bones.

5. The apparatus of claim 1, wherein the base plate has a maximum anterior-to-posterior dimension that is less than a maximum anterior-to-posterior dimension of the chamber structure.

6. The apparatus of claim 1, wherein the base plate has a maximum anterior-to-posterior dimension that is less than a lateral dimension of the top surface of the base plate.

7. The apparatus of claim 1, wherein the base plate and the chamber structure are formed of different materials.

8. The apparatus of claim 7, wherein the base plate is formed of a metal or metal alloy.

9. The apparatus of claim 1, wherein the chamber structure is detachable from the base plate.

10. The apparatus of claim 1, wherein the base plate and the chamber structure collectively surround the space for receiving the bone graft material.

11. The apparatus of claim 1, wherein each bone anchor hole from the plurality of bone anchor holes extends from a portion of the top surface of the base plate that is disposed between the adjacent vertebral bones when the base plate is implanted between the adjacent vertebral bones.

* * * * *